US009260371B2

(12) United States Patent
Bertozzi et al.

(10) Patent No.: US 9,260,371 B2
(45) Date of Patent: *Feb. 16, 2016

(54) COMPOSITIONS AND METHODS FOR MODIFICATION OF BIOMOLECULES

(71) Applicant: The Regents of the University of California, Oakland, CA (US)

(72) Inventors: Carolyn Ruth Bertozzi, Berkeley, CA (US); Nicholas J. Agard, Berkeley, CA (US); Jennifer A. Prescher, Berkeley, CA (US); Jeremy Michael Baskin, Berkeley, CA (US); Ellen May Sletten, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,444

(22) Filed: Apr. 23, 2013

(65) Prior Publication Data

US 2013/0344527 A1  Dec. 26, 2013

Related U.S. Application Data

(60) Division of application No. 12/049,034, filed on Mar. 14, 2008, now Pat. No. 8,431,558, which is a continuation-in-part of application No. 11/264,463, filed on Oct. 31, 2005, now Pat. No. 7,807,619.

(60) Provisional application No. 60/624,202, filed on Nov. 1, 2004.

(51) Int. Cl.
| | |
|---|---|
| *C07C 57/26* | (2006.01) |
| *C07C 63/74* | (2006.01) |
| *C07C 45/29* | (2006.01) |
| *C07C 45/51* | (2006.01) |
| *C07C 45/63* | (2006.01) |
| *C07C 49/457* | (2006.01) |
| *C07C 49/753* | (2006.01) |
| *C07C 59/72* | (2006.01) |
| *C07C 63/66* | (2006.01) |
| *C07C 69/708* | (2006.01) |
| *C07C 69/76* | (2006.01) |
| *C07D 207/416* | (2006.01) |
| *C07D 207/452* | (2006.01) |
| *C07D 249/16* | (2006.01) |
| *C07D 495/04* | (2006.01) |
| *G01N 33/531* | (2006.01) |
| *G01N 33/68* | (2006.01) |

(52) U.S. Cl.
CPC ............ *C07C 57/26* (2013.01); *C07C 45/292* (2013.01); *C07C 45/511* (2013.01); *C07C 45/63* (2013.01); *C07C 49/457* (2013.01); *C07C 49/753* (2013.01); *C07C 59/72* (2013.01); *C07C 63/66* (2013.01); *C07C 63/74* (2013.01); *C07C 69/708* (2013.01); *C07C 69/76* (2013.01); *C07D 207/416* (2013.01); *C07D 207/452* (2013.01); *C07D 249/16* (2013.01); *C07D 495/04* (2013.01); *G01N 33/531* (2013.01); *G01N 33/6803* (2013.01); *G01N 33/6842* (2013.01); *C07C 2101/18* (2013.01)

(58) Field of Classification Search
None
See application file for complete search history.

(56) References Cited

U.S. PATENT DOCUMENTS

| | | | |
|---|---|---|---|
| 6,077,954 | A | 6/2000 | Cook et al. |
| 6,329,523 | B1 | 12/2001 | Cook et al. |
| 2003/0170917 | A1 | 9/2003 | Hui |

OTHER PUBLICATIONS

STN Registry database entry for CAS RN 115228-33-6 (Published in STN Registry Jul. 9, 1988); Accessed Dec. 31, 2014.*
Bistrup, et al. "Sulfotransferases of Two Specificities Function in the Reconstitution of High Endothelial Cell Ligands for L-selectin", 1999, J Cell Biol, vol. 145, No. 4, pp. 899-910.
Dube and Bertozzi, "Metabolic Oligosaccharide Engineering as a Tool for Glycobiology", 2003, Curr Opin Chem Biol, vol. 7, No. 5, pp. 616-625.
Hanack and Spang, "Vinyl cations, 32. Solvolysis reactions of cyclononynyl and cyclooctynyl Derivatives", 1980, Chem Ber, vol. 113, No. 5, pp. 2015-2024.
Hang and Bertozzi, "Chemoselective Approaches to Glycoprotein Assembly", 2001, Acc Chem Res, vol. 34, No. 9, pp. 727-736.
Huisgen, et al. "1,3-Dipolar Cycloadditions. Past and Future", 1963, Angew Chem Int Ed Engl, vol. 2, No. 10, pp. 565-598.
Kiick, et al. "Incorporation of Azides into Recombinant Proteins for Chemoselective Modification by the Staudinger Ligation", 2002, Proc Natl Acad Sci USA, vol. 99, No. 1, pp. 19-24.
Lee, et al. "A Potent and Highly Selective Inhibitor of Human a-1,3-Fucosyltransferase via Click Chemistry", 2003, J Am Chem Soc, vol. 125, No. 32, pp. 9588-9589.

(Continued)

*Primary Examiner* — Alicia L Otton
(74) *Attorney, Agent, or Firm* — Bozicevic, Field & Francis LLP; Paula A. Borden; Glenn J. Foulds

(57) ABSTRACT

The present invention provides modified cycloalkyne compounds; and method of use of such compounds in modifying biomolecules. The present invention features a cycloaddition reaction that can be carried out under physiological conditions. In general, the invention involves reacting a modified cycloalkyne with an azide moiety on a target biomolecule, generating a covalently modified biomolecule. The selectivity of the reaction and its compatibility with aqueous environments provide for its application in vivo (e.g., on the cell surface or intracellularly) and in vitro (e.g., synthesis of peptides and other polymers, production of modified (e.g., labeled) amino acids).

16 Claims, 13 Drawing Sheets

(56) References Cited

OTHER PUBLICATIONS

Li, et al. "1,3-Dipolar cycloaddition of azides with electron-deficient alkynes under mild condition in water", 2004, Tetrahedron Letters, vol. 45, No. 15, pp. 3143-3146.

Link, et al. "Non-canonical Amino Acids in Protein Engineering", 2003, Curr Opin Biotechnol, vol. 14, No. 6, pp. 603-609.

Link and Tirrell, "Cell Surface Labeling of *Escherichia coli* via Copper(I)-Catalyzed [3+2] Cycloaddition", 2003, J Am Chem Soc, vol. 125, No. 37, pp. 11164-11165.

Meier, et al. "Ring Strain of Cycloalkynes and its Spectroscopic Consequences", 1980 Chem Ber, vol. 113, No. 7, pp. 2398-2409.

Prescher, et al. "Chemical Remodelling of Cell Surfaces in Living Animals", 2004, Nature, vol. 430, No. 7002, pp. 873-877.

Reese and Shaw, "Preparation of Medium-ring Cycloalkynes from 1-bromo-trans-cycloalkene Derivatives", 1976, J Chem Soc, Perkin Trans. 1, No. 8, pp. 890-898.

Reese and Shaw, "Preparation of cyclo-octyn-3-ol, cyclononyn-3-ol, and derivatives", 1970, J Chem Soc D, No. 18, pp. 1172-1173.

Saxon, et al. "Investigating Cellular Metabolism of Synthetic Azidosugars with the Staudinger Ligation", 2002, J Am Chem Soc, vol. 124, No. 50, pp. 14893-14902.

Saxon and Bertozzi, et al. "Cell Surface Engineering by a Modified Staudinger Reaction", 2000, Science, vol. 287, No. 5460, pp. 2007-2010.

Seo, et al. "Click Chemistry to Construct Fluorescent Oligonucleotides for DNA Sequencing", 2003, J Org Chem, vol. 68, No. 2, pp. 609-612.

Shea and Kim, "Influence of Strain on Chemical Reactivity. Relative Reactivity of Torsionally Strained Double Bonds in 1,3-dipolar cycloadditions", 1992, J Am Chem Soc, vol. 114, No. 12, pp. 4846-4855.

Speers, et al. "Activity-Based Protein Profiling in Vivo Using a Copper(I)-Catalyzed Azide-Alkyne [3+2] Cycloaddition", 2003, J Am Chem Soc, vol. 125, No. 16, pp. 4686-4687.

Speers and Cravatt, "Profiling Enzyme Activities in Vivo Using Click Chemistry Methods", 2004, Chem Biol, vol. 11, No. 4, pp. 535-546.

Turner, et al. "Heats of Hydrogenation. IX. Cyclic Acetylenes and Some Miscellaneous Olefins", 1973, J Am Chem Soc, vol. 95, No. 3, pp. 790-792.

Vocadlo, et al. "A Chemical Approach for Identifying O-GlcNAc-modified Proteins in Cells", 2003, Proc Natl Aced Sci USA, vol. 100, No. 16, pp. 9116-9121.

Wang, et al. "Bioconjugation by Copper(I)-Catalyzed Azide-Alkyne [3+2] Cycloaddition", 2003, J Am Chem Soc, vol. 125, No. 11, pp. 3192-3193.

Wilbur, et al. "Antibody Fragments in Tumor Pretargeting. Evaluation of Biotinylated Fab' Colocalization with Recombinant Streptavidin and Avidin", 1996, Bioconjugate Chem, vol. 7, No. 6, pp. 689-702.

Wittig and Krebs, et al. "Zur Existenz niedergliedriger Cycloalkine, I", 1961, Chem Ber, vol. 94, No. 12 pp. 3260-3275.

\* cited by examiner

A

B

Figures 3A-C
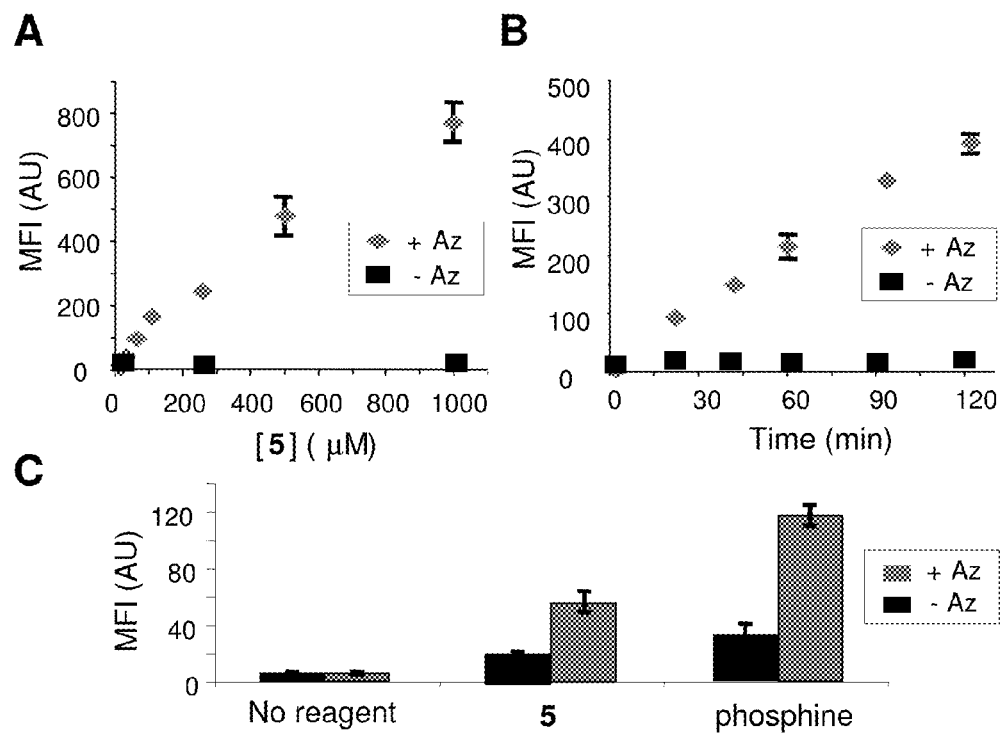

(a)

(b)

COMPOSITIONS AND METHODS FOR MODIFICATION OF BIOMOLECULES

CROSS-REFERENCE

This application is a divisional application of U.S. patent application Ser. No. 12/049,034, filed Mar. 14, 2008, which is a continuation-in-part of U.S. patent application Ser. No. 11/264,463, filed Oct. 31, 2005, which claims the benefit of U.S. Provisional Patent Application No. 60/624,202 filed Nov. 1, 2004, which applications are incorporated herein by reference in their entirety.

STATEMENT REGARDING FEDERALLY SPONSORED RESEARCH

This invention was made with Government support under grant number GM058867 awarded by the National Institutes of Health. The Government has certain rights in this invention.

FIELD OF THE INVENTION

The invention relates generally to covalent modification of molecules useful in, for example, modification of surfaces (including cell surfaces), and modification of molecules under physiological conditions (e.g., in a cellular environment).

BACKGROUND OF THE INVENTION

Selective chemical reactions that are orthogonal to the diverse functionality of biological systems are now recognized as important tools in chemical biology. As relative newcomers to the repertoire of synthetic chemistry, these bioorthogonal reactions have inspired new strategies for compound library synthesis, protein engineering, functional proteomics, and chemical remodeling of cell surfaces. The azide has secured a prominent role as a unique chemical handle for bioconjugation. The Staudinger ligation has been used with phosphines to tag azidosugars metabolically introduced into cellular glycoconjugates. The Staudinger ligation can be performed in living animals without physiological harm; nevertheless, the Staudinger reaction is not without liabilities. The requisite phosphines are susceptible to air oxidation and their optimization for improved water solubility and increased reaction rate has proven to be synthetically challenging.

The azide group has an alternative mode of bioorthogonal reactivity: the [3+2] cycloaddition with alkynes described by Huisgen. In its classic form, this reaction has limited applicability in biological systems due to the requirement of elevated temperatures (or pressures) for reasonable reaction rates. Sharpless and coworkers surmounted this obstacle with the development of a copper(I)-catalyzed version, termed "click chemistry," that proceeds readily at physiological temperatures and in richly functionalized biological environs. This discovery has enabled the selective modification of virus particles, nucleic acids, and proteins from complex tissue lysates. Unfortunately, the mandatory copper catalyst is toxic to both bacterial and mammalian cells, thus precluding applications wherein the cells must remain viable. Catalyst-free Huisgen cycloadditions of alkynes activated by electron-withdrawing substituents have been reported to occur at ambient temperatures. However, these compounds undergo Michael reaction with biological nucleophiles.

There is a need in the field for additional mechanisms to modify biological molecules through a biocompatible reaction, particularly in a biological environment.

LITERATURE

Huisgen (1963) *Angew. Chem. Int. Ed.* 2:565-598; Shea and Kim. *J. Am. Chem. Soc.* 1992, 114, 4846-4855; Reese and Shaw (1970) *Chem. Comm.* 1172-1173; Wilbur et al. *Bioconj. Chem.* 1996, 7, 689-702; Bistrup et al. *J. Cell Biol.* 1999, 145, 899-910; Saxon et al. *J. Am. Chem. Soc.* 2002, 124, 14893-14902; Hang and Bertozzi. *Acc. Chem. Res.* 2001, 34, 727-736; Link et al. *Curr. Opin. Biotechnol.* 2003, 14, 603-609; Lee et al. *J. Am. Chem. Soc.* 2003, 125, 9588-9589; Wang et al. *J. Am. Chem. Soc,* 2003, 125, 3192-3193; Kiick et al. *Proc. Natl. Acad. Sci. U.S.A.* 2002, 99, 19-24; Speers and Cravatt. *Chem. Biol.* 2004, 11, 535-546; Saxon and Bertozzi *Science* 2000, 287, 2007-2010; Link, A. J.; Tirrell, D. A. *J. Am. Chem. Soc.* 2003, 125, 1164-1165; Dube and Bertozzi. *Curr. Opin. Chem. Biol.* 2003, 7, 616-625; Vocadlo et al. *Proc. Natl. Acad. Sci. U.S.A.* 2003, 100, 9116-9121; Prescher et al. *Nature* 2004, 430, 873-877; Seo et al. *J. Org. Chem.* 2003, 68, 609-612; Li et al. *Tetrahedron Lett.* 2004, 45, 3143-3146; Wittig and Krebs. *Chem. Ber.* 1961, 94, 3260-3275; Meier et al. *Chem. Ber.* 1980, 113, 2398-2409; Turner et al. *J. Am. Chem. Soc.* 1972, 95, 790-792.

SUMMARY OF THE INVENTION

The present invention provides modified cycloalkyne compounds; and method of use of such compounds in modifying biomolecules. The present invention features a cycloaddition reaction that can be carried out under physiological conditions. In general, the method involves reacting a modified cycloalkyne with an azide moiety on a target biomolecule, generating a covalently modified biomolecule. The selectivity of the reaction and its compatibility with aqueous environments provide for its application in vivo (e.g., on the cell surface or intracellularly) and in vitro (e.g., synthesis of peptides and other polymers, production of modified (e.g., labeled) amino acids).

BRIEF DESCRIPTION OF THE DRAWINGS

FIG. 1A depicts Cu(I)-catalyzed Huisgen cycloaddition ("click chemistry"). FIG. 1B depicts strain-promoted [3+2] cycloaddition of azides and cyclooctynes.

FIGS. 3A-C depict cell surface labeling with a modified cyclooctyne compound.

DEFINITIONS

Figure 1A:
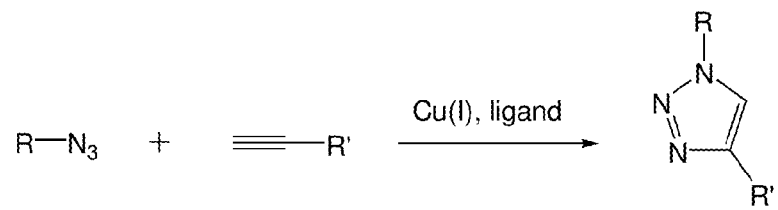
FIGS. 1A and 1B depict cycloaddition reactions.
Figure 1B:

By "reactive partner" is meant a molecule or molecular moiety that specifically reacts with another reactive partner. Exemplary reactive partners are those of the reaction of the invention, i.e., an azide group of an azide-modified target molecule and the cycloalkyne group of a modified cycloalkyne moiety.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment or its synthetic environment and is at least 60% free, at least 75% free, at least 90% free, at least 95% free, at least 98% free, or at least 99% free from other components with which it is naturally associated, or is at least 60% free, at least 75% free, at least 90% free, at least 95% free, at least 98% free, or at least 99% free from contaminants associated with synthesis of the compound.

As used herein, the term "cell" in the context of the in vivo applications of the invention is meant to encompass eukaryotic and prokaryotic cells of any genus or species, with mammalian cells being of particular interest. "Cell" is also meant to encompass both normal cells and diseased cells, e.g., cancerous cells. In many embodiments, the cells are living cells.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "physiological conditions" is meant to encompass those conditions compatible with living cells, e.g., predominantly aqueous conditions of a temperature, pH, salinity, etc. that are compatible with living cells.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term "lower alkyl", alone or in combination, generally means an acyclic alkyl radical containing from 1 to about 10, e.g., from 1 to about 8 carbon atoms, or from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

The terms "halo" and "halogen" refer to the fluoro, chloro, bromo or iodo groups. There can be one or more halogen, which are the same or different.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings.

Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)$_n$-hexyl, 2-(5'-cyano-3'-methoxyphenyl)$_n$-pentyl, 3-(2',6'-dimethylphenyl)$_n$-propyl, 4-chloro-3-aminobenzyl, 6-(4'-methoxyphenyl)-3-carboxy(n-hexyl), 5-(4'-aminomethylphenyl)-3-(aminomethyl)$_n$-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, e.g., to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a modified cycloalkyne" includes a plurality of such modified cycloalkynes and reference to "the target molecule" includes reference to one or more target molecules and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention features a strain-promoted [3+2] cycloaddition reaction that can be carried out under physiological conditions. In general, the invention involves reacting a modified cycloalkyne with an azide moiety on a biomolecule, generating a covalently modified biomolecule. The selectivity of the reaction and its compatibility with aqueous environments provides for its application in vivo (e.g., on the cell surface or intracellularly) and in vitro (e.g., synthesis of peptides and other polymers, production of modified (e.g., labeled) amino acids). The reaction is compatible with modification of living cells.

The invention provides methods and compositions for specifically and efficiently synthetically modifying cellular components in an aqueous environment, thus providing for modification of such cellular components on or in living cells. The invention uses reactive partners that are completely abiotic and are chemically orthogonal to native cellular components, thus providing for extreme selectivity of the reaction. Furthermore, the reaction can be carried out under physiological conditions, e.g., a pH of about 7 within an aqueous environment, and at about 37° C.

The invention is based in part on the discovery of a means for carrying out a modified Huisgen reaction that can be carried out in an aqueous, physiological environment. Because the reaction of the invention is highly selective and functions in aqueous solvents, the reaction can be used in a variety of applications both in vitro and in vivo. The reaction is accomplished through use of a first molecule comprising a strained cycloalkyne moiety, and second molecule comprising an azide moiety. The azide moiety on the second molecule reacts, in the absence of a catalyst, with the strained cycloalkyne moiety on the first molecule, forming a final conjugate product comprising fused azide/cycloalkyne ring. The first molecule comprising the strained cycloalkyne moiety can further comprise a moiety that allows for subsequent reactions and/or which provides for detectable labeling of the product of the final reaction. The reaction proceeds without the need for a catalyst. Instead, activation energy for the reaction is provided by azide group and the strained cycloalkyne group. The invention takes advantage of the massive bond angle deformation of the acetylene group in the cycloalkyne moiety, which provides for ring strain. For example, the bond angle deformation of the acetylene group of cyclooctyne to 163° accounts for nearly 18 kcal/mol of ring strain. This destabilization of the ground state versus the transition state of the reaction provides a dramatic rate acceleration compared to unstrained alkynes.

Modified Cycloalkyne Compounds

The present invention provides modified cycloalkyne compounds; and compositions comprising the compounds. A subject modified cycloalkyne is a compound of the formula:

where:

X is a strained cycloalkyne group, or a heterocycloalkyne group, substituted with $R_1$, and in some embodiments one or more additional groups;

Y is H; a moiety that comprises a reactive group that facilitates covalent attachment of a molecule of interest; or a molecule of interest; and $R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. In some embodiments, $R_1$ is a substituted or unsubstituted aliphatic group, e.g., a substituted or unsubstituted alkyl; a substituted or unsubstituted alkenyl; or a substituted or unsubstituted alkynyl. In some embodiments, $R_1$ is a substituted or unsubstituted phenyl.

In some embodiments, Y is a reactive group. Suitable reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, thiol, succinimidyl ester, isothiocyanate, iodoacetamide, maleimide, hydrazine, and the like. In some embodiments, Y is a reactive group selected from a carboxyl, an amine, an ester, a thioester, a sulfonyl halide, an alcohol, a thiol, a succinimidyl ester, an isothiocyanate, an iodoacetamide, a maleimide, and a hydrazine.

In some embodiments, Y is a molecule of interest, where suitable molecules of interest include, but are not limited to, a detectable label; a toxin (including cytotoxins); a linker; a peptide; a drug; a member of a specific binding pair; an epitope tag; and the like. Where Y is a molecule of interest other than a linker, the molecule of interest is attached directly to $R_1$, or is attached through a linker.

The cycloalkyne is a strained cycloalkyne, e.g., the cycloalkyne increases the rate of reaction from about 2-fold to about 1000-fold, e.g., the cycloalkyne increases the rate of reaction at least about 2-fold, at least about 5-fold, at least about 10-fold, at least about 50-fold, at least about 100-fold, at least about 500-fold, or at least about 1000-fold, compared to the rate of reaction between an azide and a linear alkyne having the same number of carbon atoms as the cycloalkyne. The strained cycloalkyne will in some embodiments be a heterocycloalkyne, e.g., the cycloalkyne will in some embodiments comprise atoms other than carbon. In some embodiments, the cycloalkyne or heterocycloalkyne will be a 7-membered ring. In other embodiments, the cycloalkyne or heterocycloalkyne will be an 8-membered ring. In other embodiments, the cycloalkyne or heterocycloalkyne will be a 9-membered ring. The strain on the cycloalkyne can be increased in a variety of ways, e.g., through the use of heteroatoms; the degree of unsaturation, or torsional strain; the use of electron-withdrawing groups, etc. In some embodiments of particular interest, the cycloalkyne is a cyclooctyne. In some embodiments, the strained cycloalkyne is a compound in which one or more of the carbon atoms in the cycloalkyne ring, other than the two carbon atoms joined by a triple bond, is substituted with one or more electron-withdrawing groups, e.g., a halo (bromo, chloro, fluoro, iodo), a nitro group, a cyano group, or a sulfone group. Where the electron-withdrawing group is a nitro group, a cyano group, or a sulfone group, the electron-withdrawing group is not directly linked to the cycloalkyne ring.

In some embodiments, a subject modified cycloalkyne is of Formula I:

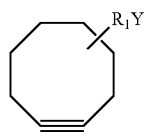

Formula I where:
Y is H; a moiety that comprises a reactive group that facilitates covalent attachment of a molecule of interest; or a molecule of interest; and
$R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons joined by the triple bond.

Exemplary, non-limiting examples of a subject cyclooctyne compound, e.g., an exemplary cyclooctyne compound of Formula I include:

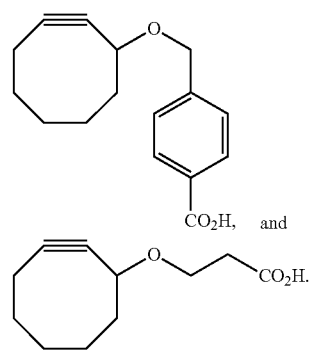

In some embodiments, the modified cycloalkyne is of Formula I, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula II:

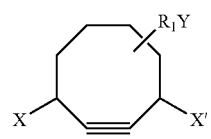

Formula II where:
each of X and X' is independently:
(a) H;
(b) one or two halogen atoms (e.g., bromo, chloro, fluoro, iodo);
(c) —W—$(CH_2)_n$—Z (where: n is an integer from 1-4 (e.g., n=1, 2, 3, or 4); W, if present, is O, N, or S; and Z is nitro, cyano, sulfonic acid, or a halogen);
(d) —$(CH_2)_n$—W—$(CH_2)_m$—Z (where: n and m are each independently 1 or 2; W is O, N, S, or sulfonyl; if W is O, N, or S, then Z is nitro, cyano, or halogen; and if W is sulfonyl, then Z is H); or
(e) —$(CH_2)_n$—Z (where: n is an integer from 1-4 (e.g., n=1, 2, 3, or 4); and Z is nitro, cyano, sulfonic acid, or a halogen);
Y is H; a moiety that comprises a reactive group that facilitates covalent attachment of a molecule of interest; or a molecule of interest; and
$R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond.

Exemplary, non-limiting examples of a subject cyclooctyne compound, e.g., an exemplary cyclooctyne compound of Formula II, include:

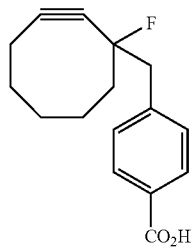 [SMILES: O=C(O)c1ccc(CC2(F)C#CCCCCC2)cc1]

In some embodiments, a subject modified cycloalkyne is of Formula III:

Formula III

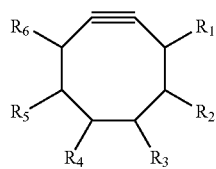

wherein each of $R_1$-$R_6$ is independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—$(CH_2)_n$—Z (where: n is an integer from 1-4 (e.g., n=1, 2, 3, or 4), wherein W, if present, is O, N, or S; and Z is nitro, cyano, sulfonic acid, or a halogen); —$(CH_2)_n$—W—$(CH_2)_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —$(CH_2)_n$—Z (where: n is an integer from 1-4 (e.g., n=1, 2, 3, or 4), and wherein Z is nitro, cyano, sulfonic acid, or a halogen);

wherein $R_3$ is optionally linked to $R_4$ through Y thus forming a substituted or unsubstituted cycloalkyl or substituted or unsubstituted heterocycloalkyl substituient on the cycloalkyne ring, wherein Y, if present, is C, O, N, or S; and wherein each of $R_1$-$R_6$ is optionally independently linked to a a moiety that comprises a reactive group that facilitates covalent attachment of a molecule of interest; or a molecule of interest.

In some embodiments of Formula $II_1$, $R_1$ is two fluoride atoms, one or more of $R_2$, $R_3$, $R_4$, and $R_5$ is a fluorophore, and $R_6$ is —$OR_7$, where —$OZ_7$ is a leaving group with a quencher (e.g., and ester, a sulfonate, etc.).

Exemplary, non-limiting examples of a subject halogenated cyclooctyne compound, e.g., a compound of Formula III, include:

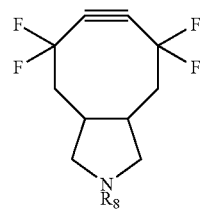

where $R_8$ is selected from H; a halogen atom (e.g., bromo, fluoro, chloro, iodo); an aliphatic group, a substituted or unsubstituted alkyl group; an alkenyl group; an alkynyl group; a carboxylic acid, an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; and a nitro.

In some embodiments, a subject modified cycloalkyne is of Formula IV:

Formula IV

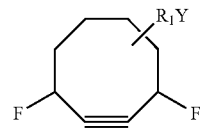

where:

Y is H; a moiety that comprises a reactive group that facilitates covalent attachment of a molecule of interest; or a molecule of interest; and $R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond.

Exemplary, non-limiting examples of a subject halogenated cyclooctyne compound, e.g., a compound of Formula IV, include:

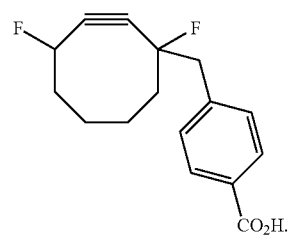 [SMILES: O=C(O)c1ccc(CC2(F)C#CC(F)CCCC2)cc1]

In some embodiments, a subject modified cycloalkyne is of Formula V:

Formula V

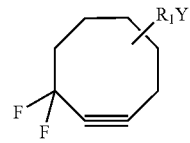

where:

Y is H; a moiety that comprises a reactive group that facilitates covalent attachment of a molecule of interest; or a molecule of interest; and $R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond, and other than the fluoride-substituted carbon.

Exemplary, non-limiting examples of a subject halogenated cyclooctyne compound, e.g., exemplary compounds of Formula V, include:

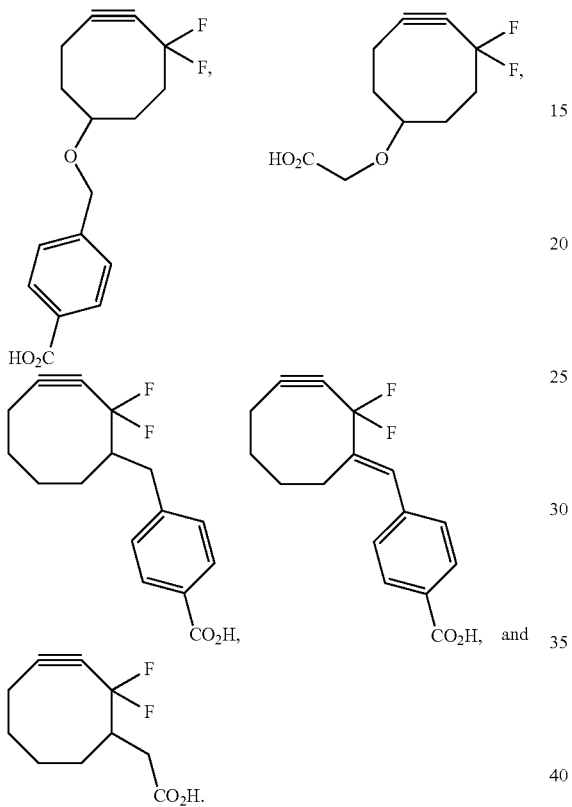

In some embodiments, a subject modified cycloalkyne is of Formula VI:

Formula VI

where Y is H; a moiety that comprises a reactive group that facilitates covalent attachment of a molecule of interest; or a molecule of interest; and $R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. $R_1$ can be at any position on the cyclooctyne group other than at the two carbons linked by the triple bond, and other than the fluoride-substituted carbons.

In some embodiments, a subject modified cycloalkyne is of Formula VII:

Formula VII

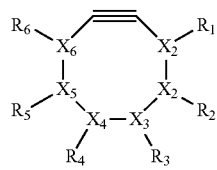

wherein five of $X_1$-$X_6$ are carbon atoms;
wherein one of $X_1$-$X_6$ is N, O, P, or S;
wherein each of $R_1$-$R_6$ is independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—$(CH_2)_n$—Z (where: n is an integer from 1-4 (e.g., n=1, 2, 3, or 4), wherein W, if present, is O, N, or S; and Z is nitro, cyano, sulfonic acid, or a halogen); —$(CH_2)_n$—W—$(CH_2)_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —$(CH_2)_n$—Z (where: n is an integer from 1-4 (e.g., n=1, 2, 3, or 4), and wherein Z is nitro, cyano, sulfonic acid, or a halogen); and wherein each of $R_1$-$R_6$ is optionally independently linked to a a moiety that comprises a reactive group that facilitates covalent attachment of a molecule of interest; or a molecule of interest.

In some embodiments, a subject compound is a compound of one of Formulas VIII and IX:

Formula VIII

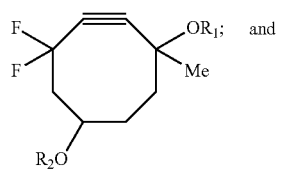

Formula IX

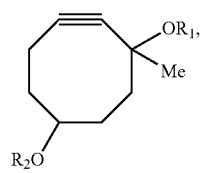

where each —OR is independently a leaving group.

In some embodiments, a subject modified cycloalkyne is a heteroalkyne of Formula X:

Formula X

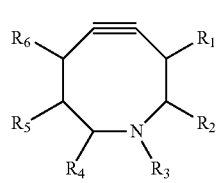

wherein each of $R_1$-$R_6$ is independently H; one or two halogen atoms (e.g., bromo, chloro, fluoro, iodo); a carboxylic acid; a methoxy group; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; a nitro; —W—(CH$_2$)$_n$—Z (where: n is an integer from 1-4 (e.g., n=1, 2, 3, or 4), wherein W, if present, is O, N, or S; and Z is nitro, cyano, sulfonic acid, or a halogen); —(CH$_2$)$_n$—W—(CH$_2$)$_m$—Z (where: n and m are each independently 1 or 2; W is O, N, S, or sulfonyl, wherein if W is O, N, or S, then Z is nitro, cyano, or halogen, and wherein and if W is sulfonyl, then Z is H); or —(CH$_2$)$_n$—Z (where: n is an integer from 1-4 (e.g., n=1, 2, 3, or 4), and wherein Z is nitro, cyano, sulfonic acid, or a halogen); and wherein each of R$_1$-R$_6$ is optionally independently linked to a a moiety that comprises a reactive group that facilitates covalent attachment of a molecule of interest; or a molecule of interest.

Exemplary, non-limiting examples of a subject azacyclooctyne compound, exemplary compounds of Formula X, include:

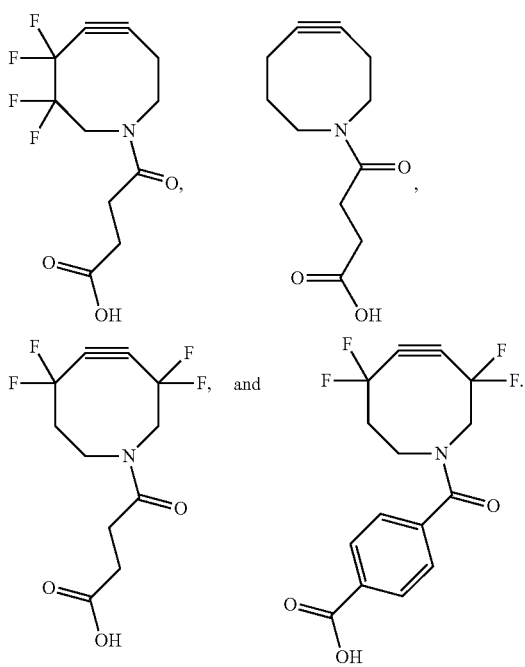

In some embodiments, a subject compound has the structure of one of Formulas XI-XVI:

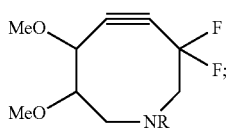
Formula XI

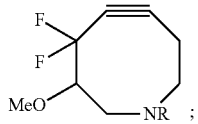
Formula XII

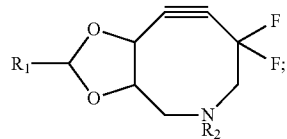
Formula XIII

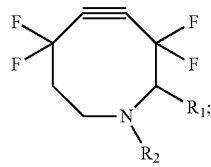
Formula XIV

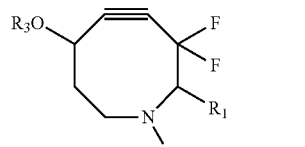
Formula XV

; and

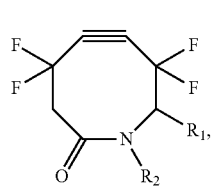
Formula XVI where R, R$_1$, R$_2$, and R$_3$ are each independently H; one or two halogen atoms (e.g., bromo, chloro, fluoro, iodo); a carboxylic acid; a methoxy group; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

wherein —OR is in some embodiments a leaving group with a quencher; and wherein each R is optionally independently linked to a a moiety that comprises a reactive group that facilitates covalent attachment of a molecule of interest; or a molecule of interest.

In some embodiments, a subject compound has the structure of Formula XVII:

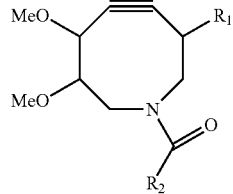
Formula XVII where R$_1$ and R$_2$ are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro; and wherein each of R$_1$ and R$_2$ is optionally independently linked to a a moiety that comprises a reactive group that facilitates covalent attachment of a molecule of interest; or a molecule of interest.

Exemplary, non-limiting examples of a subject azacyclooctyne compound, exemplary compounds of Formula XVII, include:

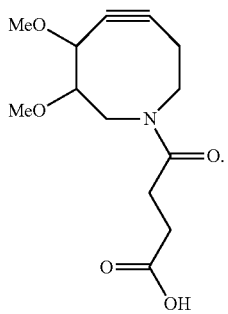

In some embodiments, a subject compound has the structure of Formula XVIII:

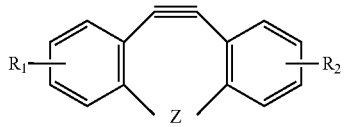
Formula XVIII where Z is —CH$_2$—CH$_2$—, —CH=CH—, —Se(O)O—, —C(O)O—, —C(R$_3$)(R$_4$)O—, —N(R$_5$)N(R$_6$)—, —CH(OR$_7$)CH$_2$—, or —S(O)O—;

where R$_1$ and R$_2$ are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

where R$_3$ to R$_7$ is each independently selected from H; a halogen atom (e.g., bromo, fluoro, chloro, iodo); an aliphatic group, a substituted or unsubstituted alkyl group; an alkenyl group; an alkynyl group; a carboxylic acid, an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro; and wherein each of R$_1$ and R$_2$ is optionally independently linked to a a moiety that comprises a reactive group that facilitates covalent attachment of a molecule of interest; or a molecule of interest.

In some embodiments, a subject compound has the structure of one of Formulas XIX, XX, and XXI:

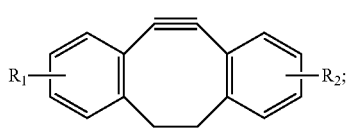
Formula XIX

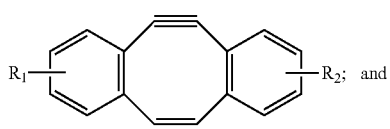
Formula XX

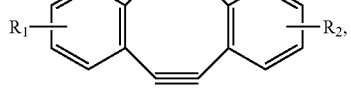
Formula XXI where R$_1$ and R$_2$ are as defined above for Formula XVIII.

In some embodiments, a subject compound has the structure of Formula XXII:

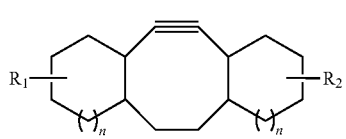
Formula XXII wherein are each independently H; one or two halogen atoms (e.g., bromo, chloro, fluoro, iodo); a carboxylic acid; an alkyl ester; an aryl ester; a substituted aryl ester; an aldehyde; an amine; a thiol; an amide; an aryl amide; an alkyl halide; a thioester; a sulfonyl ester; an alkyl ketone; an aryl ketone; a substituted aryl ketone; a halosulfonyl; a nitrile; or a nitro;

wherein each n is independently 0, 1, or 2; and wherein each of R$_1$ and R$_2$ is optionally independently linked to a a moiety that comprises a reactive group that facilitates covalent attachment of a molecule of interest; or a molecule of interest.

Molecules of Interest

In some embodiments, Y is a molecule of interest. Suitable molecules of interest include, but are not limited to, a detectable label; a toxin (including cytotoxins); a linker; a peptide; a drug; a member of a specific binding pair; an epitope tag; and the like. Where Y is a molecule of interest other than a linker, the molecule of interest is attached directly to an R group, as noted above, or is attached through a linker.

Where Y is a molecule of interest, the modified cycloalkyne comprises a molecule desired for delivery and conjugation to the azido-target substrate (azide-containing target molecule), which target substrate may be displayed on the cell surface, may reside within the cell membrane, or may be intracellular. Molecules that may be desirable for delivery include, but are not necessarily limited to, detectable labels (e.g., spin labels, fluorescence resonance energy transfer (FRET)-type dyes, e.g., for studying structure of biomolecules in vivo), small molecule drugs, cytotoxic molecules (e.g., drugs), ligands for binding by a target receptor (e.g., to facilitate viral attachment, attachment of a targeting protein present on a liposome, etc.), tags to aid in purification by, for example, affinity chromatography (e.g., attachment of a FLAG epitope), and molecules to facilitate selective attachment of the polypeptide to a surface, and the like. Specific, non-limiting examples are provided below.

Detectable Labels

The compositions and methods of the invention can be used to deliver a detectable label to a target molecule having an azide. Thus, in some embodiments, a subject modified cycloalkyne comprises a detectable label, covalently bound to the modified cycloalkyne either directly or through a linker.

Exemplary detectable labels include, but are not necessarily limited to, fluorescent molecules (e.g., autofluorescent molecules, molecules that fluoresce upon contact with a reagent, etc.), radioactive labels (e.g., $^{111}$In, $^{125}$I, $^{131}$I, $^{212}$B, $^{90}$Y, $^{186}$Rh, and the like); biotin (e.g., to be detected through reaction of biotin and avidin); fluorescent tags; imaging reagents (e.g., those described in U.S. Pat. No. 4,741,900 and U.S. Pat. No. 5,326,856), and the like. Detectable labels also include peptides or polypeptides that can be detected by antibody binding, e.g., by binding of a detectably labeled antibody or by detection of bound antibody through a sandwich-type assay. Also suitable for use are quantum dots (e.g., detectably labeled semiconductor nanocrystals, such as fluorescently labeled quantum dots, antibody-conjugated quantum dots, and the like). See, e.g., Dubertret et al. 2002 Science 298:759-1762; Chan et al. (1998) Science 281:2016-2018; U.S. Pat. No. 6,855,551; Bruchez et al. (1998) Science 281: 2013-2016

Suitable fluorescent molecules (fluorophores) include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1'3,3'-tetraethyl-benzimidazoylcarbocyanine iodide), tetrabromorhodamine 123, rhodamine 6G, TMRM (tetramethylrhodamine-, methyl ester), TMRE (tetramethylrhodamine, ethyl ester)$_9$ tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino)naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-1-fluorescein (DTAF), 2',7' dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl)aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes; and the like. Fluorophores of interest are further described in WO 01/42505 and WO 01/86001.

Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP, which is available commercially, e.g., from Clontech, Inc.; a GFP from another species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Suitable epitope tags include, but are not limited to, hemagglutinin (HA; e.g., CYPYDVPDYA; SEQ ID NO:1), FLAG (e.g., DYKDDDDK; SEQ ID NO:2), FLAG-C (e.g., DYKD-DDDKC; SEQ ID NO:3, c-myc (e.g., CEQKLISEEDL; SEQ ID NO:4), a metal ion affinity tag such as a polyhistidine tag (e.g., His$_6$), and the like.

Suitable imaging agents include positive contrast agents and negative contrast agents. Suitable positive contrast agents include, but are not limited to, gadolinium tetraazacyclododecanetetraacetic acid (Gd-DOTA); Gadolinium-diethylenetriaminepentaacetic acid (Gd-DTPA); Gadolinium-1,4,7-tris (carbonylmethyl)-10-(2'-hydroxypropyl)-1,4,7,10-tetra-azacyclododecane (Gd-HP-DO3A); Manganese(II)-dipyridoxal diphosphate (Mn-DPDP); Gd-diethylenetriaminepentaacetate-bis(methylamide) (Gd-DTPA-BMA); and the like. Suitable negative contrast agents include, but are not limited to, a superparamagnetic iron oxide (SPIO) imaging agent; and a perfluorocarbon, where suitable perfluorocarbons include, but are not limited to, fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, perfluorohexanes, perfluoropentanes, perfluorobutanes, perfluoropropanes, sulfur hexafluoride, and the like.

Specific Binding Partners

In another embodiment, a subject modified cycloalkyne comprises a member of a pair of binding partners A member of a pair of binding partners is referred to herein as a "specific binding partner."

Suitable specific binding partners include, but are not limited to, a member of a receptor/ligand pair; a member of an antibody/antigen pair; a member of a lectin/carbohydrate pair; a member of an enzyme/substrate pair; biotin/avidin; biotin/streptavidin; digoxin/antidigoxin; and the like. Suitable specific binding partners include, but are not limited to a receptor ligand; a receptor for a ligand; a ligand-binding portion of a receptor; an antibody; an antigen-binding fragment of an antibody; an antigen; a hapten; a lectin; a lectin-binding carbohydrate; an enzyme substrate; an irreversible inhibitor of an enzyme (e.g., an irreversible inhibitor that binds a substrate binding site of an enzyme, e.g., a "suicide" substrate); and the like.

Suitable ligand members of receptor/ligand pairs include, but are not limited to, neurotransmitters such as opioid compounds, acetylcholine, and the like; viral proteins that bind to a cell surface receptor, e.g., human immunodeficiency virus gp120, and the like; hormones; and the like.

Suitable antigen-binding antibody fragments include F(ab')$_2$, F(ab)$_2$, Fab', Fab, Fv, scFv, and Fd fragments, single-chain antibodies, and fusion proteins comprising an antigen-binding portion of an antibody and a non-antibody protein (e.g., an antigen-binding fragment of an antibody fused to an immunoglobulin constant region).

Suitable haptens include, but are not limited to, (4-hydroxy-3-nitrophenyl) acetyl; diethylenetriaminepentaacetic acid (DTPA) or one of its metal complexes; paranitrophenyl; biotin; fluorescein isothiocyanate; and the like.

Drugs

Suitable drugs that can be attached to a modified cycloalkyne moiety include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like.

Suitable cancer chemotherapeutic compounds include, but are not limited to, non-peptidic (i.e., non-proteinaceous) compounds that reduce proliferation of cancer cells; peptidic compounds that reduce proliferation of cancer cells; antimetabolite agents; cytotoxic agents; and cytostatic agents. Non-limiting examples of chemotherapeutic agents include alkylating agents, nitrosoureas, antimetabolites, antitumor antibiotics, plant (vinca) alkaloids, and steroid hormones.

Suitable agents that act to reduce cellular proliferation include, but are not limited to, alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Suitable antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable anti-proliferative natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other suitable anti-proliferative cytotoxic agents are navelbene, CPT-11, anastrazole, letrazole, capecitabine, reloxafine, cyclophosphamide, ifosamide, and droloxafine.

Suitable microtubule affecting agents that have antiproliferative activity include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Suitable hormone modulators and steroids (including synthetic analogs) include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are also suitable for attachment to a cycloalkyne moiety. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers that are suitable for attachment to a cycloalkyne moiety include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; and (9) inhibitors of angiogenesis.

Linkers

Suitable linkers include, but are not limited to, a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, a nitro, and a peptide linker.

Exemplary peptide linkers for use in linking a molecule of interest to a modified cycloalkyne will in some embodiments have a combination of glycine, alanine, proline and methionine residues, where suitable peptide linkers include, but are not limited to AAAGGM (SEQ ID NO:5); AAAGGMPPAAAGGM (SEQ ID NO:6); AAAGGM (SEQ ID NO:7); and PPAAAGGMM (SEQ ID NO:8). In some embodiments, a peptide linker will comprise multiple serine residues, e.g., from 50% to 75%, or from 75% to 100% of the amino acids in the linker are serine residues. In other embodiments, a peptide linker will comprise multiple glycine residues, e.g., from 50% to 75%, or from 75% to 100% of the amino acids in the linker are glycine residues. Any flexible linker, generally having a length of from about 6 amino acids and about 40 amino acids is suitable for use. Linkers may have virtually any sequence that results in a generally flexible peptide, including alanine-proline rich sequences.

Compositions

The present invention further provides compositions, including pharmaceutical compositions, comprising a subject modified cycloalkyne compound. A subject composition generally comprises a subject modified cycloalkyne compound; and at least one additional compound. Suitable additional compounds include, but are not limited to: a salt, such as a magnesium salt, a sodium salt, etc., e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a subject composition comprises a subject modified cycloalkyne compound; and a pharmaceutically acceptable excipient. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Modifying a Target Biomolecule

The present invention provides methods for chemoselective modification of a target molecule comprising an azide. The methods generally involve reacting an azide in an azide-containing target molecule with a modified cycloalkyne. The modified cycloalkyne has a structure as described above. Thus, in many embodiments, a subject method for synthetically modifying a cellular component generally involves: a) introducing an azide moiety into a cellular component, thereby generating an azide-modified cellular component; and contacting the cell comprising the azide-modified cellular component with a reactive partner comprising a modified cycloalkyne, the contacting being under physiological conditions. The contacting step results in reaction between the azide group of azide-modified cellular component and the cycloalkyne of the reactive partner, thereby synthetically and covalently modifying the cellular component. In some embodiments, the method is carried out on living cells in vitro. In other embodiments, the method is carried out on living cells ex vivo. In still other embodiments, the method is carried out on living cells in vivo.

In one embodiment, the chemoselective ligation is designed for use in fully aqueous, physiological conditions and involves production of a stable, final product comprising a fused azide/cycloalkyne ring. In general, this embodiment involves reacting a first reactant comprising a strained cycloalkyne moiety with a second reactant comprising an azide, such that a covalent bond is formed between the first and second reactants by reaction of the strained cycloalkyne moiety with the azide group.

First Reactant

A first reactant comprises a strained cycloalkyne moiety that provides the energy for the reaction between the first and second reactants. The first reactant is a modified cycloalkyne compound of the formula:

where:

X is a cycloalkyne group substituted with $R_1$;

Y is H; a moiety that comprises a reactive group that facilitates covalent attachment of a molecule of interest; or a molecule of interest;

$R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro. In some embodiments, the first reactant is a modified cycloalkyne compound of any of Formulas I-XXII, as described above.

Exemplary reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, thiol, succinimidyl ester, isothiocyanate, iodoacetamide, maleimide, hydrazine, and the like. Exemplary molecules of interest further include dyes (e.g., fluorescein or modified fluorescein, and the like), toxins (including cytotoxins), linkers, peptides, and the like.

The molecule of interest may be reacted directly with the reactive group or through a linker. Exemplary molecules of interest include, but are not necessarily limited to, a detectable label, a drug, a peptide, a member of a specific binding pair, and the like. Such molecules of interest are described in more detail above.

In some embodiments, Y is a reactive group selected from a carboxyl, an amine, an ester, a thioester, a sulfonyl halide, an alcohol, a thiol, a succinimidyl ester, an isothiocyanate, an iodoacetamide, a maleimide, and a hydrazine.

In some embodiments, the cycloalkyne is a cyclooctyne.

In some embodiments, the modified cycloalkyne is of Formula I:

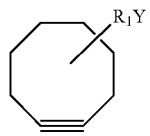

Formula I where

Y is H; a moiety that comprises a reactive group that facilitates covalent attachment of a molecule of interest; or a molecule of interest;

$R_1$ is selected from a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro.

In other embodiments, the modified cycloalkyne is of any of Formulas II-XXII, above.

Second Reactant

The second reactant is a compound that comprises an azide such that a covalent bond is formed between the first and second reactants by reaction of the cycloalkyne moiety with the azide group. In general, the second reactant is of the formula:

where $R_2$ is a target molecule, e.g., a biomolecule or other target molecule.

Target Molecules

Molecules comprising an azide and suitable for use in the present invention, as well as methods for producing azide-comprising molecules suitable for use in the present invention, are well known in the art. Target molecules of particular interest as the second reactant include, but are not necessarily limited to, amino acids and amino acid residues, polypeptides (including peptides and proteins), sugars or sugar residues, and the like, which contain or are modified to contain at least one azide.

The target molecules can be naturally occurring, or may be synthetically or recombinantly produced, and may be isolated, substantially purified, or present within the native milieu of the unmodified molecule upon which the azide-containing target molecule is based (e.g., on a cell surface or within a cell, including within a host animal, e.g., a mammalian animal, such as a murine host (e.g., rat, mouse), hamster, canine, feline, bovine, swine, and the like). In some embodiments, the target molecule is present in vitro in a cell-free reaction. In other embodiments, the target molecule is present in a cell and/or displayed on the surface of a cell. In many embodiments of interest, the target molecule is in a living cell; on the surface of a living cell; in a living organism, e.g., in a living multicellular organism. Suitable living cells include cells that are part of a living multicellular organism; cells isolated from a multicellular organism; immortalized cell lines; and the like.

Where the target molecule is a polypeptide, the polypeptide may be composed of D-amino acids, L-amino acids, or both, and may be further modified, either naturally, synthetically, or recombinantly, to include other moieties. For example, the target polypeptide may be a lipoprotein, a glycoprotein, or other such modified protein.

In general, the target molecule useful as the second reactant comprises at least one azide for reaction with modified cycloalkyne according to the invention, but may comprise 2 or more, 3 or more, 5 or more, 10 or more azides. The number of azides that may be present in a target molecule will vary according to the intended application of the final product of the reaction, the nature of the target molecule itself, and other considerations which will be readily apparent to the ordinarily skilled artisan in practicing the invention as disclosed herein.

This embodiment of the invention is particularly useful in modification of a target molecule in vivo. In this embodiment, the target substrate is modified to comprise an azide group at the point at which linkage to the modified cycloalkyne reactant is desired. For example, where the target substrate is a polypeptide, the polypeptide is modified to contain an N-terminal azide. Where the target substrate is a glycoprotein, a sugar residue of the glycoprotein can be modified to contain an azide. A target molecule that is unmodified with an azide, but that is to be modified with an azide, is referred to herein as a "target substrate." A target molecule that is modified with an azide is referred to herein as "an azide-modified target molecule" or "an azide-containing target molecule."

Azide Modification of a Target Molecule

The target substrate can be generated in vitro and then introduced into the cell using any of a variety of methods well known in the art (e.g., microinjection, liposome or lipofectin-mediated delivery, electroporation, etc.), which methods will vary according to the nature of the substrate to be targeted for modification and can be readily and appropriately selected by the ordinarily skilled artisan. The final target substrate can also be generated in vivo by exploiting a host cell's natural biosynthetic machinery. For example, the cell can be provided with a biocompatible azide-derivative of a substrate for synthesis of the desired target molecule, which substrate is processed by the cell to provide an azide-derivative of the desired final target substrate. For example, where the target substrate is a cell surface glycoprotein, the cell can be provided with an azide derivative of a sugar residue found within the glycoprotein, which is subsequently processed by the cell through natural biosynthetic processes to produce a modified glycoprotein having at least one modified sugar moiety comprising an accessible azide group.

The target substrate can also be produced in vivo using methods well known in the art. For example, unnatural amino acids having azides can be incorporated into recombinant polypeptides expressed in E. coli (see, e.g., Kiick et al. (2000) Tetrahedron 56:9487). Such recombinantly produced polypeptides can be selectively reacted with a modified cycloalkyne reagent according to the invention.

In one example, an azide group is incorporated into the target molecule by providing a cell (e.g., a eukaryotic cell that glycosylates biopolymers such as proteins) with a synthetic building block for the desired biopolymer target substrate.

For example, the cell can be provided with a sugar molecule comprising an azide group to provide for incorporation of the azide group in a glycoprotein. In some embodiments, the glycoprotein is expressed on the cell surface. Alternatively, the azide group can be incorporated into an amino acid, which is subsequently incorporated into a peptide or polypeptide synthesized by the cell. Several methods are available for incorporating unnatural building blocks into biopolymers; one need not be restricted to cell surface oligosaccharides as target molecules. See, e.g., vanHest et al. (1998) *FEBS Lett.* 428:68; and Nowak et al. (1995) *Science* 268:439.

In one embodiment, the target molecule is a carbohydrate-containing molecule (e.g., a glycoprotein; a polysaccharide; etc.), and an azide group is introduced into the target molecule using a synthetic substrate. In some embodiments, the synthetic substrate is an azide derivative of a sugar utilized in production of a glycosylated molecule. In some embodiments, the synthetic substrate is an azide derivative of a sugar utilized in production of a cell surface molecule, e.g., in the glycoprotein biosynthetic pathway. For example, the host cell can be provided with a synthetic sialic acid azido-derivative, which is incorporated into the pathway for sialic acid biosynthesis, eventually resulting in the incorporation of the synthetic sugar residue in glycoproteins. In some embodiments, the glycoproteins are displayed on the cell surface.

In one example, the synthetic substrate is an azido derivative of mannosamine of the general formula:

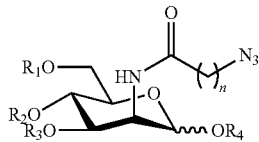

where n is from 1 to 6, generally from 1 to 4, more usually 1 to 2, and $R_1$, $R_2$, $R_3$, and $R_4$ are independently hydrogen or acetyl. In some embodiments, the substrate is N-azidoacetyl-mannosamine (n=1) or an acetylated derivative thereof, or N-azidopropanoylmannosamine (n=2) or an acetylated form thereof.

In another embodiment, the synthetic substrate is an azido sugar derivative of a general formula of, for example:

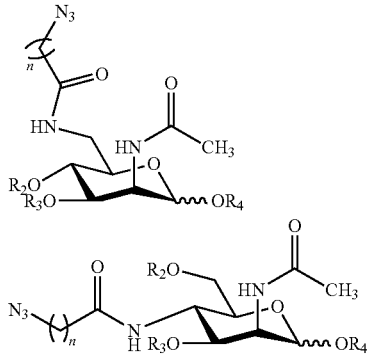

either of which can be incorporated into the sialic acid biosynthesis pathway, and where n is from 1 to 6, generally from 1 to 4, more usually 1 to 2, and $R_2$, $R_3$, and $R_4$ are independently hydrogen or acetyl.

In another embodiment, the synthetic substrate is an azido sugar derivative of a general formula of, for example:

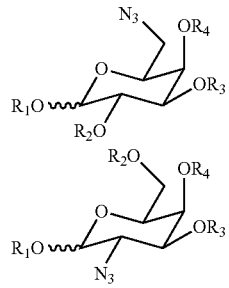

where $R_1$, $R_2$, $R_3$, and $R_4$ are independently hydrogen or acetyl, and where the synthetic substrate is incorporated into biosynthetic pathways involving fucose.

In another embodiment, the synthetic substrate is an azido sugar derivative of a general formula of, for example:

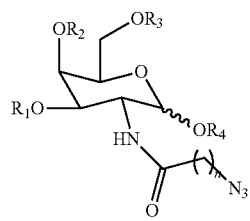

where n is from 1 to 6, generally from 1 to 4, more usually 1 to 2, and $R_1$, $R_2$, $R_3$, and $R_4$ are independently hydrogen or acetyl, and which is incorporated into biosynthetic pathways involving galactose.

Cell Surface Modification

In some embodiments, a subject method is used to modify the surface of a cell. Thus, in one aspect, the invention features a method of modifying the surface of cell in vitro or in vivo. The method generally involves reacting an azide group in a target molecule that comprises an azide group with a modified cycloalkyne to provide for chemoselective ligation at the cell surface. In many embodiments, the method comprises modifying a target molecule on a cell surface with an azide group; and reacting the azide group in the target molecule with a modified cycloalkyne. For example, as described above, an azido sugar is provided to a living cell, which azido sugar is incorporated into a glycoprotein that is displayed on the cell surface.

Modification of an Azide-Modified Target Molecule with Detectable Labels, Drugs, and Other Molecules In some embodiments, the present invention provides for attachment of a molecule of interest, e.g., a functional molecule, to an azide-modified target molecule. The methods generally involve reacting an azide-modified target molecule with a subject modified cycloalkyne, where the modified cycloalkyne comprises a molecule of interest, as described above. As described above, molecules of interest include, but are not limited to, a detectable label; a toxin (including cytotoxins); a linker; a peptide; a drug; a member of a specific binding pair; an epitope tag; and the like.

Attachment of Target Molecules to a Support

The modified cycloalkyne can also comprise one or more hydrocarbon linkers (e.g., an alkyl group or derivative thereof such as an alkyl ester) conjugated to a moiety providing for attachment to a solid substratum (e.g., to facilitate assays), or to a moiety providing for easy separation (e.g., a hapten recognized by an antibody bound to a magnetic bead). In one embodiment, the methods of the invention are used to provide for attachment of a protein (or other molecule that contains or can be modified to contain an azide) to a chip in a defined orientation. For example, a polypeptide having an azide at a selected site (e.g., at or near the N-terminus) can be generated, and the methods and compositions of the invention used to deliver a tag or other moiety to the azide of the polypeptide. The tag or other moiety can then be used as the attachment site for affixing the polypeptide to a support (e.g., solid or semi-solid support, particular a support suitable for use as a microchip in high-throughput assays).

Attachment of Molecules for Delivery to a Target Site

The modified cycloalkyne will in some embodiments comprise a small molecule drug, toxin, or other molecule for delivery to a cell. The small molecule drug, toxin, or other molecule will in some embodiments provide for a pharmacological activity. The small molecule drug, toxin, or other molecule will in some embodiments serve as a target for delivery of other molecules.

Small molecule drugs may be small organic or inorganic compounds having a molecular weight of more than 50 and less than about 2,500 daltons. Small molecule drugs may comprise functional groups necessary for structural interaction with proteins, particularly hydrogen bonding, and may include at least an amine, carbonyl, hydroxyl or carboxyl group, and may contain at least two of the functional chemical groups. The drugs may comprise cyclical carbon or heterocyclic structures and/or aromatic or polyaromatic structures substituted with one or more of the above functional groups. Small molecule drugs are also found among biomolecules including peptides, saccharides, fatty acids, steroids, purines, pyrimidines, derivatives, structural analogs or combinations thereof.

In another embodiment, a subject modified cycloalkyne comprises one of a pair of binding partners (e.g., a ligand; a ligand-binding portion of a receptor; an antibody; an antigen-binding fragment of an antibody; an antigen; a hapten; a lectin; a lectin-binding carbohydrate; etc.). For example, the modified cycloalkyne can comprise a polypeptide that serves as a viral receptor and, upon binding with a viral envelope protein or viral capsid protein, facilitates attachment of virus to the cell surface on which the modified cycloalkyne is displayed. Alternatively, the modified cycloalkyne comprises an antigen that is specifically bound by an antibody (e.g., monoclonal antibody), to facilitate detection and/or separation of host cells displaying the antigen on the cell surface. In another example, the modified cycloalkyne comprises a ligand binding portion of a receptor, or a receptor-binding portion of a ligand.

Utility

Subject modified cycloalkyne compounds, and subject modification methods, are useful in a variety of applications, including research applications and diagnostic applications.

Research Applications

In some embodiments, subject modified cycloalkyne compounds, and subject modification methods, are useful in research applications. Applications of interest include research applications, e.g., exploring functional and physical characteristics of a receptor; proteomics; metabolomics; and the like. Research applications also include drug discovery or other screening applications.

Proteomics aims to detect, identify, and quantify proteins to obtain biologically relevant information. Metabolomics is the detection, identification, and quantification of metabolites and other small molecules such as lipids and carbohydrates. Fiehn (2001) *Comparative and Functional Genomics* 2:155-168; and U.S. Pat. No. 6,873,914.

Drug discovery applications include, but are not limited to, identifying agents that inhibit cancer cell viability and/or growth. Thus, in some embodiments, the instant invention provides methods of identifying an agent that inhibits cancer cell viability and/or growth. The methods generally involve modifying a component of the cell to comprise a first reactive partner comprising an azide; contacting the cell, in the presence of a test agent, with a second reactive partner comprising a modified cycloalkyne, the contacting being under physiological conditions; where the contacting results in reaction between the azide group of the first reactive partner and the cycloalkyne of the second reactive partner, thereby synthetically and covalently modifying the cellular component; and determining the effect, if any, of the test agent on the level of modification of the cell with the second reactive partner.

Where the cancer cell is one that produces a higher amount of a carbohydrate than a normal (non-cancerous) cell of the same cell type, the method provides for identifying an agent that reduces growth and/or viability of the cancerous cell.

Diagnostic and Therapeutic Applications

Applications of interest also include diagnostic applications, e.g., for detection of cancer; and the like, where a subject modified cycloalkyne comprising a detectable label is used to label an azide-modified target molecule, e.g., an azide-labeled target molecule present on a cancer cell. Applications of interest also include therapeutic applications, where a drug or other therapeutic agent is delivered to an azide-modified target molecule, using a subject modified cycloalkyne that comprises a covalently linked drug or other therapeutic agent.

In some embodiments, the present invention is used for in vivo imaging, e.g., to determine the metabolic or other state of a cell in an organism, e.g., an individual. As one non-limiting example, a subject method can be applied to in vivo imaging of cancer cells in an individual (e.g., a mammal, including rodents, lagomorphs, felines, canines, equines, bovines, ovines, caprines, non-human primates, and humans).

One exemplary, non-limiting application of a subject azide-alkyne cycloaddition is in the detection of metabolic change in cells that occur as they alter their phenotype. As one example, altered glycosylation patterns are a hallmark of the tumor phenotype, consisting of both the under- and over-expression of naturally-occurring glycans as well as the presentation of glycans normally restricted to expression during embryonic development. Examples of common antigens associated with transformed cells are sialyl Lewis a, sialyl Lewis x, sialyl T, sialyl Tn, and polysialic acid (PSA). Jorgensen et al. (1995) Cancer Res. 55, 1817-1819; Sell (1990) Hum. Pathology 21, 1003-1019; Taki et al. (1988) J. Biochem. 103, 998-1003; Gabius (1988) Angew. Chem. Int. Ed. Engl. 27, 1267-1276; Feizi (1991) Trends Biochem. Sci. 16, 84-86; Taylor-Papadimitriou and Epenetos (1994) Trends Biotech. 12, 227-233; Hakomori and Zhang (1997) Chem. Biol. 4, 97-104; Dohi et al. (1994) Cancer 73, 1552. These antigens share an important feature—they each contain terminal sialic acid. PSA is a homopolymer of sialic acid residues up to 50 units in length. Elevated levels of sialic acid are highly correlated with the transformed phenotype in many cancers, including gastric (Dohi et al. (1994) Cancer 73, 1552; and Yamashita et al. (1995) J. Natl. Cancer Inst. 87, 441-446), colon (Yamashita et al. (1995) J. Natl. Cancer Inst. 87, 441-446; Hanski et al. (1995) Cancer Res. 55, 928-933; Hanski et al. (1993) Cancer Res. 53, 4082-4088; Yang et al. (1994) Glycobiology 4, 873-884; Saitoh et al. (1992) J. Biol. Chem. 267, 5700-5711), pancreatic (Sawada et al. (1994) Int. J. Cancer 57, 901-907), liver (Sawada et al. (1994) J. Biol. Chem. 269, 1425-1431), lung (Weibel et al. (1988) Cancer Res. 48, 4318-4323), prostate (Jorgensen et al. (1995) Cancer Res. 55, 1817-1819), kidney (Roth et al. (1988) Proc. Natl. Acad. Sci. USA 85, 2999-3000), and breast cancers (Cho et al. (1994) Cancer Res. 54, 6302-6305), as well as several types of leukemia (Joshi et al. (1987) Cancer Res. 47, 3551-3557; Altevogt et al. (1983) Cancer Res. 43, 5138-5144; Okada et al. (1994) Cancer 73, 1811-1816). A strong correlation between the level of cell surface sialic acid and metastatic potential has also been observed in several different tumor types (Kakeji et al. (1995) Brit. J. Cancer 71, 191-195; Takano et al. (1994) Glycobiology 4, 665-674). The collective display of multiple sialylated antigens on a single cancer cell can account for the fact that so many different tumor types share the high sialic acid phenotype without necessarily expressing an identical complement of antigens (Roth et al. (1988) supra). Consequently, diagnostic or therapeutic strategies that target cells on the basis of sialic acid levels have broad applicability to many cancers.

Introduction and incorporation of unnatural azidosugars (ManNAz, GalNAz) into living animals provides for detection of changes in metabolic state. Via the attachment of the appropriate epitope tag, the modified cyclooctyne labels these cells in a living organism, and consequently detects changes in metabolic state. Early detection of tumorigenic cells and subsequent intervention reduces the severity and increases survival rates for cancer patients.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Modification of Biomolecules Using a Modified Cyclooctyne

Materials and Methods

All chemical reagents were purchased from Aldrich and used without further purification. All solvents were distilled under a $N_2$ atmosphere. $CH_2Cl_2$, toluene, and pyridine were dried over $CaH_2$. Thin layer chromatography was carried out on Analtech Uniplate® silica gel plates. Flash chromatography was performed using Merck 60 Å 230-400 mesh silica gel. All $^1H$ and $^{13}C$ NMR spectra were acquired on Bruker AVB-400® or DRX-500® as noted. $^1H$ chemical shifts are reported as δ referenced to solvent and coupling constants (J) are reported in Hz. Compounds 1 and 4 have been previously reported. Skattebol and Solomon (1973) *Organic Syntheses* 5/Coll. Volumes:306-310; and Wilbur et al. (1996) *Bioconj. Chem.* 7:689-702.

RPMI 1640 media and phosphate-buffered saline (PBS) were purchased from Invitrogen Life Technologies. Fetal calf serum (FCS) was from Hyclone. FITC-conjugated avidin and bovine serum albumin (BSA) were purchased from Sigma, and peroxidase-conjugated mouse anti-biotin (HRP-α-biotin) and peroxidase-conjugated donkey anti-human Ig (HRP-α-Ig) were from Jackson ImmunoResearch Laboratories, Inc. Precast Tris.HCl 4-15% polyacrylamide gels, nitrocellulose, and Tween 20 (non-ionic detergent) were purchased from BioRad. Restore™ Western blot stripping buffer and enhanced chemiluminescent substrate were obtained from Pierce. For cell-labeling experiments, a Coulter Z2 cell counter was used to determine cell densities. Flow cytometry data were acquired on a BD Biosciences FACSCalibur flow cytometer equipped with a 488-nm argon laser, and live cells were analyzed as determined by granularity and size. For all flow cytometry experiments, data points were collected in triplicate.

Synthesis of Compounds:

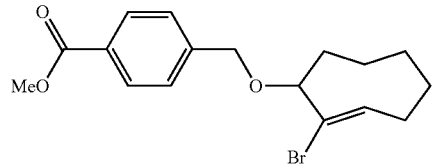

Compound 2

Compound 2.

AgClO$_4$ (1.16 g, 5.61 mmol) was added to a solution of compound 1 (500 mg, 1.87 mmol) and methyl 4-hydroxymethylbenzoate (4.66 g, 28.1 mmol) dissolved in toluene (8 mL) in a flame-dried, aluminum-foil-wrapped flask. The reaction was stirred for 2 h, diluted with pentane (20 mL), and filtered to remove insoluble silver salts. The solution was concentrated and purified by silica gel chromatography (4-8% EtOAc: pet ether; R$_f$ (8% EtOAc: pet ether)=0.32) to yield 2 as a colorless oil (660 mg 1.86 mmol, 99%). $^1H$ NMR (500 MHz, CDCl$_3$) δ 8.02 (d, 2H, J=8.0 Hz), 7.47 (d, 2H, J=8.0 Hz), 6.21 (dd, 1H, J=4.0, 11.5 Hz), 4.72 (d, 1H, J=12.5 Hz), 4.39 (d, 1H, J=12.5 Hz), 3.95-3.91 (m, 4H), 2.81 (app dq, 1H, J=5.5, 12.0), 2.32 (m, 1H), 2.05-1.88 (m, 4H), 1.75 (m, 1H), 1.49 (app dq, 1H, J=5.0, 8.0), 1.35 (m, 1H), 0.79 (m, 1H); $^{13}C$ NMR (125 MHz, CDCl$_3$) δ 166.93, 143.20, 132.60, 132.09, 129.66, 129.34, 127.65, 84.22, 69.61, 52.04, 39.48, 36.46, 33.31, 28.09, 26.29; IR (cm$^{-1}$) 2931, 2856, 1724, 1614, 1434, 1279, 1109; FAB HRMS calcd. for C$_{17}$H$_{23}$O$_3$Br [M+H]$^+$ 353.0752. found 353.0744.

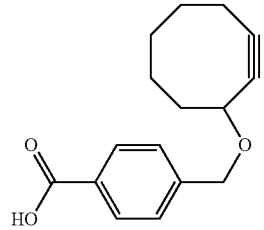

Compound 3

Compound 3.

A suspension of NaOMe (119 mg, 2.20 mmol) in anhydrous DMSO (8 mL) was added to compound 2 (650 mg, 1.84 mmol) dissolved in anhydrous DMSO (16 mL). The reaction was stirred 20 min and additional NaOMe (110 mg, 1.10 mmol in 1.5 mL of DMSO) was added. The reaction was stirred until the starting material was completely consumed as determined by TLC (20 min). The reaction was acidified with 1 M HCl (100 mL) and extracted twice with EtOAc (40 mL). The combined organic layers were washed with brine (40 mL) and concentrated. The resulting film was dissolved in 20% H$_2$O/dioxane (15 mL), LiOH (220 mg, 9.0 mmol) was added, and the reaction was stirred for 24 h. The reaction was acidified with 1 M HCl (100 mL) and extracted twice with EtOAc (40 mL). The combined organic extracts were dried over MgSO$_4$, filtered, and purified by silica gel chromatography (10:90:1 EtOAc:pet ether: AcOH −25:75:1 EtOAc:pet ether: AcOH; R$_f$ (25:75:1)=0.38) to yield 3 (350 mg, 1.36 mmol, 74%) as a white solid. $^1$H NMR (500 MHz, CDCl$_3$) δ 8.09 (d, 1H, J=8.50 Hz), 7.47 (d, 1H, J=8.0 Hz), 4.77 (d, 1H, J=12.5 Hz), 4.49 (d, 1H, J=13 Hz), 4.26 (m, 1H), 2.32-2.26 (m, 1H), 2.22-2.13 (m, 2H), 2.08-2.03 (m, 1H), 1.97-1.92 (m, 1H), 1.89-1.83 (m, 2H), 1.73-1.62 (m, 2H) 1.52-1.44 (m, 1H); $^{13}$C NMR (125 MHz, CDCl$_3$) δ 171.52, 144.50, 130.27, 128.29, 127.46, 100.69, 92.40, 72.11, 70.39, 42.31, 34.26, 29.68, 26.31, 20.70; IR (cm$^{-1}$) 2924, 2852, 2672, 2561, 1685, 1429, 1323, 1294, 1086; FAB HRMS calcd. for C$_{16}$H$_{18}$O$_3$Li [M+Li]$^+$ 265.1416. found 265.1422.

4.29-4.26 (m, 2H), 3.62-3.56 (m, 8H), 3.52-3.49 (m, 2H), 3.47-3.42 (m, 4H), 3.22-3.13 (m, 3H), 2.91-2.87 (m, 2H), 2.66 (d, 1H, J=12.8 Hz), 2.32-2.19 (m, 6H), 1.89-1.79 (m, 4H), 1.75-1.34 (m, 10H); $^{13}$C NMR (125 MHz, CD$_3$CN) −172.64, 166.56, 162.93, 141.82, 134.15, 127.47, 127.05, 100.31, 92.63, 71.94, 70.12, 69.94, 69.83, 69.16, 68.75, 61.37, 59.80, 55.36, 42.14, 40.18, 37.53, 36.56, 35.45, 34.12, 29.56, 29.32, 29.26, 28.02, 27.98, 26.18, 25.46, 20.13; FAB HRMS calcd. for C$_{36}$H$_{55}$N$_4$O$_7$S [M+H]$^+$ 687.3791. found 687.3798.

Compound 6

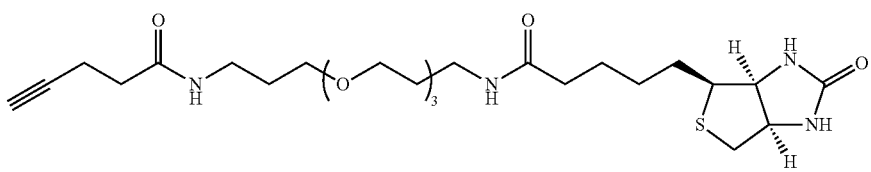

Compound 6.

Compound 4 (46 mg, 0.10 mmol), pentynoic acid (15 mg, 0.15 mmol) and HATU (59 mg, 0.15 mmol) were dissolved in anhydrous DMF (1 mL). Triethyl amine (22 μL, 0.15 mmol) was added to the solution and the reaction was stirred for 14 h. Purification by silica gel chromatography (15:2:1 EtOAc: MeOH:H$_2$O to 9:2:1 EtOAc:MeOH:H$_2$O R$_f$ (9:2:1)=0.30) yielded 6 (25 mg, 0.047 mmol, 46%) as a yellow oil. $^1$H NMR (400 MHz, CD$_3$CN) δ 6.77 (br s, 2H), 5.74 (s, 1H), 5.38 (s, 1H), 4.44 (app t, 1H, J=7.6 Hz), 4.27 (m, 1H), 3.61-3.54 (m, 8H), 3.51 (t, 4H, J=6.4 Hz), 3.25-3.16 (m, 5H), 2.91 (dd, 1H, J=4.8, 12.4 Hz), 2.68 (d, 1H, J=12.8 Hz), 2.47 (m, 2H), 2.35-2.30 (m, 6H), 2.22 (t, 1H, J=2.8 Hz), 2.17 (t, 2H, J=7.2 Hz), 1.75-1.53 (m, 8H), 1.44-1.37 (m, 2H); $^{13}$C NMR (100 MHz, CD$_3$CN) δ 172.79, 170.74, 163.21, 83.53, 70.10, 69.82, 69.10, 68.71, 68.60, 61.46, 59.87, 55.41, 40.18, 36.49, 35.47, 34.69, 29.32, 29.29, 28.07, 28.01, 25.48, 14.32; FAB LRMS calcd. for C$_{25}$H$_{43}$N$_4$O$_6$S [M+H]$^+$ 527.4. found 527.4.

Western Blot Analysis of an Azide-Labeled GlyCAM-Ig

For Western blot analysis of azide-labeled and unlabeled GlyCAM-Ig, samples were incubated with 5 (250 μM final concentration in PBS, pH 7.4 containing 0.7% DMF), 6 (250 μM final concentration in PBS, pH 7.4 containing either 0.7% DMF) or left untreated for 12 h. To verify that 6 could react with azide-labeled GlyCAM-Ig via copper-mediated [3+2] cycloaddition, a modified version of the method reported by Speers and Cravatt was employed. Speers and Cravatt (2004) *Chem. Biol.* 11:535-46. Briefly, GlyCAM-Ig samples (in PBS, pH 7.4 containing 0.7% DMF) were incubated with 250 μM 6, 2.5 mM TCEP, 250 μM tris-triazolyl ligand (from a 1.7 mM stock in 1:4 DMSO:tert-butanol), and 2.5 mM CuSO$_4$. Samples were vortexed and allowed to react at rt for 12 h. Prior to electrophoresis, samples were incubated with an equal volume of 100 mM 2-azidoethanol in 2×SDS-PAGE loading buffer for 8 h at rt (to quench unreacted 5 or 6). The quenched samples were boiled for 3 min and loaded onto precast polyacrylamide gels. After electrophoresis, the samples were electroblotted to nitrocellulose membrane. The membrane was blocked using 5% BSA in PBS (pH 7.4, containing 0.05% Tween 20 (blocking buffer A) for 1 h at rt, then incubated with a solution of blocking buffer A containing HRP-α-biotin (1:250,000 dilution, 1 h at rt). The membrane was washed, and detection of membrane-bound anti-biotin-HRP was accomplished by chemiluminescence. Following detection, the membrane was rinsed with PBS (pH 7.4) containing 0.05% Tween (PBS-T) and placed in stripping buffer (15 min at RT) to remove bound anti-biotin Ig. The membrane was thoroughly rinsed with PBS-T and probed for residual anti-biotin signal by chemiluminescence.

Compound 5

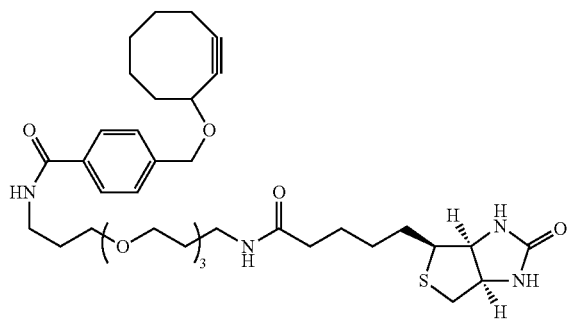

Compound 5.

Pentafluorophenyl trifluoroacetate (Pfp-TFA) (40 μL, 0.23 mmol) was added to compound 3 in anhydrous pyridine (1 mL). The reaction was stirred for 4 h, diluted with CH$_2$Cl$_2$ (30 mL), and extracted with 1 M HCl (3×20 mL) and sat. NaHCO$_3$ solution (2×20 mL). The organic layer was dried over MgSO$_4$, filtered, and concentrated. The crude ester was dissolved in CH$_2$Cl$_2$ (2 mL). Triethylamine (67 μL, 0.46 mmol) and compound 4 (104 mg 0.23 mmol) were added and the solution was stirred for 1 h. The solution was concentrated and crude product purified by silica gel chromatography (80: 15:5 EtOAc:MeOH:H$_2$O, R$_f$=0.40) to yield 5 (68 mg, 0.099 mmol, 51%) as a clear oil. $^1$H NMR (400 MHz, CD$_3$CN) δ 7.80 (d, 2H, J=8.4 Hz), 7.42 (m, 3H), 6.62 (br s, 1H), 5.51 (s, 1H), 5.19 (s, 1H), 4.66 (d, 1H, J=12.0 Hz), 4.45-4.40 (m, 2H), The membrane was washed and re-blocked with 5% low-fat dry powdered milk (blocking buffer B) for 1 h at rt. The membrane was then incubated with HRP-α-Ig (1:5000 in blocking buffer B) for 1 h at rt. The membrane was washed again with PBS-T, and detection of membrane bound anti-human Ig was accomplished as for peroxidase-conjugated anti-biotin. Control samples were treated in an identical manner, except that specific reagents were replaced by buffer where appropriate.

Cell Culture Conditions

Jurkat cells (human T-cell lymphoma) were maintained in a 5% $CO_2$, water-saturated atmosphere and grown in RPMI-1640 media supplemented with 10% FCS, penicillin (100 units/mL) and streptomycin (0.1 mg/mL). Cell densities were maintained between $1\times10^5$ and $1.6\times10^6$ cells/mL for all experiments.

Cell Surface Azide Labeling and Detection

Jurkat cells were seeded at a density of $1.5-2.0\times10^5$ cells/mL and incubated for 3 d in untreated media or media containing various concentrations of $Ac_4ManNAz$. After growth in the presence of $Ac_4ManNAz$, cells were distributed into a 96-well V-bottom tissue culture plate. The cells were pelleted (3500 rpm, 3 min) and washed twice with 200 µL of labeling buffer (PBS, pH 7.4 containing 1% FCS). Cells were then incubated with 5 or a biotinylated phosphine probe (Vocadlo et al. (2003) *Proc. Natl. Acad. Sci. U.S.A.* 100:9116-21) in labeling buffer containing 2.8% DMF or labeling buffer plus 2.8% DMF alone. After incubation, cells were pelleted, washed twice with labeling buffer and resuspended in the same buffer containing FITC-avidin (1:500 dilution of the Sigma stock). Following a 10-min incubation on ice (in the dark), cells were washed with 200 µL of cold labeling buffer and the FITC-avidin staining procedure was repeated. The cells were washed twice with cold labeling buffer, then diluted to a volume of 400 µL for flow cytometry analysis.

Results

Biotinylated cyclooctyne 5 as synthesized as shown in Scheme 1.

Construction of the substituted cyclooctyne core was achieved essentially as described

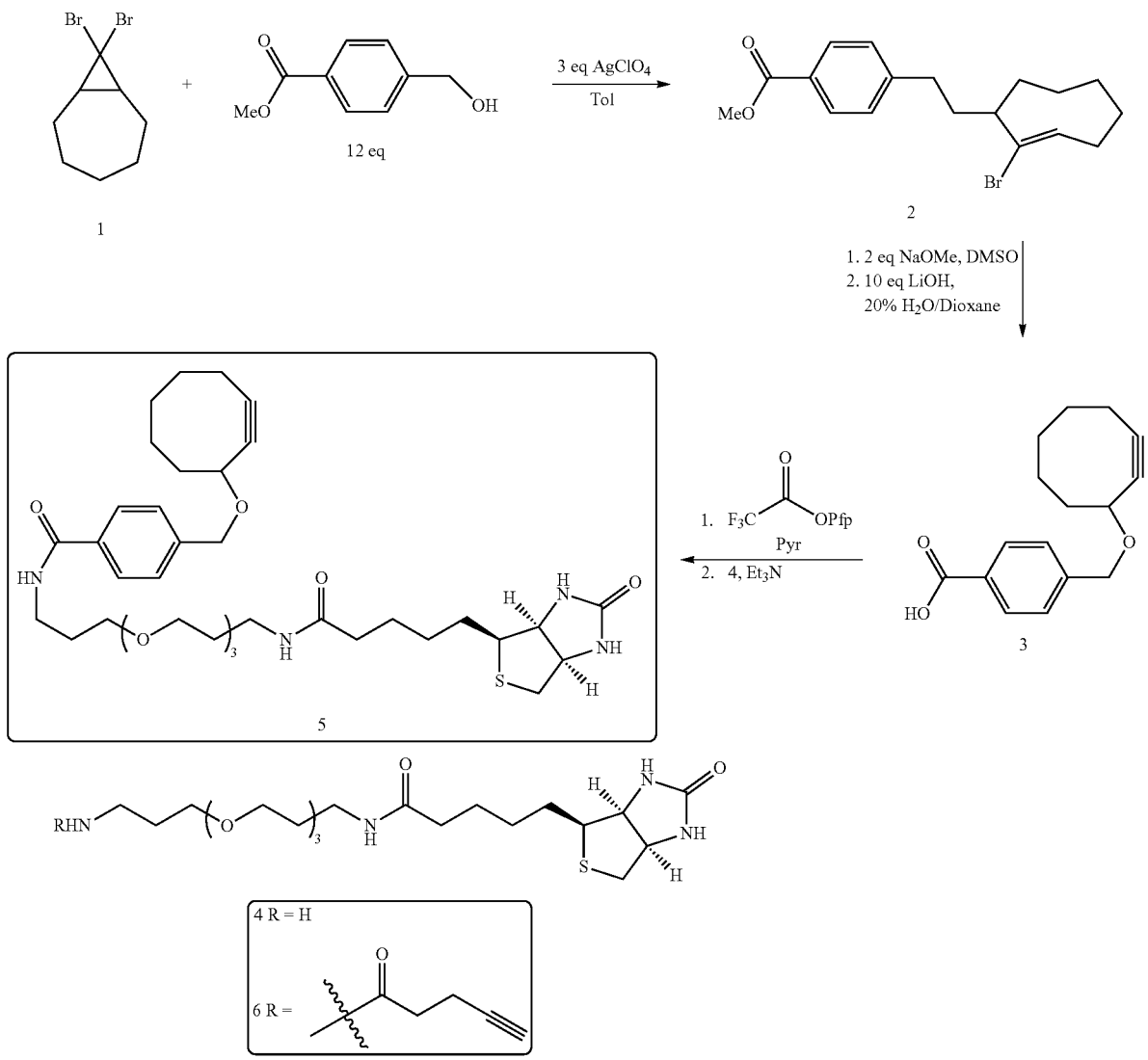

Scheme 1 by Reese and Shaw. Reese and Shaw (1970) *Chem. Comm.* 1172-1173. Briefly, compound 1 (Skattebol and Solomon, supra) was treated with silver perchlorate to effect electrocyclic ring opening to the trans-allylic cation, which was captured with methyl hydroxymethylbenzoate to afford bromo-trans-cyclooctene 2. Base-mediated elimination of the vinyl bromide followed by saponification yielded versatile intermediate 3, to which any biological probe can be attached. Finally, compound 3 was coupled to biotin analog 4 (Wilbur et al. (1996) *Bioconj. Chem.* 7:689-702) bearing a PEG linker, providing target 5. Cyclooctyne 3 was stable to mild acid (0.5 N HCl for 30 min), base (0.8 M NaOMe for 30 min), and prolonged exposure to biological nucleophiles such as thiols (120 mM 2-mercaptoethanol for 12 h).

Figure 2:
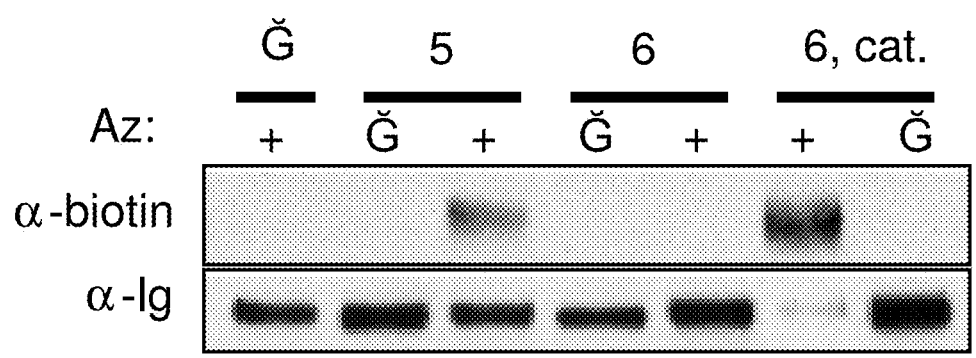
FIG. 2 depicts labeling of azide-modified GlyCAM-Ig with alkyne probes.

Model reactions were performed with compound 3 and 2-azidoethanol, benzylazide or N-butyl α-azidoacetamide. In all cases, the only products observed were the two regioisomeric triazoles formed in approximately equal amounts. The reaction was then applied for covalent labeling of biomolecules. The recombinant glycoprotein GlyCAM-Ig (Bistrup et al. (1999) *J. Cell Biol.* 145:899-910) was expressed in CHO cells in the presence of peracetylated N-azidoacetylmannosamine (Ac$_4$ManNAz), leading to metabolic incorporation of the corresponding N-azidoacetyl sialic acid (SiaNAz) into its glycans. Control samples of GlyCAM-Ig were expressed in the absence of azido sugar. The purified GlyCAM-Ig samples were incubated with 250 µM 5 overnight, the unreacted cyclooctyne was quenched with excess 2-azidoethanol, and the samples were analyzed by Western blot probing with HRP-α-biotin (FIG. 2). Robust biotinylation was observed for GlyCAM-Ig modified with SiaNAz. Native GlyCAM-Ig lacking azides showed no background labeling, underscoring the exquisite selectivity of the strain-promoted cycloaddition.

As a point of comparison, similar reactions were performed with biotin-modified terminal alkyne 6 (Scheme 1). In the absence of reagents for copper catalysis, no glycoprotein labeling was observed (FIG. 2). As expected based on previous reports (Sharpless and Finn (2003) *J. Am. Chem. Soc.* 125:3192-3193; and Speers and Cravatt ((2004) *Chem. Biol.* 11:535-546), addition of CuSO$_4$, TCEP and a triazolyl ligand resulted in facile labeling of the azide-modified glycoprotein. The blot was stripped and reprobed with HRP-labeled anti-IgG antibody (HRP-α-IgG) to confirm equal protein loading. Interestingly, consistently diminished anti-IgG immunoreactivity was observed for azide-modified GlyCAM-Ig labeled with 6 in the presence of copper. It is possible that the combination of triazole products and copper damages the epitope recognized by HRP-α-IgG.

Finally, the utility of the strain-promoted reaction for live cell labeling was investigated. Jurkat cells were incubated with 25 µM Ac$_4$ManNAz for 3 d in order to introduce SiaNAz residues into their cell surface glycoproteins. Saxon and Bertozzi (2000) *Science* 287:2007-2010; and Saxon et al. 92002) *J. Am. Chem. Soc.* 124:14893-14902. The cells were reacted with various concentrations of 5 for 1.5 h at rt, then stained with FITC-avidin and analyzed by flow cytometry. As shown in FIG. 3A, cells displaying azides showed a dose-dependent increase in fluorescence upon treatment with the cyclooctyne probe. No detectable labeling of cells lacking azides was observed. The cell surface reaction was also dependent on duration of incubation with 5 (FIG. 3B) and the density of cell-surface azides. No negative effects on cell viability were observed.

FIG. 2.

Labeling of azide-modified GlyCAM-Ig with alkyne probes. Purified GlyCAM-Ig was treated with buffer (−), 250 µM 5, or 250 µM 6 alone or in the presence (cat) of CuSO$_4$, TCEP, and a triazolyl ligand, overnight at rt. Reaction mixtures were quenched with 2-azidoethanol and analyzed by Western blot probing with HRP-α-biotin (upper panel). The blot was then stripped and reprobed with HRP-α-Ig (lower panel).

FIGS. 3A and 3B.

Cell surface labeling with compound 5. Jurkat cells were incubated in the presence (+Az) or absence (−Az) of 25 µM Ac$_4$ManNAz for 3 d. FIG. 3A. The cells were reacted with various concentrations of 5 for 1 h at rt and treated with FITC-avidin; mean fluorescence intensity (MFI) was determined by flow cytometry. FIG. 3B. The cells were incubated with 250 µM 5 for various durations at rt and analyzed as in A. C. The cells were incubated with 100 µM probe for 1 h at rt and analyzed as in A. Error bars represent the standard deviation from three replicates. AU=arbitrary fluorescence units.

The above example demonstrates that [3+2] cycloaddition of azides and cyclooctyne derivatives (modified cyclooctynes) according to a subject method occurs readily under physiological conditions in the absence of auxiliary reagents; and that the selective chemical modification of living cells using a subject method occurs without any apparent toxicity.

Example 2

Synthesis of Additional Cyclooctyne Compounds and their Use in Labeling of Living Cells This example presents the synthesis of compounds 3a and 3b (shown below), the evaluation of their kinetic parameters in reactions with small organic azides, and their use in bioorthogonal labeling of living cells.

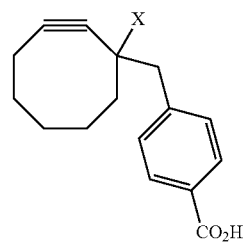

3a, X = H
3b, X = F

Materials and Methods

All chemical reagents were of analytical grade, obtained from commercial suppliers, and used without further purification unless otherwise noted. With the exception of reactions performed in aqueous media, all reaction vessels were flame-dried prior to use. Reactions were performed in a N$_2$ atmosphere, except in the case of reactions performed in aqueous media, and liquid reagents were added with a syringe unless otherwise noted. Tetrahydrofuran (THF) was distilled under N$_2$ from Na/benzophenone immediately prior to use, and CH$_2$Cl$_2$ was distilled from CaH$_2$ immediately prior to use. Chromatography was carried out with Merck 60 230-400 mesh silica gel according to the procedure described by Still. *J. Org. Chem.* (1978) 43:2923-2925. Reactions and chromatography fractions were analyzed with Analtech 250 micron silica gel G plates, and visualized by staining with ceric ammonium molybdate or by absorbance of UV light at 245 nm. When an R$_f$ is reported for a compound, the solvent that was used was the chromatography solvent unless otherwise noted. Organic extracts were dried over MgSO$_4$ and solvents were removed with a rotary evaporator at reduced pressure (20 torr), unless otherwise noted. IR spectra were of thin films on NaCl plates. Unless otherwise noted, $^1$H, $^{13}$C, and $^{19}$F NMR spectra were obtained with 300 MHz or 400 MHz Bruker spectrometers. Chemical shifts are reported in δ ppm referenced to the solvent peak for $^1$H and $^{13}$C and relative to $CFCl_3$ for $^{19}$F. Coupling constants (J) are reported in Hz. Low- and high-resolution fast atom bombardment (FAB) and electron impact (EI) mass spectra were obtained at the UC Berkeley Mass Spectrometry Facility, and elemental analyses were obtained at the UC Berkeley Micro-Mass Facility. Melting points were determined using a MeI-Temp 3.0 melting point apparatus and are uncorrected.

Synthetic Procedures

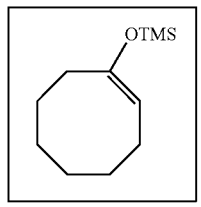

Compound 6

(Cyclooct-1-enyloxy)-trimethylsilane (6)

To a solution of cyclooctanone (40.0 g, 316 mmol) in 200 mL of anhydrous DMF were added triethylamine (TEA, 93.0 mL, 666 mmol) and chlorotrimethylsilane (84.0 mL, 666 mmol). The reaction was heated to reflux. After 15 h, the reaction was quenched with 20 mL of $H_2O$ and the DMF was removed on a rotary evaporator. The residue was diluted with hexanes (300 mL), washed with $H_2O$ (3×100 mL) and brine (1×50 mL), and dried over $MgSO_4$. Distillation under reduced pressure (20 torr) yielded 58.1 g (93%) of the desired product as a colorless oil, by 108° C. (20 torr) (lit. 106° C. at 25 torr). Nakamura, et al. *J. Am. Chem. Soc.* (1976) 98, 2346-2348. IR: 2926, 2851, 1661 cm$^{-1}$. $^1$H NMR (CDCl$_3$, 300 MHz): δ 0.20 (s, 9H), 1.39-1.58 (m, 8H), 2.02 (m, 2H), 2.19 (m, 2H), 4.75 (t, 1H, J=9.0 Hz). (Lit: $^1$H NMR (CDCl$_3$, 600 MHz): δ 0.16 (s, 9H), 1.46 (m, 4H), 1.49 (m, 2H), 1.55 (m, 2H), 1.97 (m, 2H), 2.14 (m, 2H), 4.70 (t, 1H, J=8.0 Hz) (Frimer et al. *J. Org. Chem.* (2000) 65, 1807-1817.) $^{13}$C NMR (CDCl$_3$, 75 MHz): δ 0.4, 25.5, 26.3, 26.4, 27.8, 30.9, 31.0, 105.41, 152.99. (Lit: $^{13}$C NMR (CDCl$_3$, 150 MHz): δ 0.45, 25.52, 26.36, 26.40, 27.83, 30.98, 31.05, 105.45, 153.05) Frimer et al. (2000) supra) FAB-HRMS: Calcd. for $C_{11}H_{23}OSi^+$ [M+H]$^+$: 199.1518. found 199.1520.

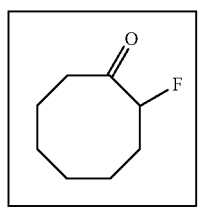

Compound 5b

2-Fluorocyclooctanone (5b)

To a solution of silyl enol ether 6 (57.8 g, 291 mmol) in DMF (350 mL) was added a solution of Selectfluor (124 g, 349 mmol) in DMF (150 mL) over 1 h at rt. The solution was allowed to stir for 12 h. The reaction was quenched with 30 mL of $H_2O$, and the DMF was removed on a rotary evaporator. The residue was diluted with hexanes (500 mL), washed with $H_2O$ (3×200 mL) and brine (1×50 mL), and dried over $MgSO_4$. Following column chromatography (30:1 to 15:1 pentane/ether), a white solid was isolated (38.4 g, 91%, $R_f$=0.30 in 9:1 pentane/ether), mp 48.1-49.8° C. IR: 3429, 2932, 2859, 1721, 1709 cm$^{-1}$. (Lit: 1710 cm$^{-1}$) (Rozen and Menahem. *J. Fluorine Chem.* (1980), 16, 19-31). $^1$H NMR (CDCl$_3$, 400 MHz): δ 1.25 (m, 1H), 1.38-1.55 (m, 4H), 1.61 (m, 1H), 1.73 (m, 1H), 2.05 (m, 3H), 2.30 (m, 1H), 2.55 (m, 1H), 4.86 (ddd, 1H, J=49.6, 6.4, 2.8 Hz). (Lit: $^1$H NMR (CDCl$_3$, 250 MHz): δ 1.36-2.7 (m, 12H), 4.9 (dm, 1H, J=49.5 Hz) (Chambers and Hutchinson *J. Fluorine Chem.* (1998) 89, 229-232)$^{13}$C NMR (CDCl$_3$, 100 MHz): δ 20.3 (d, J=4.0 Hz), 24.4 (d, J=6.0 Hz), 24.5, 26.9, 32.2 (d, J=11.0 Hz), 39.3, 94.7 (d, J=185.0 Hz), 213.4 (d, J=21.0 Hz). (Lit: $^{13}$C NMR (CDCl$_3$, 50 MHz): δ 20.5 (d, J=3.6 Hz), 24.6 (d, J=3.7 Hz), 24.7, 27.2, 32.7 (d, J=21.0 Hz), 39.6, 91.5 (d, J=184.7 Hz), 213.9 (d, J=20.9 Hz) (Chambers and Hutchinson (1998) supra) $^{19}$F NMR (CDCl$_3$, 376 MHz): δ –190.7 (m). (Lit: $^{19}$F NMR (CDCl$_3$, 235 MHz): δ –191.6 (m) (Chambers and Hutchinson (1998) supra)

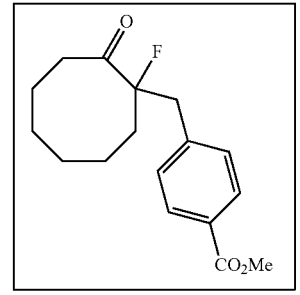

Compound 4b 4-(1-Fluoro-2-oxo-cyclooctylmethyl)benzoic acid methyl ester (4b)

To a solution of LDA (34 mL, 61 mmol, 1.8 M solution in heptane/THF/ethylbenzene) in THF (50 mL) at –78° C. was added a solution of 2-fluorocyclooctanone (5b) (7.38 g, 51.2 mmol) in THF (50 mL) over 2 h using a syringe pump. After 1 h, a solution of methyl 4-bromomethylbenzoate (17.6 g, 76.8 mmol) in THF (50 mL) was added and the reaction was allowed to warm to rt. After 1 h, the reaction mixture was quenched with $H_2O$ (50 mL) and the THF was removed on a rotary evaporator. The residue was diluted with EtOAc (200 mL), washed with $H_2O$ (3×100 mL) and brine (1×50 mL), and dried over $MgSO_4$. Following column chromatography (50:1 to 15:1 hexanes/EtOAc), a white solid was isolated (6.45 g, 43%, $R_f$=0.35 in 9:1 hexanes/EtOAc), mp 53.5-55.2° C. IR: 2931, 2858, 1721 cm$^{-1}$. $^1$H NMR (CDCl$_3$, 400 MHz): δ 1.08 (m, 1H), 1.35-1.65 (m, 7H), 1.86 (m, 2H), 2.04 (app d, 2H, J=9.0 Hz), 2.90 (dd, 1H, J=20.1, 14.1 Hz), 3.14 (dd, 1H, J=28.2, 14.1 Hz), 3.78 (s, 3H), 7.15 (d, 2H, J=7.8 Hz), 7.83 (d, 2H, J=8.4 Hz). $^{13}$C NMR (CDCl$_3$, 100 MHz): δ 21.1, 24.7, 25.3, 27.6, 38.7 (d, J=22.0 Hz), 40.0, 43.4 (d, J=21.0 Hz), 51.9, 102.3 (d, J=189.0 Hz), 128.7, 129.3, 130.5, 140.3, 166.8, 216.0 (d, J=26.0 Hz). $^{19}$F NMR (CDCl$_3$, 376 MHz): δ –166.0 (m). FAB-HRMS: Calcd. for $C_{17}H_{22}O_3F^+$ [M+H]$^+$: 293.1553. found: 293.1560.

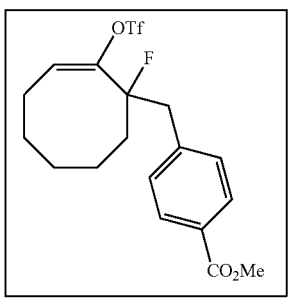

Compound 7b

4-(1-Fluoro-2-trifluoromethanesulfonyloxy-cyclooct-2-enylmethyl)-benzoic acid methyl ester (7b)

To a solution of ketone 4b (4.62 g, 15.8 mmol) in THF (50 mL) at −78° C. was added Potassium hexamethyldisilazide (KHMDS, 35.0 mL, 17.5 mmol, 0.50 M solution in toluene). After 1 h, a solution of N-Phenylbistrifluoromethanesulfonimide (Tf$_2$NPh, 6.18 g, 17.3 mmol) in THF (25 mL) was added and the reaction was allowed to warm to rt. After 30 min, the reaction mixture was concentrated on a rotary evaporator and the product was purified by column chromatography (20:1 to 12:1 hexanes/EtOAc) to yield the desired product (4.90 g, 73%, R$_f$=0.30 in 9:1 hexanes/EtOAc) as a colorless oil. IR: 3424, 2952, 1723, 1646 cm$^{-1}$. $^1$H NMR (CDCl$_3$, 400 MHz): δ 1.38-1.67 (m, 4H), 1.74-1.97 (m, 4H), 1.97-2.18 (m, 2H), 3.16 (app d, 1H, J=3.2 Hz), 3.20 (s, 1H), 3.91 (s, 3H), 5.86 (t, 1H, J=9.6 Hz), 7.26 (d, 2H, J=8.0 Hz), 7.96 (d, 2H, J=8.4 Hz). $^{13}$C NMR (CDCl$_3$, 100 MHz): δ 22.0, 22.1, 23.1, 25.2, 35.1 (d, J=22.0 Hz), 44.3 (d, J=26.0 Hz), 52.0, 95.7 (d, J=177.0 Hz), 118.4 (q, J=317.0 Hz), 123.8, 129.1, 129.4, 130.5, 139.7 (d, J=8.0 Hz), 148.2 (d, J=21.0 Hz), 166.8. $^{19}$F NMR (CDCl$_3$, 376 MHz): δ −73.7 (app d, 3H, J=3.8 Hz), −144.3 (app d, 1H, J=3.8 Hz). FAB-HRMS: Calcd. for C$_{18}$H$_{21}$O$_5$F$_4$S$^+$ [M+H]$^+$: 425.1046. found: 425.1046.

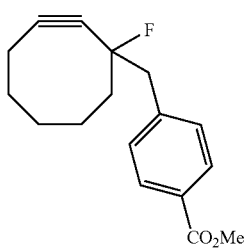

Compound 8b

4-(1-Fluoro-cyclooct-2-ynylmethyl)benzoic acid methyl ester (8b)

To a solution of vinyl triflate 7b (14.3 g, 33.5 mmol) in THF (100 mL) at 0° C. was added LDA (23.5 mL, 35.2 mmol, 1.8M in heptane/THF/ethyl benzene) dropwise, using a syringe pump, over 3 h. LDA was added until the starting material was consumed. The reaction was quenched with 20 mL of H$_2$O and the THF was removed on a rotary evaporator. The residue was diluted with EtOAc (300 mL), washed with H$_2$O (3×100 mL) and brine (1×50 mL), and dried over MgSO$_4$. After silica gel chromatography (50:1 to 25:1 hexanes/EtOAc), a colorless oil was isolated (5.41 g, 59%, R$_f$=0.40 in 9:1 hexanes/EtOAc). IR: 3421, 2930, 2854, 2223, 1721, 1613 cm$^{-1}$. $^1$H NMR (CDCl$_3$, 300 MHz): δ 1.35 (m, 1H), 1.66-1.76 (m, 2H), 1.76-2.07 (m, 4H), 2.07-2.33 (m, 3H), 3.03 (app d, 1H, J=2.1 Hz), 3.10 (s, 1H), 3.90 (s, 3H), 7.37 (d, 2H, J=8.1 Hz), 7.98 (d, 2H, J=8.1 Hz). $^{13}$C NMR (CDCl$_3$, 75 MHz): δ 20.5, 26.0 (d, J=1.5 Hz), 29.4, 34.0, 44.7 (d, J=26.0 Hz), 48.8 (d, J=25.0 Hz), 51.9, 90.5 (d, J=32.0 Hz), 95.2 (d, J=175.0 Hz), 104.5 (d, J=11.0 Hz), 128.6, 129.3, 130.3, 141.2, 167.0. $^{19}$F NMR (CDCl$_3$, 376 MHz): δ −139.0 (m). FAB-HRMS: Calcd. for C$_{17}$H$_{20}$O$_2$F$^+$ [M+H]$^+$: 275.1447. found: 275.1442.

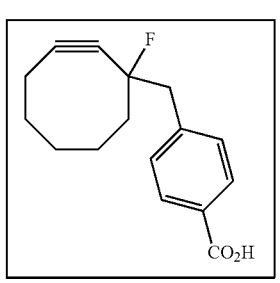

Compound 3b

4-(1-Fluoro-cyclooct-2-ynylmethyl)benzoic acid (3b)

To a solution of cyclooctyne 8b (1.8 g, 6.6 mmol) in dioxane (30 mL) and H$_2$O (7.5 mL) was added finely crushed LiOH (3.1 g, 130 mmol). The suspension was heated to 50° C. and stirred for 3 h. The dioxane was removed on a rotary evaporator and the reaction mixture was diluted with CH$_2$Cl$_2$ (100 mL). The organic layer was washed with 1 N HCl (2×100 mL), H$_2$O (3×100 mL), and brine (1×25 mL), and dried over MgSO$_4$, yielding a white solid (1.7 g, 98%, R$_f$=0.30 in 27:3:1 hexane/EtOAc/AcOH), mp 132.0-132.5° C. (dec). IR: 3442, 2926, 2851, 2674, 2557, 2224, 1686, 1611 cm$^{-1}$. $^1$H NMR (DMSO-d$_6$, 400 MHz): δ 1.39 (app quintet, 1H, J=7.6 Hz), 1.64 (m, 2H), 1.76 (m, 2H), 2.10 (m, 5H), 3.07 (s, 1H), 3.11 (d, 1H, J=8.0 Hz), 7.38 (d, 2H, J=8.0 Hz), 7.87 (d, 2H, J=8.4 Hz), 12.9 (br s, 1H). $^{13}$C NMR (DMSO-d$_6$, 100 MHz): δ 19.8, 25.7, 29.0, 33.7, 43.7 (d, J=25.0 Hz), 47.6 (d, J=25.0 Hz), 90.7 (d, J=32.0 Hz), 95.4 (d, J=173.0 Hz), 104.5 (d, J=10.0 Hz), 129.0, 129.2, 130.4, 141.2, 167.2. $^{19}$F NMR (CD$_3$CN, 376 MHz): δ −139.4 (m). FAB-HRMS: Calcd. for C$_{16}$H$_{18}$O$_2$F$^+$ [M+H]$^+$: 261.1291. found: 261.1291. Anal. calcd. for C$_{16}$H$_{17}$O$_2$F: C, 79.31; H, 7.49. Found: C, 79.07; H, 7.26.

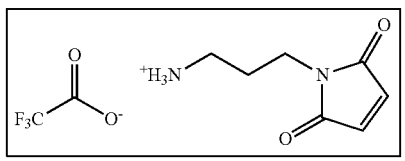

Compound 13

3-(2,5-Dioxo-2,5-dihydro-pyrrol-1-yl)-propylammonium trifluoroacetate (13)

To a solution of maleimide (3.12 g, 32.2 mmol) and PPh$_3$ (8.29 g, 31.6 mmol) in THF (150 mL) was added N-(t-butoxycarbonyl)propanolamine (5.00 mL, 29.3 mmol) and then diisopropyl azodicarboxylate (6.80 mL, 35.1 mmol). The solution was stirred at rt for 48 h, concentrated on a rotary evaporator, and purified by column chromatography (4:1 to 2:1 hexanes/EtOAc) to yield 10.3 g of a mixture of the N-Boc protected product and diisopropyl hydrazinedicarboxylate. The mixture was dissolved in a solution of $CH_2Cl_2$ (60 mL) and $H_2O$ (5 mL), and then trifluoroacetic acid (TFA, 35 mL) was added. The reaction was stirred for 5 h at rt and then diluted with $CH_2Cl_2$ (50 mL) and $H_2O$ (50 mL). The aqueous layer was washed with $CH_2Cl_2$ (3×50 mL) and then concentrated to yield the desired product as a yellow oil (7.51 g, 96%). IR: 3435, 2959, 2917, 2849, 1707, 1683 $cm^{-1}$. $^1H$ NMR (DMSO-$d_6$, 400 MHz): δ 1.76 (app q, 2H, J=7.2 Hz), 2.78 (m, 2H), 3.45 (t, 2H, J=6.8 Hz), 7.02 (s, 2H), 7.79 (br s, 3H). $^{13}C$ NMR (DMSO-$d_6$, 100 MHz): δ 26.7, 34.6, 37.0, 116.0 (q, 289.0 Hz), 134.7, 158.9 (q, J=36.0 Hz), 171.3. $^{19}F$ NMR (DMSO-$d_6$, 376 MHz): δ −72.9 (s). FAB-HRMS: Calcd. for $C_7H_{11}N_2O_2^+$ [M+H]$^+$: 155.0821. found: 155.0824.

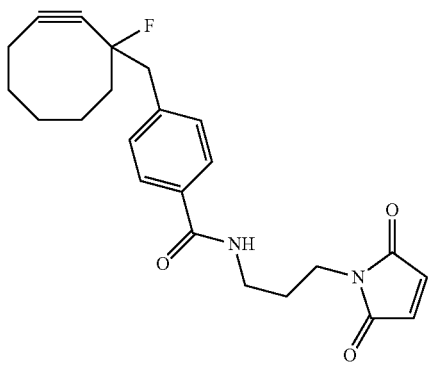

Compound 12b

N-[3-(2,5-Dioxo-2,5-dihydro-pyrrol-1-yl)-propyl]-4-(1-fluorocyclooct-2-ynylmethyl)benzamide (12b)

TEA (0.508 mL, 3.65 mmol) was added to a solution of cyclooctyne 3b (0.200 g, 0.768 mmol), amine 13 (0.235 g, 0.875 mmol), O-(7-Azabenzotriazol-1-yl)-N,N,N',N-tetramethyluronium hexafluorophosphate (HATU, 0.305 g, 0.802 mmol), and 1-hydroxybenzotriazole (HOBT, 0.123 g, 0.802 mmol) in $CH_2Cl_2$ (3 mL) at rt. The reaction was stirred for 15 min at rt, quenched with $H_2O$ (10 mL), and diluted with $CH_2Cl_2$ (50 mL). The organic layer was washed with 1 N HCl (3×50 mL), saturated $NaHCO_3$ (3×50 mL), and brine (2×25 mL) and dried over $MgSO_4$. Chromatography of the crude product (2:1 to 1:1 hexanes/EtOAc) yielded the desired product as a white solid (0.198 g, 65%, $R_f$=0.30 in 1:1 hexanes/EtOAc), mp 122.0-124.0° C. (dec). IR: 3413, 2931, 2854, 2222, 1705, 1640 $cm^{-1}$. $^1H$ NMR (CDCl$_3$, 400 MHz): δ 1.39 (m, 1H), 1.74 (m, 2H), 1.81-2.06 (m, 6H), 2.14-2.32 (m, 3H), 3.05 (d, 1H, J=2.8 Hz), 3.09 (s, 1H), 3.40 (q, 2H, J=6.4 Hz), 3.67 (t, 2H, J=6.0 Hz), 6.75 (s, 2H), 6.93 (m, 1H), 7.41 (d, 2H, J=8.0 Hz), 7.81 (d, 2H, J=8.0 Hz). $^{13}C$ NMR (CDCl$_3$, 100 MHz): δ 20.5, 26.0, 28.1, 29.4, 34.0, 34.8, 36.2, 44.6 (d, J=25.0 Hz), 47.8 (d, J=24.0 Hz), 90.7 (d, J=32.0 Hz), 95.3 (d, J=174.0 Hz), 104.5 (d, J=10.0 Hz), 126.7, 130.5, 132.9, 134.2, 139.6, 167.1, 171.1. $^{19}F$ NMR (CDCl$_3$, 376 MHz): δ −139.0 (m). FAB-HRMS: Calcd. for $C_{23}H_{26}N_2O_3F^+$ [M+H]$^+$: 397.1927. found: 397.1920.

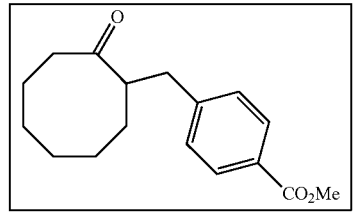

Compound 4a 4-(2-Oxo-cyclooctylmethyl)benzoic acid methyl ester (4a)

To a stirring solution of cyclooctanone (1.76 g, 14.0 mmol) in THF (30 mL) at −78° C. was added LDA (8.54 mL, 15.4 mmol, 1.8 M in heptane/THF/ethylbenzene). After 1 h, a solution of methyl 4-bromomethylbenzoate (3.53 g, 15.4 mmol) in THF (10 mL) was added and the reaction mixture was allowed to warm to rt. After 30 min, the reaction was quenched with $H_2O$ (10 mL) and the THF was removed on a rotary evaporator. The residue was diluted with EtOAc (100 mL), washed with $H_2O$ (3×100 mL) and brine (1×50 mL), and dried over $MgSO_4$. Chromatography of the crude product (50:1 to 9:1 hexanes/EtOAc) yielded the desired product as a colorless oil (3.08 g, 80%, $R_f$=0.30, 9:1 hexanes/EtOAc). IR: 3426, 2929, 2856, 1721, 1700, 1657, 1611 $cm^{-1}$. $^1H$ NMR (CDCl$_3$, 300 MHz): δ 1.10-1.28 (m, 1H), 1.28-1.42 (m, 1H), 1.42-1.80 (m, 6H), 1.80-1.90 (m, 1H), 1.90-2.08 (m, 1H), 2.08-2.18 (m, 1H), 2.22-2.35 (m, 1H), 2.64 (dd, 1H, J=12.6, 6.0 Hz), 3.01 (m, 2H), 3.89 (s, 3H), 7.20 (d, 2H, J=8.1 Hz), 7.93 (d, 2H, J=8.4 Hz). $^{13}C$ NMR (CDCl$_3$, 75 MHz): δ 24.5, 24.6, 25.1, 27.7, 32.9, 38.1, 43.2, 51.5, 52.0, 128.1, 129.0, 129.7, 145.6, 167.0, 218.9. FAB-HRMS: Calcd. for $C_{17}H_{23}O_3^+$ [M+H]$^+$: 275.1647. found: 275.1648.

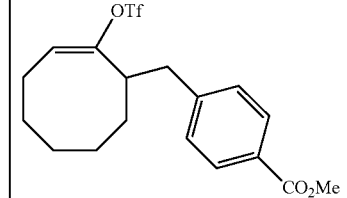

Compound 7a 4-(2-Trifluoromethanesulfonyloxy-cyclooct-2-enyl-methyl)-benzoic acid methyl ester (7a)

To a solution of ketone 4a (2.17 g, 7.91 mmol) in THF (50 mL) at −78° C. was added KHMDS (17.4 mL, 8.70 mmol, 0.50 M solution in toluene). After 1 h, a solution of Tf$_2$NPh (3.11 g, 8.70 mmol) in THF (25 mL) was added and the reaction was allowed to warm to rt. After 30 min, the reaction mixture was concentrated on a rotary evaporator and the product was purified directly by column chromatography (20:1 to 12:1 hexanes/EtOAc) to yield the desired product (2.19 g, 68%, $R_f$=0.35 in 9:1 hexanes/EtOAc) as a colorless oil. The product was isolated as a 9:1 mixture of regioisomers. IR: 2932, 2856, 1723, 1410 $cm^{-1}$. $^1H$ NMR (CDCl$_3$, 400 MHz): δ 1.25-1.38 (m, 1H), 1.38-1.52 (m, 1H), 1.52-1.71 (m, 4H), 1.71-1.85 (m, 2H), 1.98-2.11 (m, 1H), 2.15-2.25 (m, 1H), 2.73 (dd, 1H, J=14.0, 6.8 Hz), 2.99 (dd, 1H, J=13.6, 8.0

Hz), 3.13 (m, 1H), 3.73 (s, 3H), 5.76 (t, 1H, J=8.8 Hz), 7.27 (d, 2H, J=8.0 Hz), 7.98 (d, 2H, J=8.0 Hz). $^{13}$C NMR (CDCl$_3$, 100 MHz): δ 25.2, 25.9, 26.5, 29.8, 33.3, 37.4, 39.8, 52.0, 118.5 (q, J=318.0 Hz), 121.3, 128.4, 128.8, 129.8, 144.8, 151.0, 167.0. $^{19}$F NMR (CDCl$_3$, 376 MHz): δ −73.8 (s). FAB-HRMS: Calcd. for C$_{18}$H$_{22}$O$_5$F$_3$S$^+$ [M+H]$^+$: 407.1140. found: 407.1133.

J=8.4 Hz), 7.91 (d, 2H, J=8.4 Hz), 9.40 (br s, 1H). $^{13}$C NMR (CD$_3$CN, 100 MHz): δ 21.2, 29.2, 30.8, 35.6, 37.3, 40.8, 42.5, 95.7, 97.1, 128.9, 130.1, 130.5, 147.4, 167.8. EI-HRMS: Calcd. for C$_{16}$H$_{18}$O$_2$M$^+$: 242.1307. found: 242.1307. Anal. Calcd. for C$_{16}$H$_{18}$O$_2$: C, 79.31; H, 7.49. Found: C, 79.07; H, 7.26.

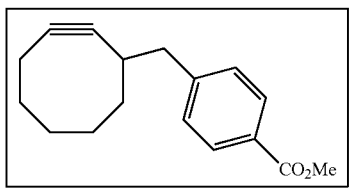

Compound 8a

4-Cyclooct-2-ynylmethylbenzoic acid methyl ester (8a)

To a solution of vinyl triflate 7a (2.14 g, 5.28 mmol) in THF (30 mL) at 0° C. was added LDA (3.52 mL, 5.28 mmol, 1.8 M in heptane/THF/ethyl benzene) dropwise by syringe pump, over 3 h. LDA was added until the starting material was consumed. The reaction was quenched with H$_2$O (10 mL) and the THF was removed on a rotary evaporator. The residue was diluted with EtOAc (100 mL), washed with H$_2$O (3×100 mL) and brine (1×50 mL), and dried over MgSO$_4$. After silica gel chromatography (3:1:0 to 30:10:2 hexanes/toluene/EtOAc), a colorless oil was isolated (0.310 g, 23%, R$_f$=0.20 in 30:10:1 hexanes/toluene/EtOAc). IR: 2930, 2857, 1720 cm$^{-1}$. $^1$H NMR (CDCl$_3$, 300 MHz): δ 1.42 (m, 2H), 1.62 (m, 1H), 1.71-1.88 (m, 3H), 1.88-1.98 (m, 1H), 2.00-2.10 (m, 1H), 2.11-2.23 (m, 2H), 2.63-2.80 (m, 3H), 3.90 (s, 3H), 7.29 (d, 2H, J=8.0 Hz), 7.97 (d, 2H, J=8.4 Hz). $^{13}$C NMR (CDCl$_3$, 100 MHz): δ 20.8, 28.4, 30.0, 34.8, 36.5, 40.3, 41.7, 51.9, 94.9, 96.1, 128.1, 128.9, 129.6, 145.7, 167.1. FAB-HRMS: Calcd. for C$_{17}$H$_{21}$O$_2$$^+$ [M+H]$^+$: 257.1542. found: 257.1536.

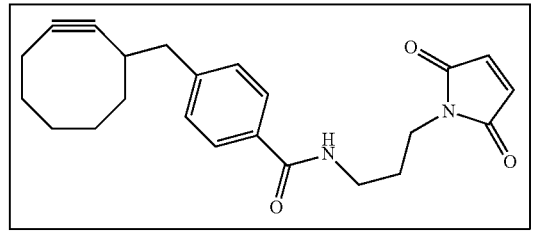

Compound 12a

4-Cyclooct-2-ynylmethyl)-N-[3-(2,5-dioxo-2,5-dihydro-pyrrol-1-yl)propyl]benzamide (12a)

TEA (0.184 mL, 0.396 mmol) was added to a solution of cyclooctyne 3a (64 mg, 0.26 mmol), amine 13 (106 mg, 0.396 mmol), and HATU (111 mg, 0.291 mmol) in CH$_2$Cl$_2$ (2 mL) at rt. The reaction was stirred for 15 min at rt, quenched with H$_2$O (10 mL), and diluted with CH$_2$Cl$_2$ (50 mL). The organic layer was washed with 1 N HCl (3×50 mL), saturated NaHCO$_3$ (3×50 mL), and brine (2×25 mL), and dried over MgSO$_4$. Chromatography of the crude product (2:1 to 1:1 hexanes/EtOAc) yielded the desired product as a colorless oil (69 mg, 69%, R$_f$=0.30 in 1:1 hexanes/EtOAc). IR: 3411, 3099, 2925, 2849, 1704, 1639 cm$^{-1}$. $^1$H NMR (CDCl$_3$, 400 MHz): δ 1.42 (m, 2H), 1.61 (m, 1H), 1.70-1.97 (m, 6H), 2.00-2.09 (m, 1H), 2.09-2.22 (m, 2H), 2.62-2.78 (m, 3H), 3.38 (q, 2H, J=6.4 Hz), 3.65 (t, 2H, J=6.0 Hz), 6.74 (s, 2H), 6.93 (m, 1H), 7.29 (d, 2H, J=8.0 Hz), 7.78 (d, 2H, J=8.0 Hz). $^{13}$C NMR (CDCl$_3$, 100 MHz): δ 20.8, 28.2, 28.4, 29.9, 34.7, 34.8, 36.1, 36.5, 40.0, 41.6, 94.9, 96.2, 126.9, 129.0, 132.2, 134.2, 144.0, 167.1, 171.2. FAB-HRMS: Calcd. for C$_{23}$H$_{27}$N$_2$O$_3$$^+$ [M+H]$^+$: 379.2022. found: 379.2014.

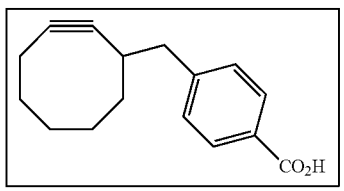

Compound 3a

4-Cyclooct-2-ynylmethylbenzoic acid (3a)

To a solution of cyclooctyne 8a (283 mg, 1.11 mmol) in dioxane (12 mL) and H$_2$O (3 mL) was added finely crushed LiOH (530 mg, 22.1 mmol). The suspension was heated to 50° C. and stirred for 3 h. The dioxane was removed on a rotary evaporator. The residue was diluted with EtOAc (50 mL), washed with 1 N HCl (3×50 mL), H$_2$O (3×50 mL), and brine (2×50 mL), and dried over MgSO$_4$ to yield a white solid (254 mg, 95%, R$_f$=0.25 in 27:3:1 hexane/EtOAc/AcOH), mp 112.0-113.9° C. (dec). IR: 3071, 2922, 2846, 1680 cm$^{-1}$. $^1$H NMR (CD$_3$CN, 400 MHz): δ 1.35-1.48 (m, 2H), 1.56-1.66 (m, 1H), 1.66-1.95 (m, 4H), 2.01-2.17 (m, 3H), 2.70 (d, 1H, J=5.2 Hz), 2.71 (d, 1H, J=1.2 Hz), 2.76 (m, 1H), 7.33 (d, 2H,

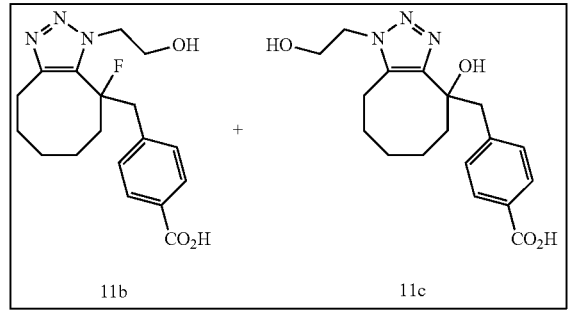

Compounds 11b and 11c

Compounds 11b and 11c. Cyclooctyne 3b (0.20 g, 0.77 mmol) and 2-azidoethanol (N.J. Agard, unpublished results, 461 μL, 3.84 mmol) were dissolved in CH$_3$CN (7.2 mL) and Dulbecco's phosphate-buffered saline (1×, pH 7.4, 5.9 mL). The reaction was stirred at rt for 12 h and concentrated on a rotary evaporator. Chromatography of the crude product (95:4:1 to 90:9:1 CH$_2$Cl$_2$/MeOH/AcOH) afforded a 20:1 mixture of 11b:11a (99 mg, 37%, $R_f$=0.30 in 90:9:1 $CH_2Cl_2$/MeOH/AcOH) and 11c (144 mg, 54%, $R_f$=0.15 in 90:9:1 $CH_2Cl_2$/MeOH/AcOH) as colorless oils.

Compound 11b: mp 175.0-178.0° C. IR: 3442, 2103, 1644 $cm^{-1}$. $^1$H NMR ($CD_3OD$, 400 MHz): δ 1.39 (m, 3H), 1.55 (m, 1H), 1.68 (m, 1H), 1.79 (m, 1H), 2.15 (m, 2H), 2.30 (m, 1H), 2.82 (ddd, 1H, J=14.8, 4.4, 4.4 Hz), 3.38 (app t, 1H, J=12.4 Hz), 3.48 (app t, 1H, J=14.4 Hz), 4.02 (m, 1H), 4.09 (m, 1H), 4.46 (dt, 1H, J=14.0, 5.2 Hz), 4.62 (ddd, 1H, J=14.0, 8.0, 5.6 Hz), 7.05 (d, 2H, J=8.4 Hz), 7.86 (d, 2H, J=8.4 Hz). $^{13}$C NMR ($CD_3OD$, 100 MHz): δ 22.9, 25.4, 27.4, 28.4, 38.3 (d, J=22.0 Hz), 48.1 (d, J=26.0 Hz), 53.9 (d, J=7.0 Hz), 62.1, 97.0 (d, J=174.0 Hz), 130.7, 131.2, 132.0, 135.2 (d, J=23.0 Hz), 141.6 (d, J=8.0 Hz), 145.7 (d, J=5.0 Hz), 169.8. $^{19}$F NMR ($CD_3OD$, 376 MHz): δ −145.7 (m). FAB-HRMS: Calcd. for $C_{18}H_{23}FN_3O_3^+$ $[M+H]^+$: 348.1723. found: 348.1722.

Compound 11c: mp 183.0-184.6° C. IR: 3423, 2068, 1643 $cm^{-1}$. $^1$H NMR ($CD_3OD$, 400 MHz): δ 1.31 (m, 1H), 1.40-1.68 (m, 4H), 1.74 (m, 1H), 1.92 (m, 2H), 2.39 (m, 1H), 2.95 (m, 1H), 3.32 (app q, 2H, J=12.8 Hz), 3.88 (t, 2H, J=5.6 Hz), 4.34 (m, 2H), 7.05 (d, 2H, J=8.0 Hz), 7.82 (d, 2H, T=8.0 Hz). $^{13}$C NMR ($CD_3OD$, 100 MHz): δ 21.7, 23.8, 25.9, 28.1, 38.9, 51.1, 51.2, 55.0, 62.2, 130.3, 130.9, 132.0, 135.7, 144.2, 149.9, 170.8. FAB-HRMS: Calcd. for $C_{18}H_{24}N_3O_4^+$ $[M+H]^+$: 346.1767. found: 346.1764.

Kinetic Evaluation of Cyclooctyne Probes

Stock solutions of cyclooctynes 3a and 3b (50 mM), benzyl azide (500 mM) and 2-azidoethanol (500 mM) were made in either $CD_3CN$ or a 55:45 mixture of $CD_3CN$ and deuterated Dulbecco's phosphate-buffered saline (pH 7.4, made with $D_2O$). Gentle heating and/or sonication in a $H_2O$ bath was required to fully dissolve 3a and 3b. An NMR tube was charged with 450 µL of either 3a or 3b, and 50 µL of either benzyl azide or 2-azidoethanol, and the reaction was monitored over time using $^1$H NMR spectroscopy.

In the case of the reactions of 3a and 3b with benzyl azide, the kinetic data were derived by monitoring the change in integration of resonances corresponding to the benzylic protons in benzyl azide (δ ~4.2 ppm) compared to the corresponding resonances of the triazole products (δ ~5.0 to 5.5 ppm). In the case of the reactions of 3a and 3b with 2-azidoethanol, the kinetic data were derived from integration of the resonances corresponding to the more downfield pair of aromatic protons (δ ~7.9 ppm) in the cyclooctyne starting material compared to the corresponding resonances in the triazole products (δ ~7.7 to 7.8 ppm).

Second-order rate constants for the reaction were determined by plotting 1/[benzyl azide] versus time in the case of the reactions of 3a and 3b with benzyl azide and by plotting 1/[3a] versus time or 1/[3b] versus time in the case of the reactions of 3a and 3b with 2-azidoethanol, and subsequent analysis by linear regression. Second-order rate constants correspond to one half of the determined slope (Table 1). Error bars represent standard deviations from three replicate experiments.

TABLE 1

Kinetic comparison of azido-ligations[a].

| Labeling reagent | Azide | Solvent | k ($\times 10^{-3}$ $M^{-1}s^{-1}$) |
|---|---|---|---|
| 3b | $PhCH_2N_3$ | $CD_3CN$ | 4.2 |
| 2 | $PhCH_2N_3$ | $CD_3CN$ | 2.4[b] |
| 3a | $PhCH_2N_3$ | $CD_3CN$ | 1.2 |
| 1 (R' = H) | $PhCH_2N_3$ | $CD_3CN$ | 1.9[c] |
| 3b | $HOCH_2CH_2N_3$ | $CD_3CN$/PBS (55:45) | 4.0 |
| 2 | $HOCH_2CH_2N_3$ | $CD_3CN$/PBS (55:45) | 2.0[b] |
| 3a | $HOCH_2CH_2N_3$ | $CD_3CN$/PBS (55:45) | 1.1 |

[a]Second-order rate constants for the [3 + 2] cycloaddition were determined at 22° C. using $^1$H NMR (see experimental section for a full description of the experimental setup).
[b]Agard, N. J., Prescher, J. A., Bertozzi, C. R. J. Am. Chem. Soc. 2004, 126, 15046-15047.
[c]Lin, F. L., Hoyt, H. M., van Halbeek, H., Bergman, R. G., Bertozzi, C. R. J. Am. Chem. Soc. 2005, 127, 2686-95.

Cell Surface Labeling of Jurkat Cells with 12b-FLAG

Jurkat cells (human T-cell lymphoma) were maintained in a 5% $CO_2$, water-saturated atmosphere and grown in RPMI-1640 media supplemented with 10% FCS, penicillin (100 units/mL), and streptomycin (0.1 mg/mL). Cell densities were maintained between $1 \times 10^5$ and $1.6 \times 10^6$ cells/mL. The cells were incubated for 3 d in untreated media or media containing 25 µM $Ac_4ManNAz$. After growth in the presence of $Ac_4ManNAz$, cells were distributed into a 96-well V-bottom tissue culture plate. The cells were pelleted (3500 rpm, 3 min) and washed twice with 200 µL of labeling buffer (PBS, pH 7.4 containing 1% FCS). Cells were then incubated with 12b-FLAG or 1-FLAG in labeling buffer for 1 h at rt. After incubation, cells were pelleted, washed twice with labeling buffer, and resuspended in the same buffer containing FITC-conjugated α-FLAG (1:3000 dilution of the Sigma stock). After a 30-min incubation on ice (in the dark), the cells were washed twice with 200 µL of cold labeling buffer and then diluted to a volume of 400 µL for flow cytometry analysis.

Results

To test the specificity of the cycloaddition reaction in a biological context, 3a and 3b were further derivatized with FLAG-C (SEQ ID NO:3), a short peptide epitope for which a fluorescently labeled antibody is commercially available (Scheme 2). Maleimide derivatives 12a and 12b were prepared by the HATU-mediated coupling of 3a and 3b with amino-maleimide 13. Cysteine-terminated FLAG peptides were ligated to maleimides 12a and 12b using standard conditions and the resulting probes (12α-FLAG and 12b-FLAG) were purified by HPLC for use in cell labeling experiments.

Scheme 2

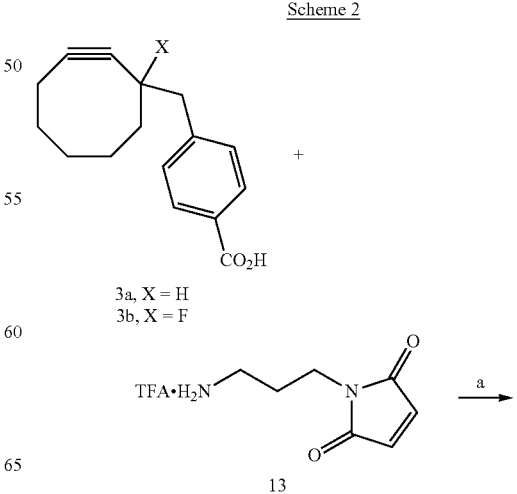

3a, X = H
3b, X = F

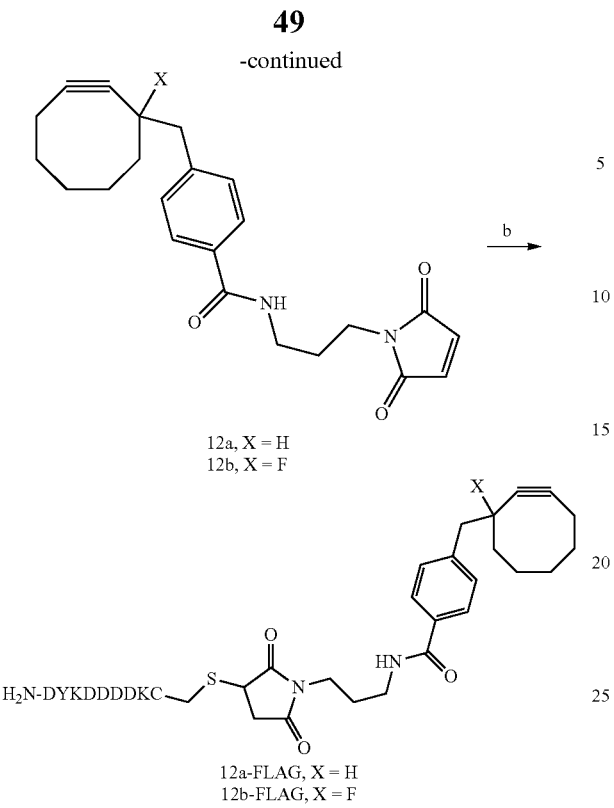

12a, X = H
12b, X = F

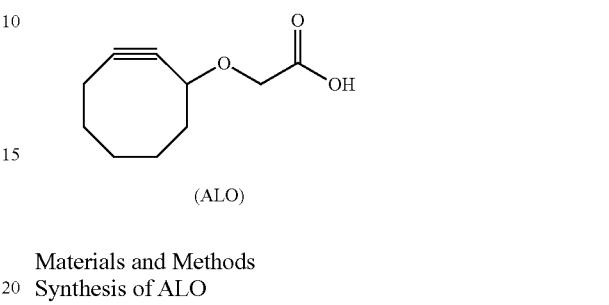

12a-FLAG, X = H
12b-FLAG, X = F

Scheme 2: (a) O-(7-Azabenzotrialzol-1-yl)-N,N,N′,N′-tetramethyluronium hexafluorophosphate (HATU), 1-hydroxybenzotriazole (HOBT), TEA, CH$_2$Cl$_2$, 69% (12a), 65% (12b); (b) H$_2$N-DYKDDDDKC-CO$_2$H (SEQ ID NO:3), DMF/H$_2$O.

Azides were installed on the surfaces of Jurkat cells by metabolic labeling of sialic acid residues. Briefly, cells fed peracetylated N-azidoacetylmannosamine (Ac$_4$ManNAz), an analog of N-acetylmannosamine (ManNAc), convert the azido sugar to the corresponding azido sialic acid (SiaNAz) within cell surface glycoproteins. Reaction of the cell-surface azides with phosphine or cyclooctyne probes containing the FLAG epitope was monitored by flow cytometry using visualization with a FITC-conjugated α-FLAG antibody (FIG. 4a).

Figure 4A:
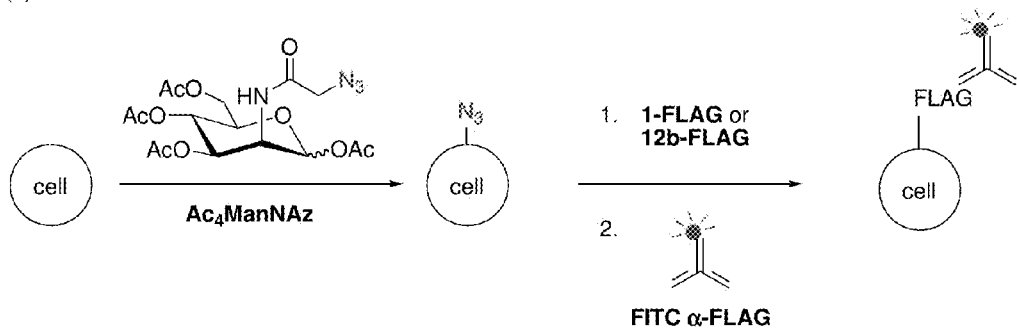
FIG. 4A schematically depicts labeling of cell-surface azides with cyclooctyne probes.
Figure 4B:
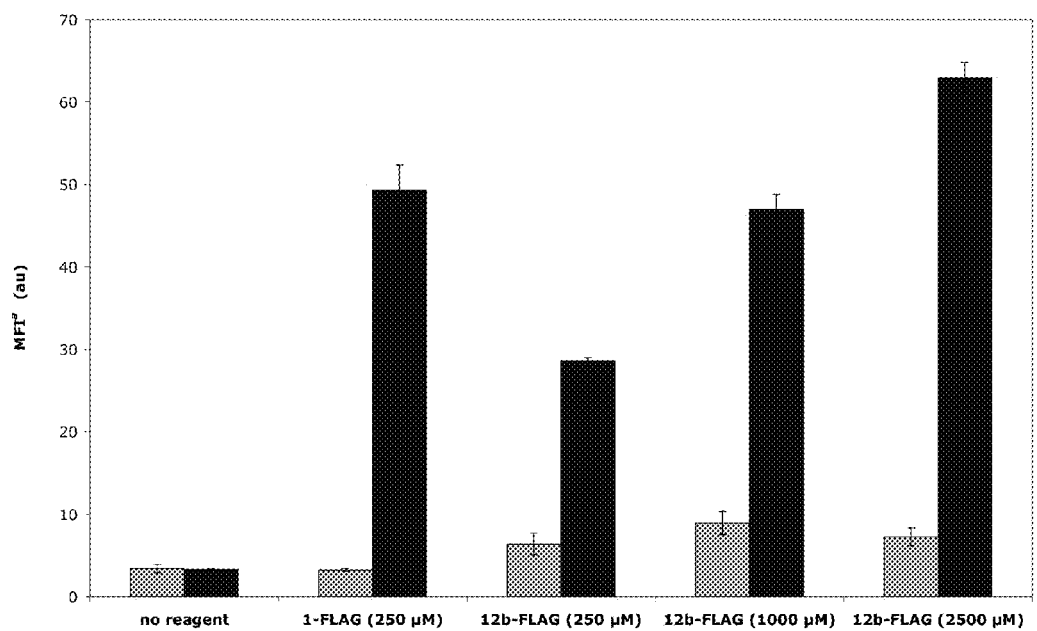
FIG. 4B depicts cyclooctyne probe labeling of Jurkat cells that contain cell-surface azides.

As shown in FIG. 4b, the 12b-FLAG labels Jurkat cells in an azide-dependent fashion, similar to a previously studied FLAG-labeled phosphine probe capable of undergoing the Staudinger ligation (1-FLAG). Agard et al. (2004). *J. Am. Chem. Soc.* 126, 15046-15047. Compound 12b-FLAG labels cells in a dose-dependent manner. No toxicity was observed in any of these experiments.

FIGS. 4A and 4B. Labeling of cell-surface azides with cyclooctyne probes. (a) Jurkat cells were incubated with azido sugars for 3 d and then labeled with various concentrations of 1-FLAG or 12b-FLAG. Detection of the FLAG peptide was achieved using a FITC-conjugated α-FLAG (anti-FLAG) antibody, followed by analysis by flow cytometry. (b) Dark blue: Cells incubated with 25 μM Ac$_4$ManNAz for 3 d. Light blue: Cells incubated in the absence of Ac$_4$ManNAz. Error bars indicate the standard deviation of three trials. $^a$Mean fluorescence intensity.

Example 3

Synthesis of an Aryl-Less Cyclooctyne Compound and its Use in Labeling of Living Cells This example describes synthesis of an "aryl-less" octyne (ALO; shown below) and the use of a conjugated ALO to label living cells in vivo. The aryl-less octyne was synthesized; then a maleimide group was introduced. The maleimide functionality allows for specific conjugation to the thiol of a cysteine containing peptides. Described below are the synthesis of the octyne, the octyne-linked maleimides, their conjugation to a FLAG peptide, and the subsequent use of these conjugates on cell surfaces and in living mice.

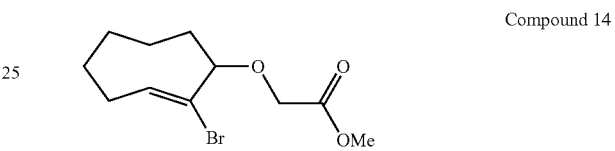

(ALO)

Materials and Methods
Synthesis of ALO

Compound 14

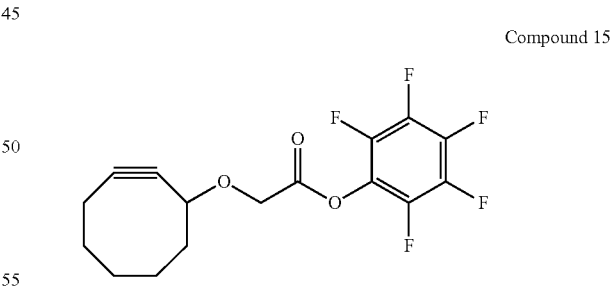

Compound 14.

AgClO$_4$ (2.40 g, 11.6 mmol) was added to a solution of dibromobicycle 1 (1.00 g, 3.72 mmol) and methyl glycolate (6.0 ml, 78.2 mmol) dissolved in toluene (4 mL) in a flame-dried, aluminum-foil-wrapped flask. The reaction was stirred for 2 h, diluted with pentane (20 mL), and filtered to remove insoluble silver salts. The solution was concentrated and purified by silica gel chromatography (5-10% EtOAc: pet ether; R$_f$ (10% EtOAc: pet ether)=0.32) to yield 2 as a colorless oil (330 mg 1.19 mmol, 22%). $^1$H NMR (300 MHz, CD$_3$Cl) δ 6.20 (dd, 1H, J=3.9, 11.7) 4.23 (d, 1H, J=16.5), 4.11 (m, 1H) 3.96 (d, 1H, J=16.5), 3.73 (s, 1H), 2.70 (m, 1H), 2.25 (m, 1H), 0.8-2.1 (m, 8H). EI LRMS calculated C$_{11}$H$_{18}$O$_3$Br [M+H]$^+$ 278.2 found 278.1.

Compound 15

Compound 15.

A suspension of NaOMe (128 mg, 2.38 mmol) in anhydrous DMSO (2 mL) was added to compound 2 (330 mg, 1.19 mmol) dissolved in anhydrous DMSO (3 mL). The reaction was stirred 20 min and additional NaOMe (250 mg, 4.8 mmol in 1.5 mL of DMSO) was added. The reaction was stirred until the starting material was completely consumed as determined by TLC (20 min). Water (1 ml) was added to the reaction and it was stirred overnight. The reaction was acidified with 1 M HCl (75 mL) and extracted twice with EtOAc (50 mL). The combined organic extracts were dried over MgSO$_4$, filtered, and solvent was removed in vacuo. (The reaction can be purified at this point to yield the free acid, but is most often taken on in crude form to give the activated pentafluorophenyl ester) The reaction mixture was dissolved in 5 ml CH$_2$Cl$_2$, and to this solution was added Et$_3$N (332 µL, 2.38 mmol) followed by pentafluorophenyltrifluoroacetate (409 µL, 2.38 mmol). The reaction was stirred 3 h at rt, solvent was removed in vacuo, and the product was purified by silica gel chromatography (1.5-3% EtOAc: petroleum ethers; R$_f$ (3% EtOAc)=0.30) to yield 3 as a clear oil (274 mg, 0.78 mmol, 66%). $^1$H NMR (400 MHz, CD$_3$Cl) δ 4.42 (m, 1H), 4.25 (d, 1H, J=15.2), 4.13 (d, 1H, J=15.2), 1.5-2.3 (m, 10H) EI LRMS calcd. for C$_{16}$H$_{14}$O$_3$F$_5$ [M+H]$^+$ 349.3. found 349.0.

Synthesis of Maleimide Octynes

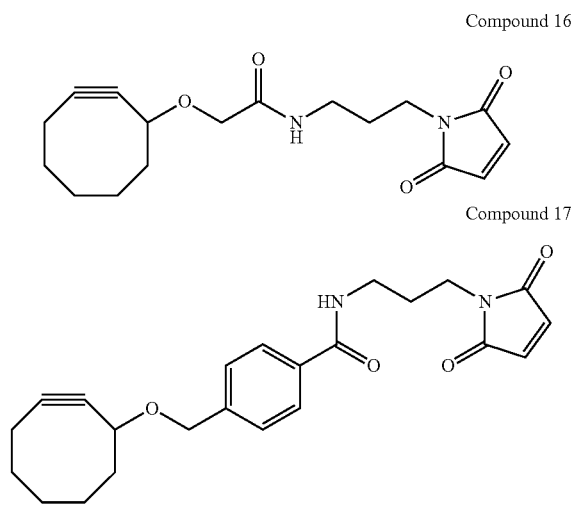

Compound 16

Compound 17

Compounds 16 and 17 were synthesized as follows. TEA (1.5 eq) was added to a solution of cyclooctyne-PFP (1 eq.), and amine 13 (1.5 eq.), in CH$_2$Cl$_2$ at rt. The reaction was stirred for 2 h at rt, quenched with H$_2$O, and diluted with CH$_2$Cl$_2$. The organic layer was washed with 1 N HCl (x3) saturated NaHCO$_3$ (x3), and brine (x2), and dried over MgSO$_4$. Chromatography of the crude product (hexanes/EtOAc) yielded the desired product as a colorless oil.

Synthesis of oct-FLAG Conjugates

Octyne-maleimide (1 eq) was added to a solution of FLAG-C (DYKDDDDKC; SEQ ID NO:3) prepared by standard solid-phase peptide synthesis) (1.2 eq) in 1:1 DMF:H$_2$O and stirred overnight. The crude reaction mixture was concentrated and purified via reversed-phase HPLC (Varian Dynamax HPLC system with 254-nm detection, on a Microsorb C-18 preparative column at a flow rate of 20 mL/min). All HPLC runs used the following gradient: 5-25% acetonitrile in water over 10 min, followed by 35-50% acetonitrile in water over 30 min.

Mice

B6D2F1 mice were obtained from The Jackson Laboratory (Bar Harbor, Me.). All animals were housed and monitored at the Northwest Animal Facility (Berkeley, Calif.), and experiments were performed according to guidelines established by the Animal Care and Use Committee at the University of California, Berkeley (protocol number R234-0504B).

General Protocol for Compound Administration

Mice were administered daily doses of Ac$_4$ManNAz (0-300 mg/kg in ~200 µL of 70% DMSO, from a stock solution of 50 mg/mL) intraperitoneally (i.p.) for 7 days. Twenty-four hours after the final Ac$_4$ManNAz injection, mice were injected i.p. with oct-FLAG (0-40 µmol in ~200 µL H$_2$O), Phos-FLAG (20 µmol in ~200 µL H$_2$O), or vehicle alone (H$_2$O). After 3 h, the mice were anesthetized with isoflurane and sacrificed, and their splenocytes were isolated using a standard protocol.

Labeling of Splenocyte Cell Surface Azides Ex Vivo

Splenocytes from one spleen were suspended in RPMI medium 1640 and distributed among wells of a 96-well V-bottom tissue culture plate (3 wells per treatment, ~5×10$^5$ cells/well). The cells were pelleted (3500 rpm, 3 min), rinsed three times with labeling buffer (1% FBS in PBS, pH 7.4), and incubated with 0-500 µM oct-FLAG in labeling buffer, Phos-FLAG in labeling buffer, or labeling buffer alone. After incubation at rt for 1 h, the cells were rinsed three times with labeling buffer, treated with FITC-α-FLAG (1:900 dilution) or FITC-conjugated mouse IgG$_1$ isotype control (1:200 dilution) in labeling buffer for 30 min on ice, rinsed, and analyzed by flow cytometry.

Results

Figure 5:
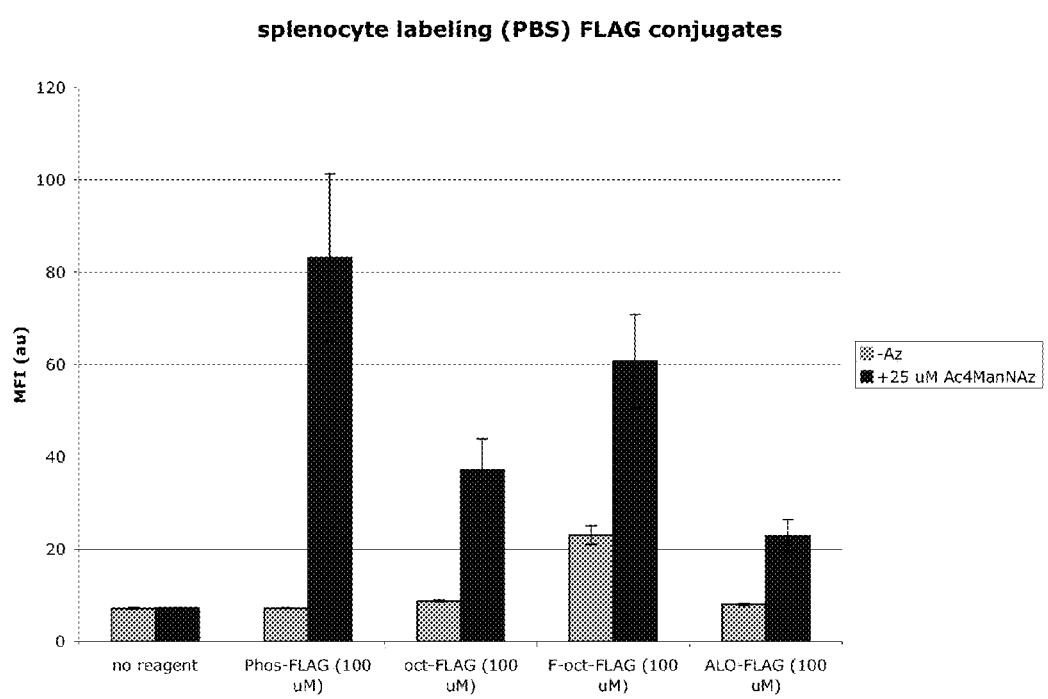
FIG. 5 depicts labeling of splenocytes with cyclooctyne-FLAG.

Splenocyte Labeling of FLAG Conjugates:

Splenocytes grown in the presence of Ac$_4$ManNAz were labeled as described in the procedures. The results are shown in FIG. 5. Phosphine-FLAG ("Phos-FLAG") serves as a positive control of ligation, and the three synthesized octynes all show bioorthogonality as demonstrated by increased labeling in the present of azide bearing cells. The degree of labeling is consistent with in vitro kinetic data within the octynes. The more hydrophobic octynes (F-oct(MOFO) and Oct (the first reported cyclooctyne) show some background.

Figure 6:
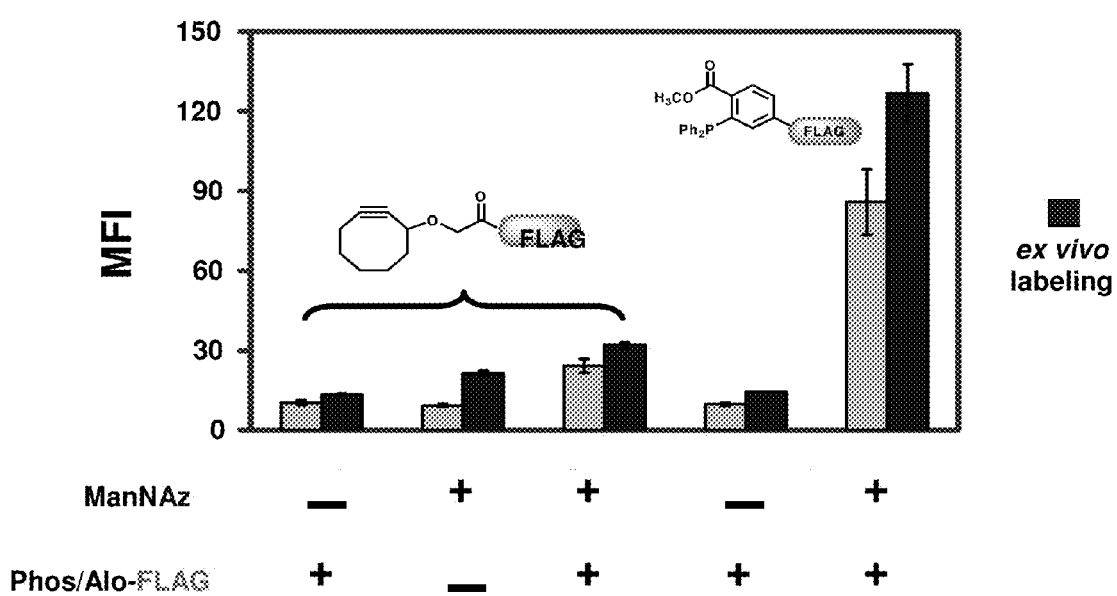
FIG. 6 depicts in vivo labeling of mice with cyclooctyne-FLAG compounds.

In Vivo Labeling of Mice:

Mice were injected with azide labeled sugars as described in the procedures. They were subsequently injected with phosphine-FLAG or ALO-FLAG, sacrificed and their cells were analyzed for the presence of FLAG via flow cytometry. The results are shown in FIG. 6. ALO-FLAG, but not F-oct-FLAG or Oct-FLAG, demonstrates the ability to perform this strain-promoted cycloaddition in a living animal.

Example 4

Synthesis and Characterization of Dimethoxy Azacyclooctyne

Materials and Methods

General Synthetic Procedures.

All chemical reagents were purchased from Aldrich, Acros, and TCI chemicals and used without purification unless noted otherwise. Anhyd DMF and MeOH were purchased from Aldrich or Acros in sealed bottles; all other solvents were purified via packed columns as described by Pangborn et al.[1] In all cases, magnesium sulfate was used as a drying agent and solvent was removed with a Buchi Rotovapor R-114 equipped with a Welch self-cleaning dry vacuum. Products were further dried on an Edwards RV5 high vacuum. Thin layer chromatography was performed on Silicycle® 60 Å silica gel plates. Unless otherwise specified reported R$_f$ values are in the solvent system the reaction was monitored in. Flash chromatography was performed using Merck 60 Å 230-400 mesh silica or on a Biotage Flash+® system with Biotage® 10S, 10M, 40S or 40M prepacked silica gel columns.

All $^1$H and $^{13}$C NMR spectra are reported in ppm and standardized against solvent peaks. All coupling constants (J) are reported in Hz. Spectra were obtained on Bruker AVB-400®, DRX-500®, or AV-500® instruments. IR spectra were taken on a Varian 3100 FT-IR using thin films on NaCl plates.

Melting temperatures were obtained on a Barnstead Electrothermal 9300 instrument. Optical rotations were measured using a Perkin Elmer 241 polarimeter. High resolution fast atom bombardment (FAB) and electrospray ionization (ESI) mass spectra were obtained from the UC Berkeley Mass Spectrometry Facility. Elemental analysis was performed at the UC Berkeley Microanalytical Facility.

Methyl 4,6-O-benzylidine-2,3-di-O-methyl-α,D-glucopyranoside (2)

Methyl 4,6-O-benzylidene-α,D-glucopyranoside (1.416 g, 5.176 mmol, Acros) was dissolved in toluene (55 mL, anhyd). To this solution, KOH was added (1.73 g, 30.8 mmol, 6 equiv) followed by $CH_3I$ (2.20 mL, 35.3 mmol, 7 equiv). The mixture was heated to reflux while stirring under $N_2$ and monitored by TLC (1:1 hexanes/EtOAc) for the disappearance of 1 ($R_f$=0.2). Upon reaction completion (approx 4 h), the mixture was cooled to rt and toluene (50 mL) was added and washed with $H_2O$ (3×30 mL). The toluene was dried, decanted, evaporated to dryness and twice azeotroped with toluene to result in 2 as a white powder (1.516 g, 4.885 mmol, 94%, $R_f$=0.7). Mp 123.2-124.0° C. (lit.[2] 121-123° C.). $^1H$ NMR (400 MHz, $CDCl_3$): δ 7.48-7.46 (m, 2H), 7.34-7.28 (m, 3H), 5.51 (s, 1H), 4.82 (d, J=3.4 Hz, 1H), 4.25 (dd, J=9.9, 4.5 Hz, 1H), 3.79 (td, 5.1, 4.4 Hz, 1H), 3.70 (t, J=10.1 Hz, 1H), 3.66 (t, J=9.2 Hz, 1H), 3.60 (s, 3H), 3.52 (s, 3H), 3.50 (t, J=9.3 Hz, 1H), 3.41 (s, 3H), 3.26 (dd, J=9.2, 3.7 Hz, 1H). $^{13}C$ NMR (100 MHz, $CDCl_3$): δ 137.4, 129.0, 128.3, 126.1, 101.4, 98.4, 82.2, 81.5, 79.9, 69.1, 62.3, 61.1, 59.4, 55.3. HRMS (FAB) calcd for $C_{16}H_{23}O_6$ $[M+H]^+$: 311.149464. found: 311.14930.

Methyl 6-bromo-6-deoxy-2,3-di-O-methyl-α,D-glucopyranoside (3)

Methyl 4,6-O-benzylidene-α,D-glucopyranoside (37.97 g, 122.4 mmol) was dissolved in $CCl_4$ (1.5 L, anhyd) and $CaCO_3$ (13.54 g, 135.3 mmol, 1.11 equiv) was added. This mixture was heated to reflux under $N_2$. Once reaching reflux, N-bromosuccinimide (24.228 g, 136.13 mmol, 1.11 equiv, recrystallized) was added and the reaction was monitored by TLC (1:1 hexanes/EtOAc) for the dissapearance of 2 ($R_f$=0.7). Upon reaction completion (approx 1 h), it was cooled to rt and evaporated to dryness. The residue was dissolved in $CH_2Cl_2$ (1 L) and washed with 10% $Na_2SO_3$ (1×1 L), sat. $NaHCO_3$ (1×1 L). Each aqueous wash was extracted with $CH_2Cl_2$ (2×500 mL). All organic layers were combined, dried, decanted, and evaporated to dryness. The residue was dissolved in a solution of 1% NaOH in MeOH (1.5 L). After 1 h, the solution was neutralized with 3M HCl and evaporated to dryness. The residue was dissolved in $H_2O$ (1.5 L) and extracted with $CH_2Cl_2$ (8×500 mL). The organic layers were combined, dried, decanted, and evaporated to dryness. The crude product was purified on 5 Biotage 40M columns with a gradient solvent system of 4:1 hexanes/EtOAc to 1:1 hexanes/EtOAc to result in pure 3 as a clear oil (30.10 g, 105.6 mmol, 86%, $R_f$=0.3). $^1H$ NMR (400 MHz, $CDCl_3$): δ 4.73 (d, J=3.5 Hz, 1H), 3.60-3.53 (m, 3H), 3.49 (s, 3H), 3.49-3.43 (m, 1H), 3.35-3.24 (m, 8H), 3.11 (dd, J=9.1, 3.5 Hz, 1H). $^{13}C$ NMR (100 MHz, $CDCl_3$): δ 97.3, 82.7, 81.7, 71.6, 69.9, 61.2, 58.5, 55.3, 33.5. HRMS (FAB) calcd for $C_9H_{17}BrO_5Li$ $[+Li]^+$: 291.041939. found: 291.041570.

(2S,3S,4R)N-allyl, N-(methyl succinyl)-4-hydroxy-2,3-dimethoxyhex-5-ene amine (4)

Pyranoside 3 (18.2 g, 63.8 mmol) was dissolved in 19:1 1-propanol/$H_2O$ (1.5 L) in an Erlenmeyer flask equipped with an overhead stirring unit. To this solution, allylamine (150 mL, 2.0 mol, 31 equiv), zinc (223.9 g, 3.423 mol, 54 equiv, acid treated), and $NaBH_3CN$ (18.97 g, 301.9 mmol, 5 equiv) were added. The reaction was heated to 90° C. and monitored by TLC (EtOAc) for the disappearance of 3 ($R_f$=0.7). Upon reaction completion (approx 1 h), the mixture was cooled to rt and filtered through Celite. The filtrate was evaporated to dryness and dissolved in 6:4:1 MeOH/$CH_2Cl_2$/1.5M HCl (1.32 L) and stirred for 1 h (adding 3M HCl as necessary to keep the solution acidic throughout the h) at which point, $H_2O$ (300 mL) was added and the mixture was extracted with $CH_2Cl_2$ (3×600 mL). The organics were dried, decanted, and evaporated to a residue. The resulting crude amine was dissolved in MeOH (600 mL, anhyd). To this solution, N,N-diisopropylethylamine (12.2 mL, 70.0 mmol, 1.1 equiv) followed by methyl succinyl chloride (8.6 mL, 70 mmol, 1.1 equiv) were added and the mixture was stirred at rt under $N_2$ for 1 h, at which point the reaction was quenched with $H_2O$ (100 mL) and the MeOH was removed via rotary evaporation. To the resulting aqueous solution, $H_2O$ (500 mL) was added and extracted with $CH_2Cl_2$ (3×650 mL). The organics were combined, dried, decanted, and evaporated to dryness. The crude product was purified on 3 Biotage 40M columns with a gradient solvent system starting with 25:1 toluene/acetone and ending with 3:1 toluene/acetone (product begins to elute at 10:1 toluene/acetone) to result in pure 4 as a colorless oil (14.776 g, 44.858 mmol, 70%). $R_f$=0.6 in 1:1 toluene/acetone. $[α]_D^{28}$=-38.8° (c 0.943, $CH_2Cl_2$). 1:0.5 mixture of rotamers (designated rot) $^1H$ NMR (500 MHz, $CDCl_3$): δ 5.98-5.88 (m, 1H, 1rotH), 5.79-5.71 (m, 1H, 1rotH), 5.36 (d, J=17.2 Hz, 1rotH), 5.35 (d, J=17.2 Hz, 1H), 5.24-5.11 (m, 3H, 3rotH), 4.32-4.27 (m, 1H, 1rotH), 4.16-4.13 (m, 1H, 1rotH), 4.07-4.03 (m, 1H), 3.98-3.94 (m, 1rotH), 3.78 (dd, J=13.9, 3.6 Hz, 1H), 3.72-3.67 (m, 4H, 3rotH), 3.63-3.59 (m, 2rotH), 3.52 (s, 3H, 3 rotH), 3.45-3.38 (m, 3H, 4rotH), 3.25-3.21 (m, 1H, 1rotH), 3.15 (t, J=4.2 Hz, 1H), 2.85-2.80 (m, 1rotH), 2.73-2.60 (m, 5H, 3rotH), 2.33 (d, J=6.5 Hz, 1rotH). $^{13}C$ NMR (125 MHz, $CDCl_3$): δ 173.9, 173.7, 172.2, 172.1, 138.4, 133.6, 132.8, 117.2, 116.7, 116.31, 116.25, 83.4, 82.7, 80.5, 80.4, 72.4, 71.5, 60.7, 60.6, 59.8, 59.7, 52.02, 51.95, 51.9, 48.9, 48.3, 48.2, 29.5, 29.2, 28.2, 28.1. IR: 3441 (b), 3082, 2981, 2933, 2832, 1737, 1641 $cm^{-1}$. HRMS (FAB) calcd for $C_{16}H_{28}NO_6$ $[M+H]^+$: 330.191663. found: 330.192190. Anal. calcd for $C_{16}H_{27}NO_6$: C, 58.34; H, 8.26; N, 4.25. found: C, 58.41; H, 8.22; N, 4.38.

(5R,6S,7S, Z) N-(methyl succinyl)-5-hydroxy-6,7-dimethoxyazacyclooct-3-ene (5)

Compound 4 (790 mg, 2.40 mmol) was dissolved in $CH_2Cl_2$ (200 mL, anhyd) and heated to reflux while stirring under $N_2$. Once at reflux, Grubbs second generation catalyst (163.3 mg, 0.1927 mmol, 0.08 equiv) was added and the reaction was carefully monitored by TLC in 1:1 toluene/acetone for the disappearance of # ($R_f$=0.6) adding more catalyst if necessary (at 2.25 h 61 mg catalyst added). Upon completion (approx 5 h), the mixture was cooled to rt, evaporated to dryness, and immediately purified on a Biotage 40M column with a gradient of 8:1 toluene/acetone, 6:1 toluene/acetone, 4:1 toluene/acetone. This procedure resulted in pure 5 as a brown oil (500.1 mg, 1.661 mmol, 69%, $R_f$=0.4). $[α]_D^{28}$=-82.6° (c 1.12, $CH_2Cl_2$). 1:0.18 mixture of rotamers. $^1H$ NMR (500 MHz, $CDCl_3$): δ 5.63 (ddd, J=11.9, 6.4, 2.0 Hz, 1H), 5.56-5.54 (m, 2rotH), 5.48-5.45 (m, 1H), 4.41-4.30 (m, 2rotH), 4.35 (t, J=8.0 Hz, 1H), 4.30 (apparent d, 17.5 Hz, 1H), 4.07 (dd, J=13.8, 3.1 Hz, 1H), 3.73 (dd, J=17.2, 5.0 Hz, 1H, 2rotH), 3.66 (s, 3H, 3rotH), 3.62-3.56 (m, 4H, 3rotH), 3.50 (s, 3H), 3.45 (s, 3rotH), 3.42-3.39 (m, 2rotH), 3.27 (s, 1H), 3.08 (apparent dd, J=9.0 Hz, 5.6 Hz, 1rotH), 2.93 (dd, J=9.4, 7.7 Hz, 1H, 1rotH), 2.81 (dd, J=13.8, 9.6 Hz, 1H), 2.68-2.52 (m, 4H, 4rotH). $^{13}$C NMR (100 MHz, CDCl$_3$): δ 173.3, 173.1, 171.5, 134.5, 132.4, 125.3, 123.7, 85.5, 85.2, 81.4, 80.5, 68.1, 66.8, 60.8, 60.1, 58.0, 57.8, 51.6, 47.8, 46.0, 45.3, 45.2, 29.0, 28.7, 28.3. IR: 3472 (b), 2933, 2828, 1735, 1636 cm$^{-1}$. HRMS (FAB) calcd for $C_{14}H_{24}NO_6$ [M+H]$^+$: 302.160363. found: 302.159780.

(6R,7S, Z) N-(methyl succinyl)-6,7-dimethoxy-5-oxoazacylclooct-3-ene

To a solution of 5 (435.6 mg, 1.505 mmol) in CH$_2$Cl$_2$ (100 mL, anhyd), pyridinium chlorochromate (494.4 mg, 2.294 mmol, 1.5 equiv) was added. The mixture was heated to 40° C. and stirred under N$_2$ overnight. The following day, the reaction was cooled to rt, H$_2$O (75 mL) was added, and extracted with CH$_2$Cl$_2$ (3×100 mL). The organics were combined, dried, decanted, and evaporated to dryness to result in crude product which was purified on a Biotage 40S column using a solvent system of 8:1 toluene/acetone, 6:1 toluene/acetone, 4.5:1 toluene/acetone to result in pure (6R,7S, Z) N-(methyl succinyl)-6,7-dimethoxy-5-oxoazacylclooct-3-ene as a clear oil (360 mg, 1.21 mmol, 80%). R$_f$=0.6 in 1:1 toluene/acetone. $[α]_D^{28}$+35.5° (c 4.46, CH$_2$Cl$_2$). 1:1 mixture of rotamers. NMR (500 MHz, CDCl$_3$): δ 6.17 (apparent d, J=11.8 Hz, 1H), 5.95-5.88 (m, 2H), 5.69 (d, J=11.9 Hz, 1H), 4.26 (dd, J=17.4, 4.3 Hz, 1H), 4.11 (d, J=19.7 Hz, 1H), 3.96 (d, J=19.7 Hz, 1H), 3.81-3.71 (m, 6H), 3.61-3.59 (m, 8H), 3.48-3.30 (m, 13H), 2.62-2.40 (m, 7H), 2.36-2.31 (m, 1H). $^{13}$C NMR (125 MHz, CDCl$_3$): δ 203.2, 202.2, 173.8, 173.7, 172.5, 171.9, 137.5, 132.5, 129.1, 126.3, 89.1, 87.3, 81.1, 79.3, 59.6, 59.09, 59.07, 58.3, 51.9, 51.8, 50.4, 49.7, 48.5, 46.8, 29.1, 29.0, 28.02, 27.95. IR: 3590, 3516, 2944, 2830, 1743, 1691, 1655 cm$^{-1}$. HRMS (FAB) calcd for $C_{14}H_{22}NO_6$ [M+H]$^+$: 300.144713. found: 300.144130. Anal. calcd for $C_{14}H_{21}NO_6$: C, 56.18; H, 7.07; N, 4.68. found: C, 56.17; H, 7.09; N, 4.57.

(3S,4R)N-(methyl succinyl)-3,4-dimethoxy-5-oxoazacyclooctane (6)

(6R,7S, Z) N-(methyl succinyl)-6,7-dimethoxy-5-oxoazacylclooct-3-ene (330.9 mg, 1.109 mmol) was dissolved in EtOH (60 mL) and 10% Pd/C (27.8 mg) was added. The mixture was stirred overnight at rt under H$_2$. The following day, the mixture was filtered through Celite and the filtrate was evaporated to dryness to yield 6 (295 mg, 0.980 mmol, 89%). R$_f$=0.5 in 1:1 toluene/acetone. $[α]_D^{28}$+29.7° (c 6.24, CH$_2$Cl$_2$). 1:0.66 mixture of rotamers. $^1$H NMR (500 MHz, CDCl$_3$): δ 4.00 (dd, J=14.0, 4.5 Hz, 1H), 3.87 (d, J=8.0 Hz, 1H), 3.75-3.69 (m, 3rotH), 3.65-3.39 (m, 8H, 6rotH), 3.34 (s, 3rotH), 3.29-3.20 (m, 3H, 2rotH), 3.08 (dt, J=14.5, 5.0 Hz, 1H), 2.69-2.25 (m, 6H, 8rotH), 2.12-2.07 (m, 3H), 1.96 (bs, 1rotH). $^{13}$C NMR (125 MHz, CDCl$_3$): δ 209.7, 209.0, 173.8, 173.5, 172.8, 172.4, 88.4, 86.1, 82.3, 80.4, 59.8, 59.1, 58.8, 57.9, 51.9, 51.8, 49.4, 48.3, 47.8, 47.5, 41.3, 37.7, 29.2, 28.9, 28.5, 28.3, 26.0, 25.3. IR: 3587, 3518, 2940, 2831, 1743, 1711, 1655 cm$^{-1}$. HRMS (ESI) calcd for $C_{14}H_{23}NO_6Na$ [M+Na]$^+$: 324.1418. found: 324.1420. Anal. calcd for $C_{14}H_{23}NO_6$: C, 55.80; H, 7.69; N, 4.65. found: C, 55.91; H, 7.77; N, 4.63.

Compound 7.

Ketone 6 (120.2 mg, 0.3993 mmol) was dissolved in 1:1 H$_2$O/EtOH containing 100 mM aniline (4 mL). To this solution, semicarbazide hydrochloride (463.3 mg, 4.136 mmol, 10 equiv) and AcOH (55 drops) was added. The reaction was stirred at rt and monitored by TLC (1:1 toluene/acetone) for the disappearance of 6 (R$_f$=0.5). After the reacton was complete (approx 8 h), the reaction was evaporated to dryness. The crude white solid was sonicated with EtOAc (4×5 mL). The EtOAc was combined, dried, decanted, and evaporated to dryness to result in crude semicarbazone that was directly converted to selenadiazole 7. The crude semicarbazone was dissolved in dioxane (0.8 mL). A solution of SeO$_2$ (204.1 mg, 1.839 mmol, 5 equiv) in 1:1 dioxane/H$_2$O (0.6 mL) was added to the semicarbazone solution. The mixture was stirred overnight at rt and analyzed the following day by LCMS for the presence of 7 ([M+H]$^+$=392) and absence of semicarbazone ([M+H]$^+$=359, [M+Na]$^+$=381). Additional SeO$_2$ was added if necessary to force the reaction to completion (128.3 mg added). Upon reaction completion, the dioxane was evaporated off and more H$_2$O (10 mL) was added. The aqueous solution was extracted with EtOAc (3×25 mL) and the organics were combined, dried, decanted, and evaporated to dryness. The crude product was chromatographed on a Biotage 40S column with CH$_2$Cl$_2$, 80:1 CH$_2$Cl$_2$/MeOH, 70:1 CH$_2$Cl$_2$/MeOH to result in pure 7 as a yellow oil (68 mg, 0.17 mmol, 43%). R$_f$=0.3 in 60:1 CH$_2$Cl$_2$/MeOH. $[α]_D^{28}$+17.6° (c 1.27, CH$_2$Cl$_2$). 1:0.8 mixture of rotamers. $^1$H NMR (500 MHz, CDCl$_3$): δ 5.39 (s, 1rotH), 5.37 (d, J=5.4 Hz, 1H), 4.36 (m, 1rotH), 4.07-4.02 (m, 2rotH), 3.91 (q, J=5.3 Hz, 1H), 3.73 (bs, 2H), 3.67 (s, 3rotH), 3.65 (s, 3H), 3.59-3.53 (m, 4H, 3rotH), 3.45-3.39 (m, 2H, 2rotH), 3.33-3.19 (m, 3H, 5rotH), 2.91-2.83 (m, 1rotH), 2.74-2.53 (m, 5H, 1rotH), 2.48-2.36 (m, 2rotH). $^{13}$C NMR (125 MHz, CDCl$_3$): δ 173.9, 173.7, 173.4, 171.7, 161.2, 159.3, 157.0, 156.3, 82.6, 80.1, 78.8, 77.9, 58.7, 58.5, 57.94, 57.88, 52.0, 51.9, 51.3, 50.5, 50.1, 49.8, 29.6, 29.1, 28.4, 28.3, 26.3, 25.4. IR: 3580, 3057, 2983, 2931, 2828, 1741, 1649 cm$^{-1}$. HRMS (FAB) calcd for $C_{14}H_{22}N_3O_5Se$ [M+H]$^+$: 392.072467. found: 392.071460.

(6S,7S)N-(methyl succinyl)-6,7-dimethoxyazacyclooct-4-yne

Selenadiazole 7 (83.5 mg, 0.214 mmol) was dissolved in m-xylene (50 mL) and heated to 115° C. The reaction was monitored by TLC (1:1 toluene/acetone) for the disappearance of 7 (R$_f$=0.60, UV active, red spot with vanillin) and appearance of azacyclooctyne methyl ester (R$_f$=0.65, green spot with vanillin). Upon reaction completions (approx 30 h), it was cooled to rt, filtered, and the filtrate was evaporated to dryness. The crude product was purified on silica gel (9.5 in$^3$) using a toluene/acetone solvent system starting at 20:1 and ending with 8:1. This procedure resulted in pure (6S,7S)N-(methyl succinyl)-6,7-dimethoxyazacyclooct-4-yne as a slightly yellow oil (27.3 mg, 0.0964 mmol, 45%, R$_f$=0.6). $[α]_D^{28}$+7.5° (c 0.64, CH$_2$Cl$_2$). 1:0.15 mixture of rotamers. $^1$H NMR (400 MHz, D$_2$O): δ 4.38 (apparent d, J=7.9 Hz, 1rotH), 4.24 (dt, J=8.6, 2.6 Hz, 1H, 1rotH), 4.17 (dd, 14.9, 5.4 Hz, 1H), 4.06 (d, J=14.3 Hz, 1H), 4.00 (s, 1rotH), 3.88 (t, J=9.2 Hz, 1rotH), 3.72-3.68 (m, 4H, 3rotH), 3.55-3.44 (m, 3H, 4rotH), 3.38-3.29 (m, 4H, 3rotH), 3.05 (dd, J=14.3, 9.1 Hz, 1H, 1rotH), 2.90-2.64 (m, 5H, 5rotH), 2.33 (dt, J=16.9, 3.2 Hz, 1H), 2.25 (apparent d, J=16.8 Hz, 1rotH). $^{13}$C NMR (100 MHz, CDCl$_3$): δ 173.6 (broad), 172.5, 171.6, 99.0, 96.0, 93.0, 91.0, 87.0, 85.2, 77.8, 77.4, 59.8, 59.3, 57.5, 57.4, 56.4, 55.7, 53.2, 52.3, 52.02, 51.98, 29.5, 29.3, 28.7, 28.3, 22.1, 21.1. IR: 3489, 2931, 2827, 2203, 1736, 1648 cm$^{-1}$. HRMS (FAB) calcd for $C_{14}H_{22}NO_5$ [M+H]$^+$: 284.149798. found: 284.150650.

(6S,7S)N-(succinic acid)-6,7-dimethoxyazacyclooct-4-yne (8)

Cyclooctyne methyl ester (27.3 mg, 0.0964 mmol) was dissolved in 2:1 $H_2O$/dioxane (1.5 mL) and LiOH (45.7 mg, 1.91 mmol, 20 equiv, crushed) was added. The reaction was stirred overnight at rt. The following day the mixture was neutralized with 3M HCl and the dioxane was evaporated off. Additional $H_2O$ (3 mL) was added to the resulting aqueous solution, this solution was acidified with 3M HCl and extracted with EtOAc (5×10 mL). The EtOAc was combined, dried, decanted, and evaporated to dryness. The crude product was purified on silica gel using a gradient solvent system starting with 8:1 toluene/acetone and ending with 1:1 toluene/acetone. This procedure resulted in pure 8 as an off white solid (17.1 mg, 0.0636 mmol, 66%). $R_f$=0.3-0.4 in 1:1 toluene/acetone. $[\alpha]_D^{28}$ –14.6° (c 0.357, $H_2O$). 1:0.1 mixture of rotamers. $^1$H NMR (400 MHz, $D_2O$): δ 4.37 (dt, J=7.8, 2.3 Hz, 1rotH), 4.13 (dt, J=8.7, 2.8 Hz, 1H, 1rotH), 4.18 (dd, J=14.9, 5.4 Hz, 1H), 4.06 (d, J=14.3 Hz, 1H), 3.91 (s, 1rotH), 3.89 (t, J=8.4 Hz, 1rotH), 3.71 (t, J=8.5 Hz, 1H), 3.56 (s, 3H, 3rotH), 3.56-3.46 (m, 2rotH), 3.37-3.28 (m, 4H, 2rotH), 3.04 (dd, J=14.3, 9.0 Hz, 1H, 1rotH), 2.88-2.64 (m, 5H, 5rotH), 2.32 (dt, J=16.6, 3.4 Hz, 1H), 2.24 (apparent d, 16.8 Hz, 1rotH). $^{13}$C NMR (125 MHz, $D_2O$, no rotamer peaks tabulated): δ 177.0, 174.9, 99.0, 89.7, 84.1, 76.1, 58.0, 56.4, 54.1, 51.9, 29.0, 27.7, 20.6. IR: 3434, 2935, 2830, 2358, 2207, 1729, 1642 cm$^{-1}$. HRMS (ESI) calcd for $C_{13}H_{19}NO_5Na$ [M+Na]$^+$: 292.1155. found: 292.1157.

Azacyclooctyne Biotin Conjugate (9)

Cyclooctyne free acid 8 (4.8 mg, 0.018 mmol) was dissolved in $CH_3CN$ (1 mL, anhyd) and cooled to 0° C. N,N-Diisopropylethylamine (10 μL, 0.06, 3 equiv) was added and this solution was stirred under $N_2$ for 10 min at which point, pentafluorophenyl trifluoroacetate (10 μL, 0.058 mmol, 3 equiv) was added dropwise and the reaction was allowed to warm to rt. The rxn was monitored by TLC (1:1 toluene/acetone) for the disappearance of 8 ($R_f$=0.3-0.4). Upon reaction completion (approx 1 h), the mixture was filtered, and the filtrate was evaporated to dryness. The pentafluorophenyl activated cyclooctyne was purified on silica gel using anhyd toluene and anhyd ether in a gradient solvent system of 10:1 toluene/ether to 4:1 toluene/ether. This product was dried and immediately used for the coupling to biotin. N-(13-amino-4,7,10-trioxamidecanyl)biotinamide[3] (7.8 mg, 0.018 mmol, 1 equiv) was dissolved in DMF (0.5 mL, anhyd) and cooled to 0° C. N,N-Diisopropylethylamine (2 drops) was added. The pentafluorophenyl activated cyclooctyne was dissolved in DMF (0.5 mL, anhyd) and this solution was added dropwise to the biotin solution at 0° C. Upon addition of all activated cyclooctyne, the reaction was warmed to rt and monitored by ESI-LCMS for the formation of 9 ([M+H]$^+$=698, [M+Na]$^+$=720). Upon reaction completion (approx 6 h), the mixture was evaporated to dryness and purified by flash chromatography on silica gel. A gradient solvent system was used beginning at 50:3:1 EtOAc/MeOH/$H_2O$ and ending with 8:3:1 EtOAc/MeOH/$H_2O$. This procedure resulted in pure 9 (5.0 mg, 0.0072 mmol, 40%). $R_f$=0.4 in 5:3:1 EtOAc/MeOH/$H_2O$. $^1$H NMR (500 MHz, $D_2O$): δ 4.58 (dd, J=7.9, 4.9 Hz, 1H), 4.40 (dd, J=7.9, 4.5 Hz, 1H), 4.36 (dt, J=7.8, 2.0 Hz, 0.1H), 4.22 (dt, J=8.6, 2.5 Hz, 1H), 4.12 (dd, 14.9, 5.4 Hz, 0.9H), 4.05 (d, J=14.2 Hz, 0.9H), 4.00 (d, J=16.2 Hz, 0.1H), 3.82 (t, J=8.4 Hz, 0.1H), 3.71-3.65 (m, 8.9H), 3.57-3.45 (m, 7.1H), 3.37-3.19 (m, 8.9H), 3.03 (dd, J=14.3, 9.0 Hz, 1H), 2.97 (dd, J=13.1, 5.0 Hz, 1H), 2.92-2.88 (m, 0.1H), 2.79-2.75 (m, 2.9H), 2.65-2.62 (m, 1H), 2.58-2.49 (m, 2H), 2.32 (dt, J=16.8, 3.0 Hz, 0.9H), 2.24 (t, J=7.2 Hz, 2.1H), 1.79-1.53 (m, 8H), 1.44-1.33 (m, 2H). $^{13}$C NMR (125 MHz, $D_2O$): δ 176.7, 174.7, 174.5, 165.2, 98.9, 89.9, 84.3, 76.1, 69.5, 69.3, 68.4, 68.3, 62.0, 60.2, 58.0, 56.5, 55.3, 54.2, 52.0, 39.6, 36.3, 36.2, 35.4, 30.7, 28.24, 28.18, 27.8, 27.6, 25.1, 20.8. HRMS (ESI) calcd for $C_{33}H_{55}N_5O_9SNa$ [M+Na]$^+$: 720.3618. found: 720.3593.

Scheme 3, below, depicts the synthesis of azacyclooctyne 8 and biotin conjugate 9.

Scheme 3

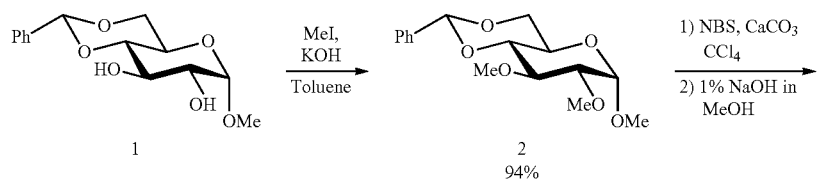

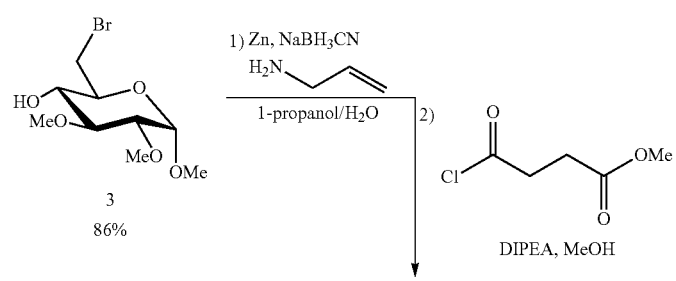

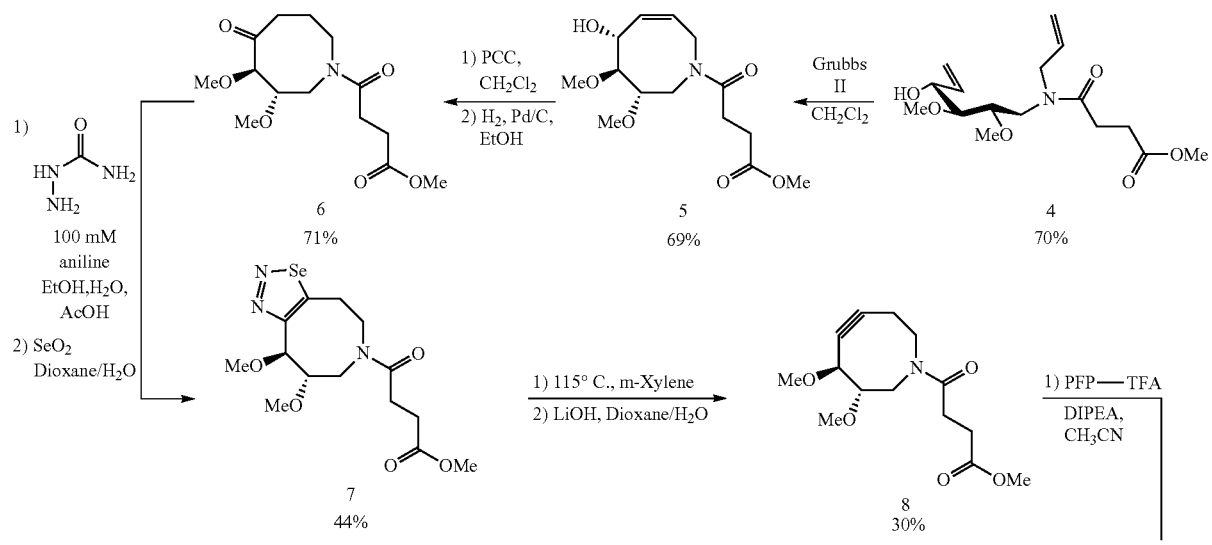
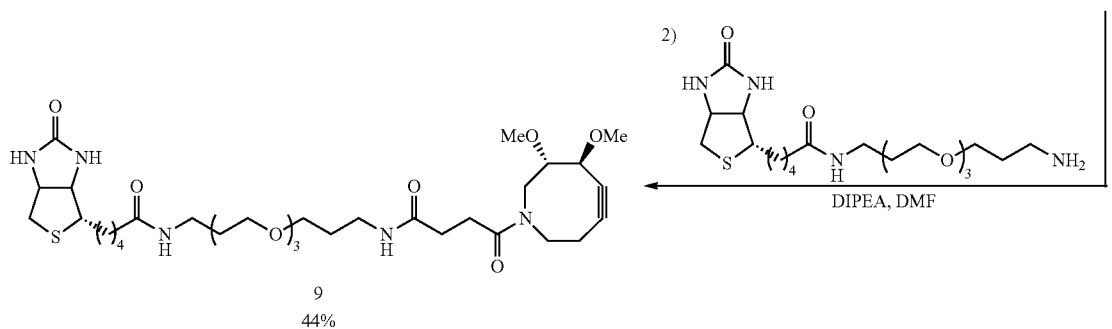
Determination of Rate Constant for the Reaction of Aza-cyclooctyne (8) and Benzyl Azide.
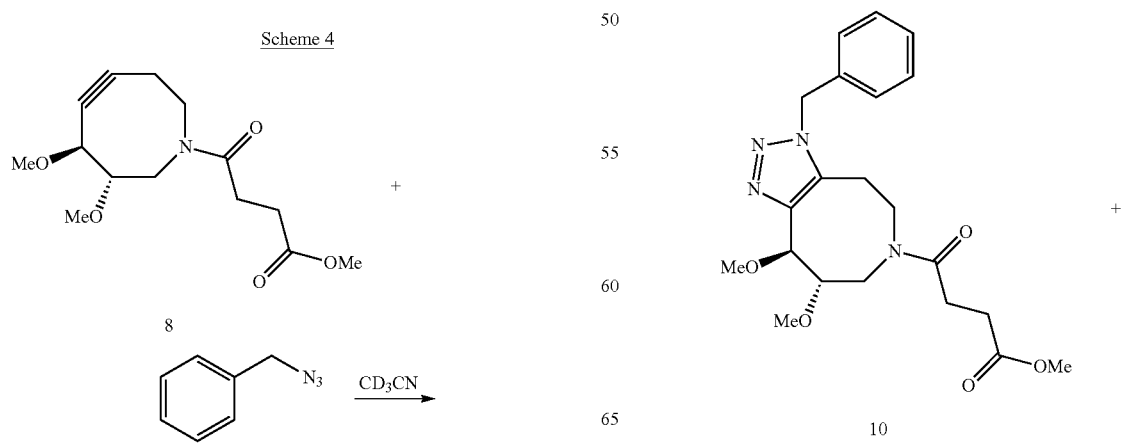

-continued

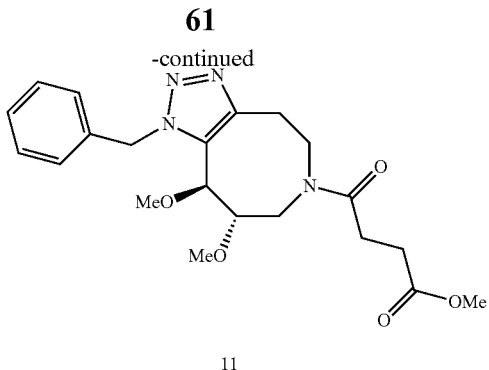

11

The reaction in Scheme 4 was monitored by $^1$H NMR for 4 h. Azacyclooctyne 8 and benzyl azide were separately dissolved in CD$_3$CN and mixed together at a 1:1 concentration of 26 mM. Tert-butyl acetate was used as an internal standard. The percent conversion was calculated by the disappearance of azacyclooctyne relative to the tert-butyl acetate, as determined by integration. No products other than 10 and 11 were apparent by $^1$H NMR. The second order rate constant was determined by plotting 1/[8] versus time. The plot was fit to a linear regression and the slope corresponds to the second order rate constant.

Cell Culture Procedures

Jurkat cells (human T-cell lymphoma) were grown in RPMI-1640 media (Invitrogen Life Technologies) that was supplemented with 10% fetal calf serum (FCS, Hyclone), penicillin (100 units/mL), and streptomycin (0.1 mg/mL). The cells were maintained in a 5% CO$_2$ water-saturated atmosphere and their media was changed every 3 d keeping the cells at densities between $1 \times 10^5$ and $1.6 \times 10^6$ cells/mL (as determined using a Coulter Z2 cell counter).

Western Blot Analysis of Azide-Labeled Cell Lysates

Jurkat cells were grown with or without 25 μM Ac$_4$ManNAz (+ or − respectively) for 3 d as described above. The cells were pelleted (3500 rpm, 4 min) and washed with chilled PBS (3×10 mL). The pellet was suspended in lysis buffer (150 mM NaCl, 20 mM Tris, 1% NP40, pH 7.4 containing mini-protease inhibitors; 2 mL lysis buffer/1 L jurkat lysate) and sonicated (3×30 sec). Following sonication, the lysed cells were pelleted (3700 g for 30 min) and the supernatant was kept. A Bio-RAD® D$_c$ protein assay was performed to determine the protein concentration of each lysate.

150 μg of protein from each lysate was treated with 250 mM 9 or no reagent overnight. 4×SDS-PAGE loading buffer was added to each sample and the samples were separated via electrophoresis and then electroblotted to a nitrocellulose membrane. The membrane was blocked using 5-10% BSA in PBST (PBS pH 7.4 containing 0.1% Tween 20) for 2 h at rt. The blot was incubated with a horse radish peroxidase-conjugated anti-biotin antibody (HRP-α-biotin) (1:100,000) in PBST for 1 h. The membrane was washed with PBST (3×15 min). Detection was performed by chemiluminescence using Pierce SuperSignal® West Pico Chemiluminescent Substrate.

Figure 7:
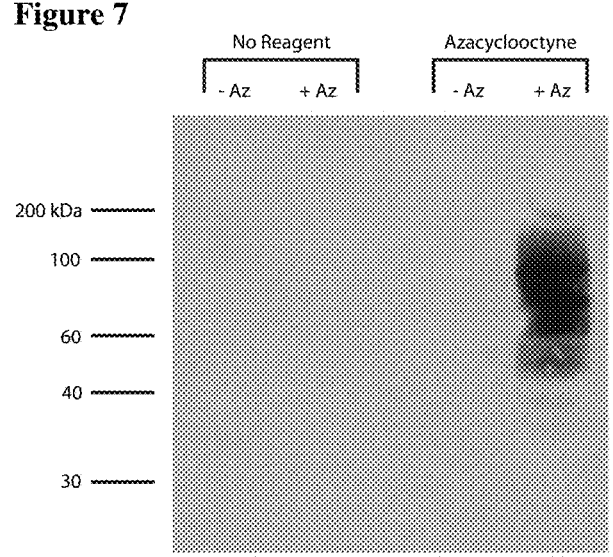
FIG. 7 presents a Western blot of Jurkat cells lysate treated with ($^+$Az) or without ($^-$Az) Ac$_4$ManNAz and labeled with 0 or with 250 µM azacycloocytne biotin conjugate 9.

The data are shown in FIG. 7. FIG. 7 presents a Western blot of Jurkat cells lysate treated with ($^+$Az) or without ($^-$Az) Ac$_4$ManNAz and labeled with 0 or with 250 μM azacyclooo-cytne biotin conjugate 9. Jurkat cells were treated with 0 (−Az) or 25 μM (+Az) Ac$_4$ManNAz for 3 days and lysed. Lysates were reacted with an azacyclooctyne-biotin conjugate (250 μM) or no reagent, and analyzed by SDS-PAGE. A Western blot was performed using anti-biotin antibody. Numbers indicate apparent molecular weight, and equal protein loading was confirmed using Ponceau S stain. The data presented in FIG. 7 demonstrate that azacyclooctyne-biotin can selectively label azide-containing glycoproteins in a cell lysate.

Cell Surface Azide Labeling and Detection.

Jurakt cells were incubated in untreated media or media containing 25 μM Ac$_4$ManNAz. After 3 d, the cells were pelleted are resuspended in FACS buffer (PBS containing 1% FCS, 2×10 mL) and approximately 500,000 cells were placed in each well of a 96 well V-bottom plate. The cells were pelleted (3500 rpm, 3 min) and washed with FACS buffer (1×200 μL). Cells were then incubated for 1 h at rt with 9 or 12 at 250 μM in FACS buffer with 3% DMF (100 μL) or FACS buffer with 3% DMF and no reagent (100 μL). Upon completion of the incubation, cells were pelleted and washed with cold FACS buffer (3×200 μL). Cells were resuspended in FACS buffer (100 μL) containing FITC-avidin (1:200 dilution of Sigma stock) and incubated in the dark at 0° C. for 15 min. Following the incubation, cells were pelleted, washed with cold FACs buffer (1×200 μL) and another FITC-avidin incubation was preformed. After the final, FITC-avidin labeling, the cells were washed with cold FACS buffer (3×200 μL) and then diluted in FACS buffer (400 μL) for flow cytometry analysis. Flow cytometry was performed on a BD Biosciences FACSCalibur flow cytometer equipped with a 488-nm argon laser. All flow cytometry experiments were performed in triplicate, and 20,000 cells were collected per a sample.

Figure 8:
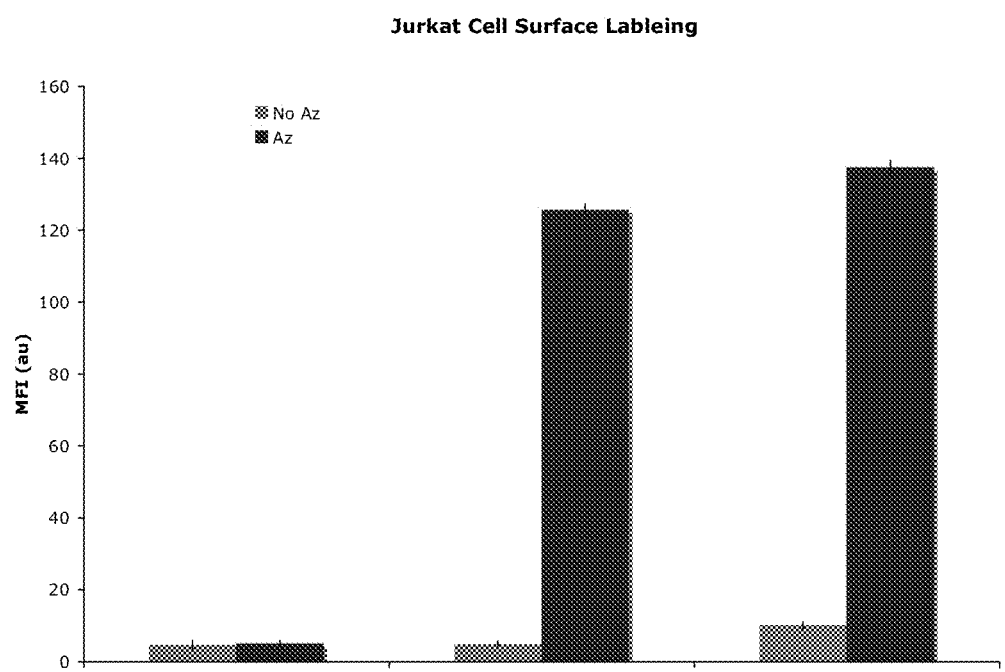
FIG. 8 presents data showing cell surface labeling of Jurkat cells grown in the presence (Az) or absence (no Az) of Ac$_4$ManNAz for 3 days.

The data are shown in FIG. 8. FIG. 8 presents data showing cell surface labeling of Jurkat cells grown in the presence (Az) or absence (no Az) of Ac$_4$ManNAz for 3 days. Cells were labeled for 1 hour with no reagent, with azacyclooo-cytne biotin conjugate 9 (250 μM), or with a cyclooocytyne biotin conjugate 12 (250 μM).

The cells were then stained with fluorescein isothiocyanate (FITC)-labeled avidin and analyzed by flow cytometry. Shown is the mean fluorescence intensity (MFI, in arbitrary units). Error bars represent triplicate samples from the same experiment. Cyclooctyne biotin 12 is a biotin conjugate of the aryl-less octyne ("ALO")

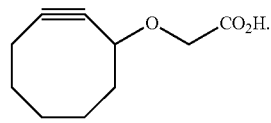 [SMILES: O=C(O)COC1C#CCCCCC1]

The data presented in FIG. 8 demonstrate that azacyclooc-tyne-biotin can label azide-containing membrane-associated glycans in live cells.

Example 5

Synthesis and Characterization of Difluorinated Cycloocytnes

General Materials and Methods

All chemical reagents were of analytical grade, obtained from commercial suppliers, and used without further purification unless otherwise noted. With the exception of reactions performed in aqueous media, all reaction vessels were flame-dried prior to use. Reactions were performed in a N$_2$ atmosphere, except in the case of reactions performed in aqueous media, and liquid reagents were added with a syringe unless otherwise noted. Tetrahydrofuran (THF) was distilled under N$_2$ from Na/benzophenone immediately prior to use, and $CH_2Cl_2$ was distilled from $CaH_2$ immediately prior to use. Flash chromatography was carried out with Merck 60 230-400 mesh silica gel according to the procedure described by Still (1). Reactions and chromatography fractions were analyzed with Analtech 250 micron silica gel G plates and visualized by staining with ceric ammonium molybdate, anisaldehyde, or by absorbance of UV light at 245 nm. Organic extracts were dried over $MgSO_4$, and solvents were removed with a rotary evaporator at reduced pressure (20 torr), unless otherwise noted. Unless otherwise noted, $^1H$, $^{13}C$, and $^{19}F$ NMR spectra were obtained with 300 MHz or 400 MHz Bruker spectrometers. Chemical shifts are reported in δ ppm referenced to the solvent peak for $^1H$ and $^{13}C$ and relative to $CFCl_3$ for $^{19}F$. Coupling constants (J) are reported in Hz. Low- and high-resolution fast atom bombardment (FAB) and electron impact (EI) mass spectra were obtained at the UC Berkeley Mass Spectrometry Facility, and FT-ICR mass spectra were obtained at the Howard Hughes Medical Institute Mass Spectrometry Facility at UC Berkeley. Reversed-phase HPLC was performed using a Rainin Dynamax SD-200 HPLC system with 210 nm detection on a Microsorb C18 analytical or preparative column.

Dulbecco's phosphate-buffered saline (PBS), fluorescein isothiocyanate (FITC)-a-FLAG, and bovine serum albumin (BSA) were purchased from Sigma. RPMI-1640 media was obtained from Invitrogen Life Technologies, Inc., and fetal bovine serum (FBS) was purchased from HyClone Laboratory. FITC-conjugated mouse $IgG_1$ isotype control was obtained from BD Pharmingen. Flow cytometry analysis was performed on a BD FACSCalibur flow cytometer using a 488 nm argon laser. At least $10^4$ cells were analyzed for each sample. Cell viability was ascertained by gating the samples on the basis of forward scatter (to sort by size) and side scatter (to sort by granularity). The average fluorescence intensity was calculated from each of three replicate experiments to obtain a representative value in arbitrary units. For all flow cytometry experiments, data points were collected in triplicate and are representative of at least three separate experiments.

Synthetic Procedures

The synthesis of DIFO (1) was carried out as outlined in Schemes 5 and 6. Various derivatives of DIFO containing fluorophores (DIFO-488, DIFO-568, and DIFO-647), biotin (DIFO-biotin), and the FLAG peptide (DIFO-FLAG) were synthesized as outlined in Scheme 7.

Scheme 5 Synthesis of DIFO (1), part I.

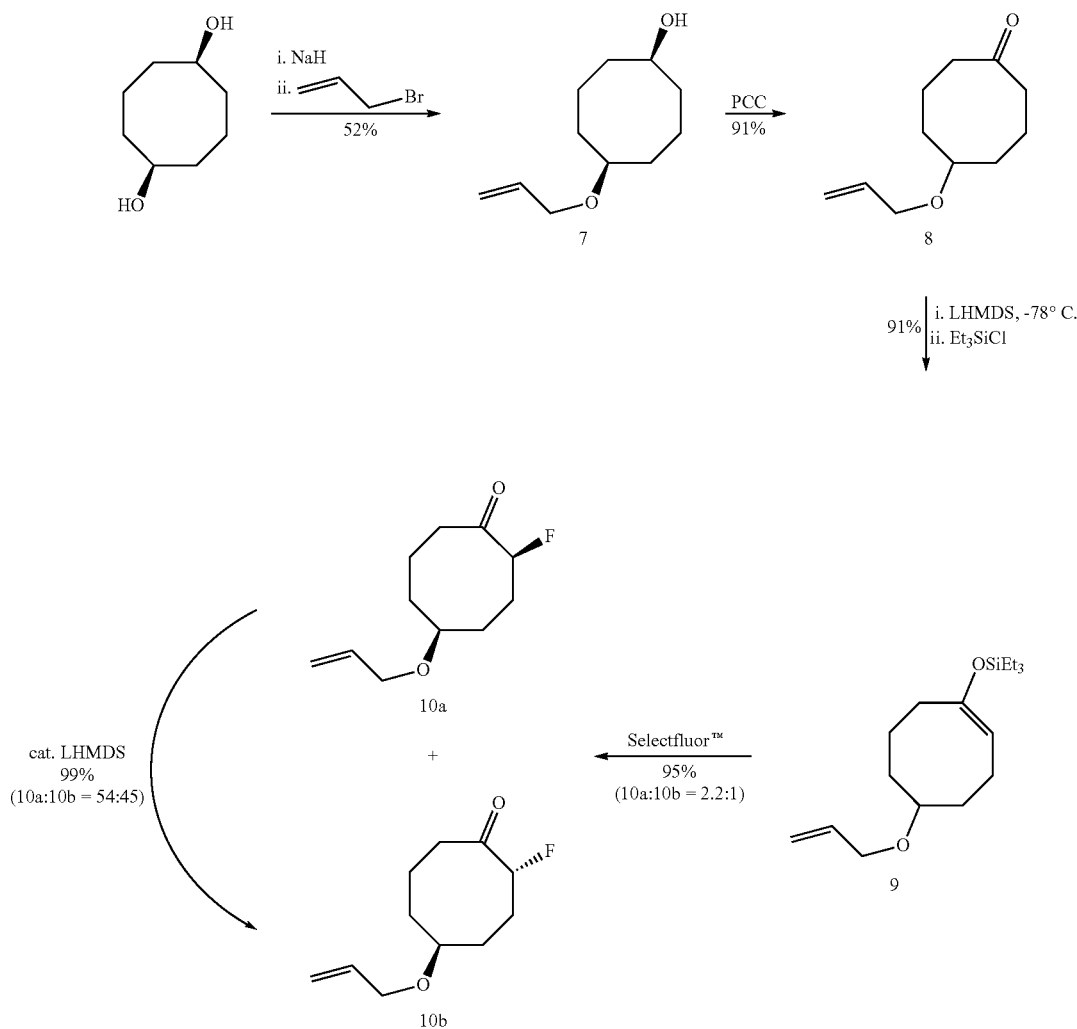

Scheme 6. Synthesis of DIFO (1), part II

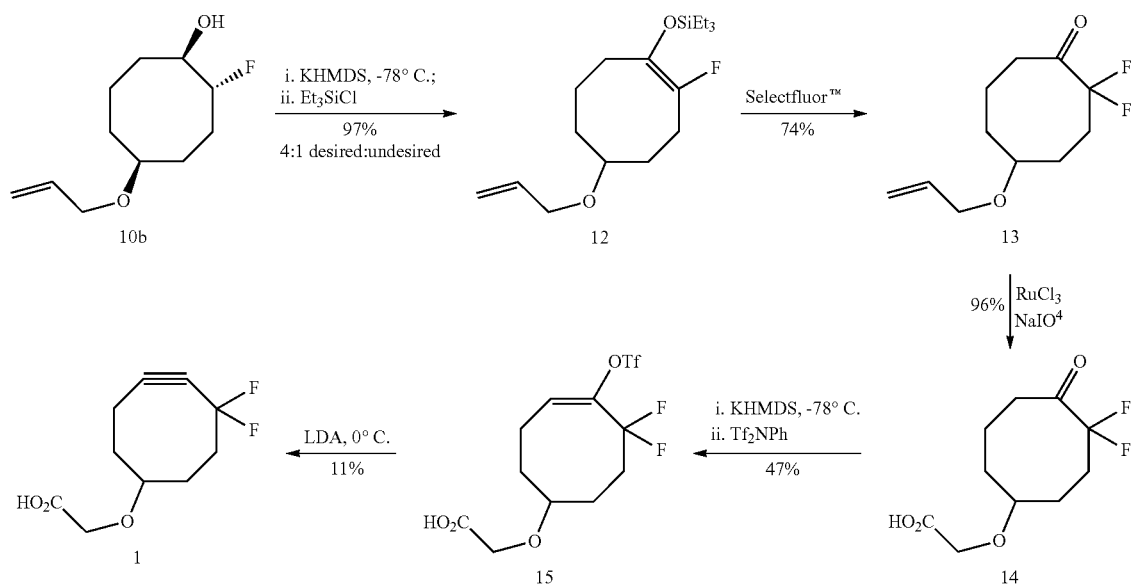

Scheme 7. Synthesis of conjugates of DIFO (biotin, Alexa Fluor 488, 568, and 647, and FLAG peptide)

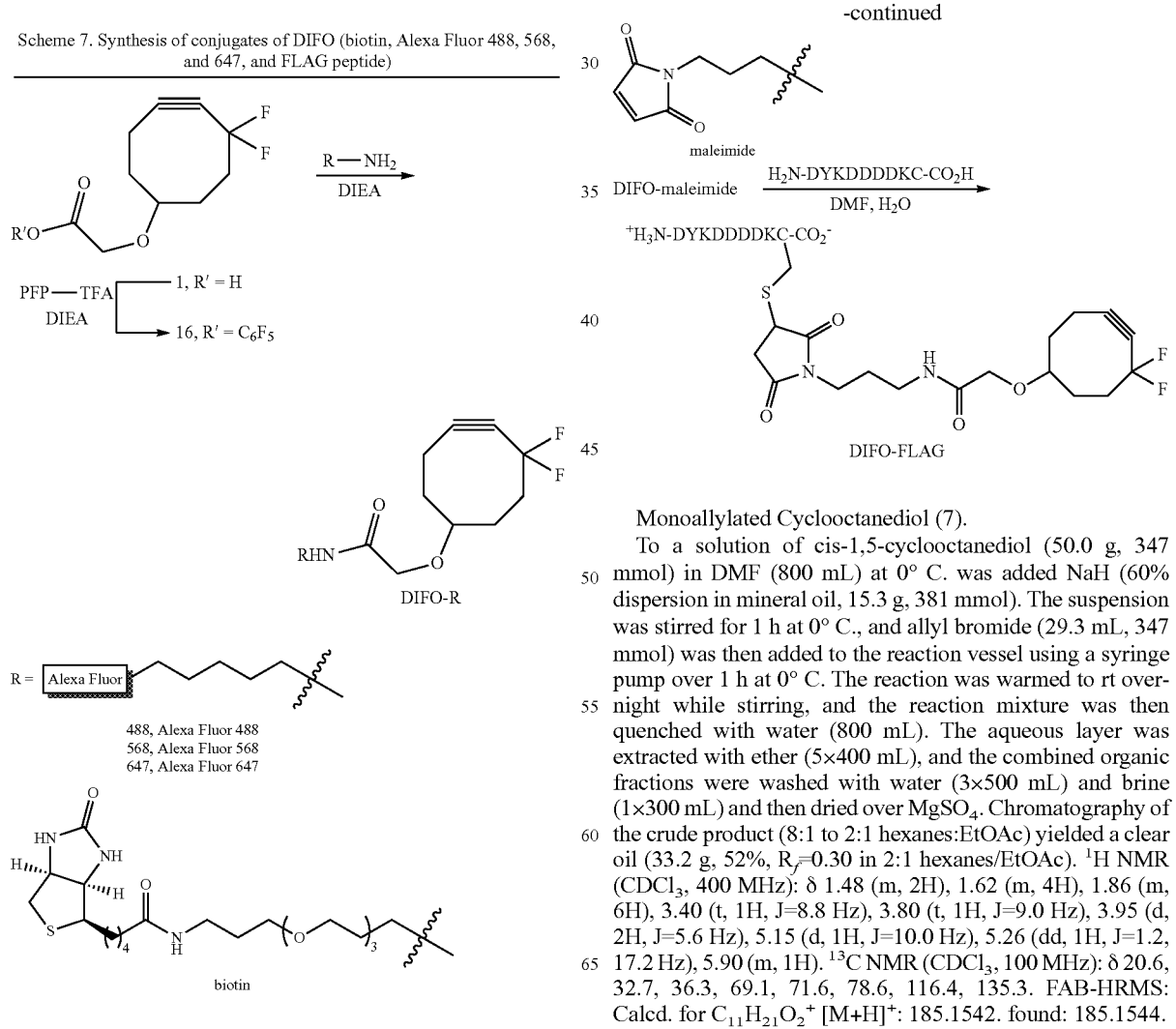

Monoallylated Cyclooctanediol (7).

To a solution of cis-1,5-cyclooctanediol (50.0 g, 347 mmol) in DMF (800 mL) at 0° C. was added NaH (60% dispersion in mineral oil, 15.3 g, 381 mmol). The suspension was stirred for 1 h at 0° C., and allyl bromide (29.3 mL, 347 mmol) was then added to the reaction vessel using a syringe pump over 1 h at 0° C. The reaction was warmed to rt overnight while stirring, and the reaction mixture was then quenched with water (800 mL). The aqueous layer was extracted with ether (5×400 mL), and the combined organic fractions were washed with water (3×500 mL) and brine (1×300 mL) and then dried over $MgSO_4$. Chromatography of the crude product (8:1 to 2:1 hexanes:EtOAc) yielded a clear oil (33.2 g, 52%, $R_f$=0.30 in 2:1 hexanes/EtOAc). $^1$H NMR ($CDCl_3$, 400 MHz): δ 1.48 (m, 2H), 1.62 (m, 4H), 1.86 (m, 6H), 3.40 (t, 1H, J=8.8 Hz), 3.80 (t, 1H, J=9.0 Hz), 3.95 (d, 2H, J=5.6 Hz), 5.15 (d, 1H, J=10.0 Hz), 5.26 (dd, 1H, J=1.2, 17.2 Hz), 5.90 (m, 1H). $^{13}$C NMR ($CDCl_3$, 100 MHz): δ 20.6, 32.7, 36.3, 69.1, 71.6, 78.6, 116.4, 135.3. FAB-HRMS: Calcd. for $C_{11}H_{21}O_2^+$ [M+H]$^+$: 185.1542. found: 185.1544.

Allylated Cyclooctanone (8).

To a stirring solution of alcohol 7 (33.2 g, 180 mmol) in $CH_2Cl_2$ (650 mL) at rt was added pyridinium chlorochromate (54.4 g, 252 mmol) over 2 h, 6.8 g every 15 min. After an additional 30 min of stirring, the reaction mixture was concentrated on a rotary evaporator and the product was purified directly by column chromatography (8:1 to 3:1 hexanes/EtOAc) to yield a clear oil (30.0 g, 91%, $R_f$=0.30 in 5:1 hexanes/EtOAc). $^1$H NMR ($CDCl_3$, 400 MHz): δ 1.63-1.90 (m, 6H), 2.04 (m, 2H), 2.28 (m, 2H), 2.55 (m, 2H), 3.16 (tt, 1H, J=2.8, 8.6 Hz), 3.89 (d, 1H, J=5.2 Hz), 5.13 (d, 2H, J=10.4 Hz), 5.22 (dd, 1H, J=1.2, 17.2 Hz), 5.85 (ddd, 1H, J=5.6, 10.4, 22.2 Hz). $^{13}$C NMR ($CDCl_3$, 100 MHz): δ 22.9, 33.7, 42.3, 69.5, 77.6, 116.7, 135.0, 216.5. FAB-HRMS: Calcd. for $C_{11}H_{19}O_2^+$ [M+H]$^+$: 183.1385. found: 183.1380.

Silyl Enol Ether (9).

To a stirring solution of Lithium hexamethyldisilazide (LHMDS, 181 mL, 181 mmol, 1.00 M solution in THF) in THF (750 mL) at −78° C. was added a solution of ketone 8 (30.0 g, 165 mmol) in THF (40 mL) over 1 h using a syringe pump. After an additional 20 min of stirring at −78° C., chlorotriethylsilane (31.8 mL, 189 mmol) was added. The solution was stirred at −78° C. for 10 min, removed from the cold bath, warmed to rt with a water bath, and stirred for 1 h. The reaction mixture was concentrated on a rotary evaporator and the crude product was purified directly by column chromatography (100% hexanes to 25:1 hexanes/EtOAc) to yield a clear oil (44.2 g, 91%, $R_f$=0.70 in 9:1 hexanes/EtOAc). $^1$H NMR ($CDCl_3$, 400 MHz): δ 0.67 (q, 6H, J=8.0 Hz), 0.98 (t, 9H, J=8.0 Hz), 1.52 (m, 2H), 1.70-2.01 (m, 5H), 2.13 (m, 2H), 2.26 (m, 1H), 3.40 (m, 1H), 3.95 (m, 2H), 4.76 (dd, 1H, J=7.2, 9.2 Hz), 5.14 (dd, 1H, J=1.6, 10.4 Hz), 5.26 (dd, 1H, J=1.8, 15.4 Hz), 5.91 (ddd, 1H, J=5.4, 10.6, 22.6 Hz). $^{13}$C NMR ($CDCl_3$, 100 MHz): δ 5.0, 6.7, 22.4, 24.5, 31.8, 33.7, 36.2, 69.2, 79.9, 104.3, 116.3, 135.5, 152.7. Calcd. for $C_{17}H_{33}O_2Si^+$ [M+H]$^+$: 297.2250. found: 297.2246.

Monofluoroketones (10a and 10b).

To a stirring solution of Selectfluor™ (63.4 g, 179 mmol) in DMF (150 mL) at 0° C. was added a solution of silyl enol ether 9 (44.2 g, 149 mmol) DMF (180 mL) via an addition funnel over 30 min. The reaction was allowed to slowly warm to rt while stirring over 30 min, and then it was quenched with water (350 mL). The aqueous layer was extracted with ether (4×350 mL), and the combined organic extracts were washed with water (3×300 mL), and brine (1×200 mL). The crude product was purified by column chromatography (10:1 to 5:1 hexanes/EtOAc) to yield two diastereomers, both clear oils (10a (cis), 19.5 g, 65%, $R_f$=0.40 in 9:1 hexanes/EtOAc and 10b (trans), 9.10 g, 30%, $R_f$=0.20 in 9:1 hexanes/EtOAc). Relative stereochemistry was assigned upon determination of the x-ray crystal structure of 11, a decomposition product of 10b (Supporting FIG. 6).

10a (trans): $^1$H NMR ($CDCl_3$, 400 MHz): 1.59 (m, 1H), 1.69 (m, 2H), 1.90 (m, 1H), 2.02 (m, 1H), 2.16-2.42 (m, 3H), 2.88 (m, 1H), 3.26 (m, 1H), 3.91 (m, 2H), 4.92 (ddd, 1H, J=2.6, 6.4, 50.4 Hz), 5.16 (dd, 1H, J=1.6, 10.4 Hz), 5.25 (dd, 1H, J=1.6, 17.2 Hz), 5.91 (ddd, 1H, J=5.2, 10.4, 22.4 Hz). $^{13}$C NMR ($CDCl_3$, 100 MHz): δ 20.1 (d, J=5 Hz), 27.2 (d, J=3 Hz), 30.7 (d, J=21 Hz), 33.4, 40.2, 69.4, 77.5, 95.8 (d, J=185 Hz), 116.8, 134.8, 213.5 (d, J=24 Hz). $^{19}$F NMR ($CDCl_3$, 376 MHz): δ −189.1 (app t, J=43 Hz) FAB-HRMS: Calcd. for $C_{11}H_{18}FO_2^+$ [M+H]$^+$: 201.1291. found: 201.1291.

10b (trans): $^1$H NMR ($CDCl_3$, 400 MHz): 1.62-1.91 (m, 4H), 1.93-2.11 (m, 3H), 2.27-2.55 (m, 3H), 3.35 (m, 1H), 3.92 (m, 2H), 4.99 (ddd, 1H, J=3.4, 6.8, 48.0 Hz), 5.15 (dd, 1H, J=1.6, 10.4 Hz), 5.24 (dd, 1H, J=1.8, 17.2 Hz), 5.91 (ddd, 1H, J=5.6, 10.8, 22.8 Hz). $^{13}$C NMR ($CDCl_3$, 100 MHz): δ 22.2, 26.6 (d, J=22 Hz), 27.0 (d, J=4 Hz), 31.7, 38.5, 69.5, 76.0, 93.9 (d, J=184 Hz), 116.8, 134.9, 210.3 (d, J=17 Hz). $^{19}$F NMR ($CDCl_3$, 376 MHz): δ −188.0 (app t, J=41 Hz) FAB-HRMS: Calcd. for $C_{11}H_{18}FO_2^+$ [M+H]$^+$: 201.1291. found: 201.1286.

Monofluoroketone (10b, trans).

To a stirring solution of compound 10a (26.5 g, 132 mmol) in THF (300 mL) at 0° C. was added KHMDS (2.64 mL, 1.32 mmol, 0.500 M solution in toluene). After 1 h, the reaction mixture was concentrated on a rotary evaporator and the crude product was purified by column chromatography (10:1 to 5:1 hexanes:EtOAc) to yield two diastereomers, both clear oils (10a, 14.4 g, 54%, and 10b, 11.8 g, 45%).

Fluorinated Silyl Enol Ether (12).

To a stirring solution of Potassium hexamethyldisilazide (KHMDS, 225 mL, 113 mmol, 0.500 M solution in toluene) in THF (800 mL) at −78° C. was added a solution of ketone 10b (18.8 g, 93.9 mmol) in THF (40 mL) dropwise, using a syringe pump, over 2 h. After an additional 30 min of stirring at −78° C., chlorotriethylsilane (20.5 mL, 122 mmol) was added. The solution was stirred at −78° C. for 30 min, removed from the cold bath, and stirred for 1 h at rt. The reaction mixture was concentrated on a rotary evaporator and the crude product was purified directly by column chromatography (100% hexanes to 25:1 hexanes/EtOAc) to yield a clear oil (28.7 g, 97% as a 5:1 mixture of desired:undesired regioisomers, $R_f$=0.70 in 9:1 hexanes/EtOAc). $^1$H NMR ($CDCl_3$, 400 MHz): δ 0.67 (q, 6H, J=8.0 Hz), 0.97 (t, 9H, J=8.0 Hz), 1.50-1.91 (m, 5H), 2.02-2.13 (m, 2H), 2.14-2.30 (m, 2H), 2.27-2.55 (m, 1H), 3.43 (m, 1H), 3.96 (m, 2H), 5.15 (dd, 1H, J=1.6, 10.4 Hz), 5.27 (dd, 1H, J=1.6, 17.2 Hz), 5.91 (ddd, 1H, J=5.2, 10.4, 22.4 Hz). $^{13}$C NMR ($CDCl_3$, 100 MHz): δ 5.2, 6.7, 24.5 (d, J=3 Hz), 24.5 (d, J=27 Hz), 31.2, 32.9, 33.5 (d, J=2 Hz), 69.3, 79.0, 104.3, 116.4, 128.6 (d, J=81 Hz), 135.2, 144.2 (d, J=239 Hz). $^{19}$F NMR ($CDCl_3$, 376 MHz): δ −129.5 (dd, J=21, 28 Hz).

Allylated Difluoroketone (13).

To a stirring solution of Selectfluor™ (35.8 g, 101 mmol) in DMF (100 mL) was slowly added a solution of silyl enol ether 12 (24.4 g, 77.7 mmol) in DMF (180 mL) over 30 min using an addition funnel, at 0° C. The reaction mixture was allowed to warm to rt, and, after 2 h of additional stirring, the reaction mixture was quenched with water (100 mL). The aqueous layer was extracted with ether (4×200 mL), and the combined organic extracts were washed with water (3×200 mL) and brine (1×100 mL) and then dried over $MgSO_4$. The crude product was purified by column chromatography (11:1 to 6:1 hexanes/EtOAc) to yield a clear oil (12.5 g, 74%, $R_f$=0.60 in 4:1 hexanes/EtOAc). $^1$H NMR ($CDCl_3$, 300 MHz): 1.65-1.93 (m, 5H), 2.04-2.20 (m, 2H), 2.27-2.47 (m, 1H), 2.48-2.61 (m, 1H), 2.75-2.85 (m, 1H), 3.35 (m, 1H), 3.92 (dt, 2H, J=1.4, 5.7 Hz), 5.17 (dd, 1H, J=1.4, 10.4 Hz), 5.25 (dd, 1H, J=1.5, 17.4 Hz), 5.91 (ddd, 1H, J=5.6, 10.8, 22.8 Hz). $^{13}$C NMR ($CDCl_3$, 100 MHz): δ 21.0, 25.9 (t, J=6 Hz), 31.0 (t, J=25 Hz), 31.4, 38.0, 69.4, 75.9, 116.9, 118.5 (t, J=250 Hz), 134.7, 203.4 (t, J=28 Hz). $^{19}$F NMR ($CDCl_3$, 376 MHz): δ −105.0 (app q, J=244 Hz) FAB-HRMS: Calcd. for $C_{11}H_{17}F_2O_2^+$ [M+H]$^+$: 219.1197. found: 219.1223.

Difluoroketone Carboxylic Acid (14).

To a stirring solution of alkene 13 (4.90 g, 22.5 mmol) in $CCl_4$ (45 mL), $CH_3CN$ (45 mL), and $H_2O$ (68 mL) at 0° C. in a three-necked flask equipped with an overhead stirrer was added $NaIO_4$ (19.3 g, 90.0 mmol) and $RuCl_3 \cdot H_2O$ (117 mg, 0.563 mmol). After 10 min of vigorous stirring at 0° C., the reaction was allowed to warm to rt. After an additional 2.5 h of vigorous stirring of the suspension at rt, the reaction mixture was concentrated on a rotary evaporator and diluted with 1 N HCl (200 mL) and brine (200 mL). The aqueous layer was extracted with CH$_2$Cl$_2$ (7×200 mL) and dried extensively over MgSO$_4$. The crude product was purified by column chromatography (4:1 to 1:1 hexanes/EtOAc, with 1% acetic acid) to yield a clear oil which turned to a white solid upon storage at −20° C. overnight (5.10 g, 96%, R$_f$=0.30 in 1:1 hexanes/EtOAc with 1% acetic acid). $^1$H NMR (CD$_3$CN, 400 MHz): 1.62-1.97 (m, 5H), 1.98-2.20 (m, 2H), 2.27-2.42 (m, 1H), 2.53 (m, 1H), 2.72 (m, 1H), 3.35 (tt, 1H, J=3.6, 7.6 Hz), 3.99 (s, 2H). $^{13}$C NMR (CD$_3$CN, 100 MHz): −22.1, 26.4 (t, J=6 Hz), 31.0 (t, J=25 Hz), 31.5, 38.4, 66.2, 78.6, 119.8 (t, J=248 Hz), 172.2, 204.2 (t, J=28 Hz). $^{19}$F NMR (CD$_3$CN, 376 MHz): δ −105.9 (app t, J=15 Hz) FAB-HRMS: Calcd. for C$_{10}$H$_{15}$F$_2$O$_4^+$ [M+H]$^+$: 237.0938. found: 237.0934.

Vinyl Triflate (15).

To a solution of KHMDS (106 mL, 52.9 mmol, 0.500 M solution in toluene) in THF (700 mL) was added a solution of ketone 14 (6.10 g, 25.8 mmol) in THF (20 mL) at −78° C. dropwise over 20 min. After an additional 1 h of stirring at −78° C., a solution of N-phenyl-bis(trifluoromethylsulfonamide) (Tf$_2$NPh, 18.9 g, 52.9 mmol) in THF (40 mL) was added and the reaction was allowed to warm to rt. After 30 min, the reaction mixture was concentrated on a rotary evaporator and the crude product was diluted with CH$_2$Cl$_2$ (200 mL), 1 N HCl (200 mL) and brine (200 mL). The aqueous layer was extracted with CH$_2$Cl$_2$ (5×150 mL) and dried extensively with MgSO$_4$. The crude product was purified by column chromatography (4:1 to 1:1 hexanes/EtOAc with 1% acetic acid) to yield the desired product (4.50 g, 47%, R$_f$=0.35 in 1:1 hexanes/EtOAc with 1% acetic acid) as a colorless oil. $^1$H NMR (CD$_3$CN, 400 MHz): δ 1.74 (m, 1H), 1.92 (m, 3H), 2.21-2.43 (m, 2H), 2.58-2.74 (m, 2H), 3.59 (tt, 1H, J=4.0, 7.8 Hz), 4.04 (d, 2H, J=1.6 Hz), 6.35 (td, 1H, J=2.8, 9.6 Hz). $^{13}$C NMR (CD$_3$CN, 100 MHz): δ 19.8, 26.4 (t, J=2 Hz), 31.7, 32.1 (t, J=25 Hz), 66.4, 77.6, 119.8 (t, J=237 Hz), 130.6 (t, J=5 Hz), 143.0 (t, J=29 Hz), 172.2. $^{19}$F NMR (CD$_3$CN, 376 MHz): δ −74.4 (s, 3F), −89.2 (dd, 2F, J=30, 273 Hz), −92.6 (dd, 2F, J=30, 273 Hz). FAB-HRMS: Calcd. for C$_{11}$H$_{13}$F$_5$O$_6$SLi$^+$ [M+H]$^+$: 375.0513. found: 375.0509.

DIFO (1).

To a solution of diisopropylamine (10.1 mL, 71.3 mmol) in THF (86 mL) at −78° C. was added nBuLi (23.8 mL, 59.4 mmol, from a 2.5 M solution in hexanes) dropwise and stirred at −78° C. for 45 min. In a separate flask, a solution of vinyl triflate 15 (7.31 g, 19.8 mmol) in THF (400 mL) was prepared and kept at −15° C. using a MeOH/ice bath. LDA was added to this solution dropwise, via syringe pump, at the rate of 1.0 equiv (~40 mL of the solution prepared above) per 30 min, with vigorous stirring, until 2.5 equiv of LDA was added. Note: the colour of the solution turned from clear to yellow to amber. The reaction mixture was quenched by the addition of 10 mL of saturated ammonium chloride solution and then the solvent was removed by rotary evaporation. To the residue was added CH$_2$Cl$_2$ (100 mL), 1 N HCl (50 mL), and brine (50 mL). The aqueous layer was extracted with CH$_2$Cl$_2$ (5×40 mL) and washed extensively with MgSO$_4$. The crude product was purified by column chromatography (4:1 to 1:1 hexanes/EtOAc with 1% acetic acid) to yield the desired product (466 mg, 11%, R$_f$=0.35 in 1:1 hexanes/EtOAc with 1% acetic acid) as a colorless oil. $^1$H NMR (CD$_3$CN, 400 MHz): δ 1.94 (m, 1H), 2.07 (m, 1H), 2.11-2.33 (m, 3H), 2.41 (m, 1H), 2.52 (m, 2H), 3.55 (app t, J=7.2 Hz, 1H), 4.05 (s, 2H). $^{13}$C NMR (CD$_3$CN, 100 MHz): δ 17.6, 34.4 (d, J=6 Hz), 39.2, 43.2 (t, J=28 Hz), 66.2, 84.4, 85.2 (dd, J=48, 43 Hz), 113.9 (t, J=11 Hz), 120.5 (t, J=233 Hz), 172.2. $^{19}$F NMR (CD$_3$CN, 376 MHz): δ −86.6 (dddt, J=259.0, 26.0, 12.8, 6.0 Hz, 1F), −88.6 (dm, J=260.9 Hz, 1F). FAB-HRMS: Calcd. for C$_{10}$H$_{12}$F$_2$O$_3$Li$^+$ [M+H]$^+$: 225.0915. found: 225.0912.

General Procedure for Synthesis of Conjugates of DIFO (5a-f).

The pentafluorophenyl ester of DIFO (16) was prepared as follows and used immediately. DIFO (1, 1.0 equiv) was dissolved in CH$_2$Cl$_2$ (final concentration of 0.1-0.2 M) and N,N-diisopropylethylamine (2.0 equiv) was added. The solution was cooled to 0° C. and pentafluorophenyltrifluoroacetate (1.05 equiv) was added dropwise. After 1 h, the solvent and residual pentafluorophenol was removed on a rotary evaporator. The crude product was either used immediately or quickly purified by column chromatography (R$_f$=0.3 in 9:1 hexanes:ethyl acetate) and then used immediately. $^1$H NMR (CD$_3$CN, 400 MHz): δ 1.99 (m, 1H), 2.09 (m, 1H), 2.15-2.35 (m, 3H), 2.43 (m, 1H), 2.54 (m, 2H), 3.63 (app t, J=7.2 Hz, 1H), 4.53 (s, 2H). $^{19}$F NMR (CD$_3$CN, 376 MHz): δ −86.6 (dddt, J=259.0, 26.0, 12.8, 6.0 Hz, 1F), −88.6 (dm, J=260.9 Hz, 1F), −153.6 (d, J=19 Hz, 2F), −159.2 (t, 21 Hz, 1F), −163.6 (dd, J=17, 4 Hz, 2F).

Synthesis of Alexa Fluor Derivatives (5a, DIFO-488; 5d, DIFO-568; 5e, DIFO-647; 6a, Alk-488).

To a solution of the appropriate Alexa Fluor cadaverine (1.0 equiv) in DMF (final concentration of 0.2 M) was added a solution of the pentafluorophenyl ester of DIFO (16) or 4-pentynoic acid (2.0 equiv) and then N,N-diisopropylethylamine (5.0 equiv). The solution was stirred at rt overnight in the dark, and then the solvent was removed on a rotary evaporator. The residue was dissolved in water or 9:1 water:acetonitrile, purified by reversed phase HPLC using water and acetonitrile, and lyophilized to a fine powder.

DIFO-488, FT-ICR-MS: Calcd. for C$_{36}$H$_{36}$F$_2$N$_4$O$_{12}$S$_2^+$ [M$^+$]: 818.1739. found: 818.1725.

DIFO-568, FT-ICR-MS: Calcd. for C$_{48}$H$_{52}$F$_2$N$_4$O$_{12}$S$_2^+$ [M$^+$]: 978.2986. found: 978.2971.

DIFO-647, FT-ICR-MS. Found: 1142.3509.

Alk-488, FT-ICR-MS: Calcd. for C$_{31}$H$_{30}$N$_4$O$_{11}$S$_2^+$ [M$^+$]: 698.1352. found: 698.1318.

DIFO-biotin (5b).

To a solution of biotin-PEG-amine (2) (15 mg, 0.034 mmol) in DMF (0.5 mL) was added a solution of pentafluorophenyl ester 16 (13 mg, 0.034 mmol) in DMF (1.0 mL) and then N,N-diisopropylethylamine (9.0 µL, 0.051 mmol). The solution was stirred overnight at rt, the DMF was removed on a rotary evaporator, and the residue was purified by silica gel chromatography (100% CH$_2$Cl$_2$ to 9:1 CH$_2$Cl$_2$:MeOH) to yield 19 mg (87%) of a clear oil (R$_f$ in 9:1 CH$_2$Cl$_2$: MeOH=0.40). $^1$H NMR (MeOD, 500 MHz): δ 1.43 (m, 2H), 1.55-1.70 (m, 3H), 1.71-1.83 (m, 5H), 1.95 (m, 1H), 2.07-2.35 (m, 4H), 2.18 (t, J=8.0 Hz, 2H), 2.43 (m, 1H), 2.52 (m, 2H), 2.70 (d, J=12.5 Hz, 1H), 2.92 (dd, J=12.5, 5.0 Hz, 1H), 3.20 (m, 1H), 3.26 (t, J=6.8 Hz, 2H), 3.34 (t, J=6.8 Hz, 2H), 3.53 (m, 5H), 3.59 (m, 4H), 3.64 (m, 4H), 3.95 (d, J=3.5 Hz, 2H), 4.30 (dd, J=7.5, 4.5 Hz, 1H), 4.49 (dd, J=7.5, 5.0 Hz, 1H). $^{13}$C NMR (MeOD, 125 MHz): δ 18.2, 27.4, 30.0, 30.3, 30.9, 35.3 (d, J=6 Hz), 37.4, 38.3 (d, J=4 Hz), 40.3, 41.6, 44.2 (t, J=28 Hz), 57.5, 62.1, 63.9, 69.4, 70.4, 70.8, 71.8, 72.0, 72.1, 85.2, 86.4 (dd, J=48, 42 Hz), 113.9 (t, J=11 Hz), 120.5 (t, J=234 Hz), 166.6, 172.9, 176.5. $^{19}$F NMR (MeOD, 376 MHz): δ −88.0 (dddt, J=266.5, 26.3, 12.4, 6.0 Hz, 1F), −90.0 (dm, J=259.4 Hz, 1F). FAB-HRMS: Calcd. for C$_{30}$H$_{48}$F$_2$N$_4$O$_7$SLi$^+$ [M+H]$^+$: 653.3372. found: 653.3379.

Maleimide-amine (17).

A dry 500 mL round-bottom flask was charged with maleimide (3.12 g, 32.2 mmol) and triphenylphosphine (8.29 g, 31.6 mmol), and then THF (150 mL). N-(tert-Butoxycarbonyl)ethanolamine (5.00 mL, 29.3 mmol) and diisopropylazidodicarboxylate (6.80 mL, 35.1 mmol) were added in succession. The flask was stirred under a nitrogen atmosphere overnight, the reaction mixture was concentrated on a rotary evaporator, and the crude product was filtered through a plug of silica gel using a 2:1 mixture of hexanes:ethyl acetate as the eluent. The crude product was dissolved in 100 mL of a 60:35:5 mixture of $CH_2Cl_2$:trifluoroacetic acid:water and stirred at rt for 2 h. The reaction mixture was diluted with $CH_2Cl_2$ (50 mL) and water (50 mL), transferred to a separatory funnel, and the organic layer was extracted with water (3×25 mL). The combined aqueous layers were washed with $CH_2Cl_2$ (3×50 mL) and concentrated on a rotary evaporator to yield the desired product (7.51 g, 96%) as a yellow oil. $^1H$ NMR (DMSO-$d_6$, 400 MHz): δ 1.76 (app quintet, 2H, J=7.2 Hz), 2.76 (m, 2H), 3.45 (t, 2H, J=6.8 Hz), 7.02 (s, 2H), 7.79 (br s, 3H). $^{13}C$ NMR (DMSO-$d_6$, 100 MHz): δ 26.7, 34.6, 37.0, 115.6 (q, J=290 Hz), 134.7, 158.9 (q, J=36 Hz), 171.3. $^{19}F$ NMR (DMSO-$d_6$, 376 MHz): δ −73.9.

DIFO-maleimide (5f).

To a solution of maleimide-amine 17 (74 mg, 0.27 mmol) in $CH_2Cl_2$ (1.5 mL) was added N,N-diisopropylethylamine (160 µL, 0.91 mmol). The solution was cooled to 0° C. and then a solution of pentafluorophenyl ester 16 (97 mg, 0.23 mmol) in $CH_2Cl_2$ (1 mL) was added dropwise. The reaction mixture was stirred for 2 h, the solvent was removed on a rotary evaporator, and the residue was purified by silica gel chromatography (2:1 to 1:3 hexanes:ethyl acetate) to yield 62 mg (76%) of a clear oil ($R_f$=0.20 in 1:1 hexanes:ethyl acetate). $^1H$ NMR (CDCl$_3$, 500 MHz): δ 1.81 (app q, J=6.5 Hz, 2H), 2.05-2.31 (m, 5H), 2.48 (m, 2H), 2.60 (m, 1H), 3.26 (t, J=6.5 Hz, 2H), 3.55 (t, J=6.8 Hz, 1H), 3.60 (t, J=6.5 Hz, 2H), 3.95 (dd, J=20.5, 15.0 Hz, 2H), 6.74 (s, 2H), 7.12 (br s, 1H). $^{19}F$ NMR (CD$_3$CN, 376 MHz): 6-86.6 (dddt, J=266.5, 26.3, 12.4, 6.0 Hz, 1F), −88.5 (dm, J=259.4 Hz, 1F).

DIFO-FLAG (5c).

Cysteine-modified FLAG peptide (FLAG-C, $H_2$N-DYKD-DDDKC-CO$_2$H) was synthesized using established automated protocols on a Perkin-Elmer ABI 431 A peptide synthesizer using fluorenylmethoxycarbonyl (Fmoc)-Cys(Trt)-Wang resin (Novabiochem). The peptide was cleaved using a solution of trifluoroacetic acid:triisopropylsilane:water (95:2.5:2.5), precipitated with ether, and the crude product was dried and used without further purification. To a solution of FLAG-C (214 mg, 0.192 mmol) in 1 mL of water was added a solution of DIFO-maleimide (5f, 62 mg, 0.175 mmol) in 1 mL of DMF at 0° C. The reaction mixture was allowed to warm to rt and stir overnight. The solvents were removed on a rotary evaporator and the residue was purified by reversed phase HPLC (5% to 40% acetonitrile in water over 60 min, product eluting at 30-35 min) and lyophilized to yield 125 mg (49%) of a white solid. MALDI-TOF: Calcd. [M+H]$^+$: 1470.5540. found: 1470.5526.

Kinetic Evaluation of the [3+2] Cycloaddition of DIFO and Benzyl Azide

Stock solutions of DIFO (1, 20 mM) and benzyl azide (200 mM) were made in CD$_3$CN. An NMR tube was charged with 450 µL of the solution of 1, and, immediately before lowering into the NMR magnet, 50 µL of the benzyl azide solution, and the reaction was monitored over time using $^1H$ NMR spectroscopy. The kinetic data were derived by monitoring the change in integration of resonances corresponding to the benzylic protons in benzyl azide (δ ~4.4 ppm) compared to the corresponding resonances of the triazole products (δ ~5.5 to 5.7 ppm). The second-order rate constant for the reaction was determined by plotting 1/[benzyl azide] versus time, followed by subsequent analysis by linear regression The second-order rate constant (k, $M^{-1}s^{-1}$) corresponds to the determined slope.

In Vivo Labeling of Glycoproteins with Azido Sugars and DIFO-FLAG.

For in vivo metabolic labeling experiments, B6D2F1 mice were administered daily doses of Ac$_4$ManNAz (300 mg/kg in ~150 µL of 70% DMSO, from a stock solution of 50 mg/mL) intraperitoneally (i.p.) for 7 d as previously described (Prescher et al. Nature 2004). Sixteen to 24 h after the final azidosugar bolus, mice were injected i.p. with DIFO-FLAG (5c, 0.16 mmol kg$^{-1}$ in 70% DMSO) or vehicle (70% DMSO). After 3 h, the mice were sacrificed and organs were harvested.

To determine the extent of ligation of azides with DIFO-FLAG in vivo, splenocytes from B6D2F1 mice treated with the appropriate combination of Ac$_4$ManNAz, DIFO-FLAG or vehicle (70% DMSO), as described above, were isolated and probed for the presence of cell-surface Flag epitopes using a flow cytometry assay. Briefly, splenocytes from one spleen were suspended in RPMI medium 1640 and distributed among wells of a 96-well V-bottom tissue culture plate (three wells per treatment, ~5×10$^5$ cells/well). The cells were pelleted, rinsed with labeling buffer (PBS, pH 7.4 containing 1% FBS), and incubated with a FITC-conjugated anti-FLAG antibody (1:900 dilution) in labeling buffer for 30 min on ice. All cells were analyzed by flow cytometry.

Figure 9:
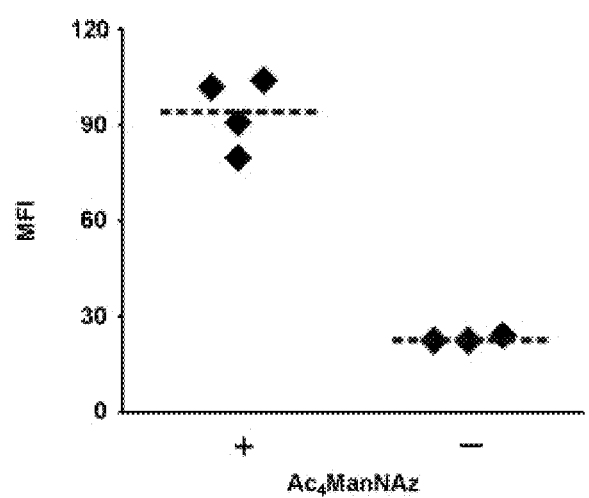
FIG. 9 depicts in vivo reaction of DIFO-FLAG with metabolically labeled azido glycans.

The data are shown in FIG. 9. FIG. 9 depicts in vivo reaction of DIFO-FLAG with metabolically labeled azido glycans. MFI, mean fluorescence intensity. B6D2F1 mice were injected once daily for 7 days with 300 mg/kg Ac$_4$ManNAz in 70% DMSO (+) or vehicle (−). On the eighth day, the mice were injected with a single bolus of DIFO-FLAG in PBS (0.16 mmol/kg) or vehicle and sacrificed 3 hours post-injection. Splenocytes were harvested, stained with FITC-labeled anti-FLAG antibody, and analyzed by flow cytometry. Shown is the mean fluorescence intensity (MFI, in arbitrary units). Each diamond represents data from a single mouse.

The data presented in FIG. 9 demonstrate that DIFO-FLAG can selectively label azide-containing glycans inside a living mouse, specifically in the cells of the spleen.

Comparative Labeling of Azido Proteins by Cu-Free and Cu-Catalyzed Click Chemistries.

Recombinant murine dihydrofolate reductase was expressed with (azido-DHFR) or without (DHFR) replacement of its methionine residues by azidohomoalanine as previously described (Kiick et al. Proc. Natl. Acad. Sci. U.S.A. 2002) and stock solutions were normalized to 0.1 mg/mL in PBS in 1% sodium dodecylsulfate (SDS). Stock solutions were made of DIFO-488 and alk-488 in PBS (1 mM), CuSO$_4$ in water (20 mM), tris(2-carboxyethyl)phosphine hydrochloride (TCEP) in water (20 mM), and tris-triazolyl ligand (TBTA, 1.7 mM in 4:1 t-butanol:dimethylsulfoxide (DMSO)). Reactions were performed in 10 µL volumes at final concentrations of the following reagents: 1 µg/mL azido-DHFR or DHFR, 25 µM of DIFO-488 or alk-488, 0.04% SDS, 1×PBS, pH 7.4. In addition, in accordance with conditions optimized by Speers and Cravatt ((2004) Chem. Biol. 11:535-46), the Cu-catalyzed reactions with alk-488 also contained CuSO$_4$ (1 mM), TCEP (1 mM), and TBTA (100 µM), such that the final concentrations of t-butanol and DMSO were 4.8% and 1.2%, respectively) (28). The order of addition was as follows: (a) Cu-free click chemistry, PBS, azido-DHFR or DHFR, and DIFO-488; (b) Cu-catalyzed click chemistry, PBS, azido-DHFR or DHFR, alk-488, TCEP, ligand, and CuSO$_4$. Reactions were started by addition of the final reagent, briefly vortexed, and allowed to sit in the dark at rt for 0-60 min. Reactions were quenched by the sequential addition of 1 µL of a solution of 2-azidoethanol in water (500 mM) and 11 µL of a solution of urea in water (8 M) for final concentrations of 23 mM and 4 M, respectively, followed by brief vortexing and an additional hour in the dark at rt. (For t=0 min, the 2-azidoethanol and urea were added to the reaction mixture after the protein was added, followed by brief vortexing, and before the other reagents.) SDS protein loading buffer containing β-mercaptoethanol (4×, 7.3 µL) was added, the samples were heated at 100° C. for 10 min, and loaded onto 12% Bis-Tris Criterion polyacrylamide gel (Bio-Rad). After electrophoresis, gels were rinsed in a destain solution (5:4:1 water:methanol:acetic acid) overnight (in the dark) and fluorescence intensities were measured using a Typhoon 9410 (GE Healthcare). Equal protein loading was confirmed using silver stain (Bio-Rad).

Figure 10:
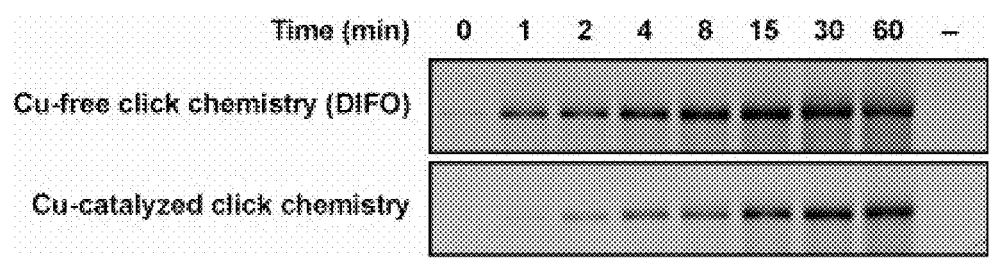
FIG. 10 depicts time-dependent labeling of an isolated azidoprotein by Cu-catalyzed (lower panedl) or Cu-free (DIFO; upper panel) click chemistry, using Alexa Fluor 488 derivatives.

The data are presented in FIG. 10. FIG. 10 depicts time-dependent labeling of an isolated azidoprotein by Cu-catalyzed (lower panedl) or Cu-free (DIFO; upper panel) click chemistry, using Alexa Fluor 488 derivatives. Recombinant murine dihydrofolate reductase was expressed in *E. coli* with media supplemented either with methionine (−) or azidohomoalanine (all other lanes), and purified (see Kiick et al. (2002) *Proc. Natl. Acad. Sci. U.S.A* 99:19). The purified protein was reacted for various times (0-60 min) with an Alexa Fluor 488 cadaverine derivative of the difluorinated cyclooctyne DIFO ("Cu-free click chemistry") or pentynoic acid ("Cu-catalyzed chemistry") for the indicated times. In the case of Cu-catalyzed click chemistry, the reaction was supplemented with 1 mM $CuSO_4$, 1 mM TCEP, and 100 µM of the tris-triazolyl ligand TBTA according to the conditions of Speers and Cravatt (2004) *Chem. Biol.* 11:535-46. The reactions were performed in PBS, quenched by the addition of 8 M urea and 10 mM azidoethanol, and analyzed by SDS-PAGE and in-gel fluorescence measurement.

The data presented in FIG. 10 demonstrate that DIFO can selectively label an azide-containing isolated protein with similar reaction kinetics to copper-catalyzed click chemistry using terminal alkynes, Cu(I) salts, TCEP, and the tris-tra-zolyl ligand TBTA.

Cell Surface Labeling of Azido Glycans on Jurkat Cells with Biotinylated Conjugates.

Jurkat (human T-cell lymphoma) and Chinese hamster ovary (CHO) cells were maintained in a 5% $CO_2$, water-saturated atmosphere and grown in RPMI-1640 (Jurkat) or F12 (CHO) media supplemented with 10% FCS, penicillin (100 units/mL), and streptomycin (0.1 mg/mL). Cell densities were maintained between $1\times10^5$ and $1.6\times10^6$ cells/mL.

Jurkat cells were incubated for 1-3 d in untreated media or media containing 25 µM $Ac_4ManNAz$. The cells were then distributed into a 96-well V-bottom tissue culture plate, pelleted (3500 rpm, 3 min), and washed twice with 200 µL of labeling buffer (PBS, pH 7.4 containing 1% FCS). Cells were then incubated with DIFO-biotin or a similar biotinylated analog of a nonfluorinated or a triaryl phosphine capable of Staudinger ligation in labeling buffer for 1 h at rt at various concentrations (10 nM to 100 µM) with dilutions made from a 2.5 mM stock in 7:3 PBS:DMF. After incubation, cells were pelleted, washed twice with labeling buffer, and resuspended in the same buffer containing fluorescein isothiocyanate (FITC)-avidin (1:200 dilution of the Sigma stock). After a 15-min incubation on ice (in the dark), the cells were washed once with 200 µL, incubated with FITC-avidin for an additional 15 min on ice, washed twice with 200 µL of cold labeling buffer, and then diluted to a volume of 400 µL for flow cytometry analysis.

Figures 11A, 11B:
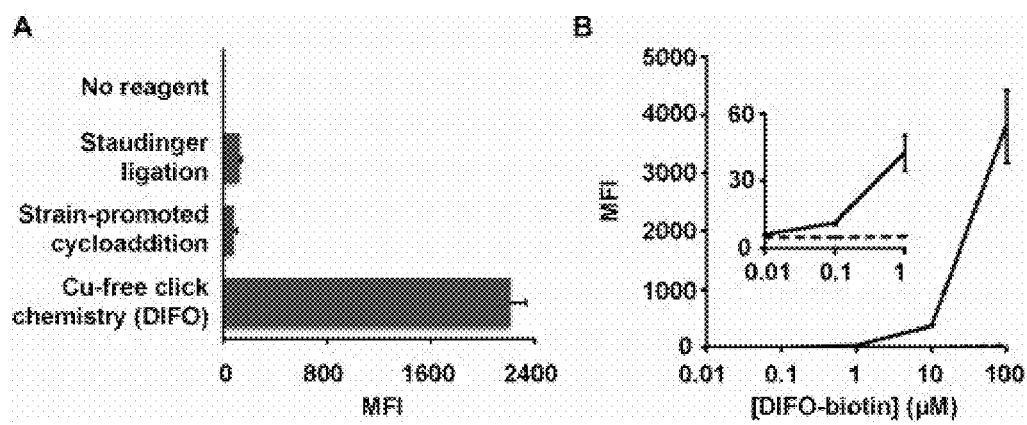
FIGS. 11A and 11B depict cell surface labeling of azido glycans by various biotinylated derivatives of cyclooctynes or phosphines.

The data are shown in FIGS. 11A and 11B. FIGS. 11A and 11B depict cell surface labeling of azido glycans by various biotinylated derivatives of cyclooctynes or phosphines. Jurkat cells were incubated with 0 or 25 µM $Ac_4ManNAz$ for 3 days. (A) The cells were then reacted with 100 µM phosphine-biotin (Vocadlo et al. *Proc. Natl. Acad. Sci. U.S.A.* 2003, 100, 9116-9121), cyclooctyne-biotin, or DIFO-biotin for 1 h. (B) The cells were reacted with various concentrations of DIFO-biotin for 1 h. In both cases, the cells were then stained with FITC-avidin, and analyzed by flow cytometry. Shown is the mean fluorescence intensity (MFI, arbitrary units). Error bars represent the standard deviation of triplicate samples.

The data presented in FIGS. 11A and 11B show that DIFO-biotin can selectively label azide-containing membrane-associated glycans in live cells; further, the sensitivity of azide detection is much higher using DIFO than a nonfluorinated cyclooctyne or a phosphine capable of Staudinger ligation.

Cell Surface Labeling of Azido Glycans on CHO Cells and Imaging by Fluorescence Microscopy.

CHO cells were incubated for 2 d in media containing 100 µM $Ac_4ManNAz$ or $Ac_4ManNAc$ in an eight-well LabTek II chambered coverglass (Nunc). The media was gently aspirated and the cells were washed three times with 600 µL of complete media. The cells were then treated with a solution of DIFO-488, DIFO-568, or DIFO-647, diluted from a 1 mM stock solution in PBS (pH 7.4), in media for varying times (0-60 min) at varying concentrations (10-100 µM) and temperatures (4-37° C.). For long time-course labeling studies, the cells were washed with 600 µL of media three times after the labeling reaction and returned to media containing 100 µM $Ac_4ManNAz$ or $Ac_4ManNAc$ until the next labeling reaction. Immediately prior to imaging, the cells were treated with Hoechst 33342 dye to stain the nucleus (1:1000 dilution in media of a 1 mg/mL stock solution in DMSO) for 1 min at rt, washed twice with 600 µL of media, and imaged. Optimized conditions for exclusive cell surface labeling: (a) 100 µM DIFO-488 for 1 min in media pre-warmed to 37° C., or (b) 100 µM DIFO-488 for 1 h in media at 4° C. Optimized conditions for cell surface and Golgi labeling: 10 µM DIFO-488 for 1 h in media at 37° C. For experiments with intracellular organelle markers for lysosomes (LysoTracker Red™, Invitrogen) and Golgi (BODIPY TR ceramide, Invitrogen) instructions provided by the manufacturer were utilized. Propidium iodide, used to stain for cell viability, was applied (1:3000 dilution in media of a 1 mg/mL stock solution in water for 3 min at rt) immediately prior to imaging, after application of Hoechst dye; the cells were then washed twice with 600 µL of media and imaged.

The data demonstrate that DIFO-Alexa Fluor conjugates can selectively label azide-containing membrane-associated glycans on CHO cell surfaces, e.g., for the purposes of imaging the dynamics of these biomolecules in live cells on the minute and hour timescale.

Example 6

Synthesis and Characterization of Difluorinated Cycloocytyne

The following schemes depict synthesis of DIFO2 and DIFO3, and synthesis of biotin conjugates of DIFO2 and DIFO3.

Scheme 8. Synthesis of DIFO2 (7).
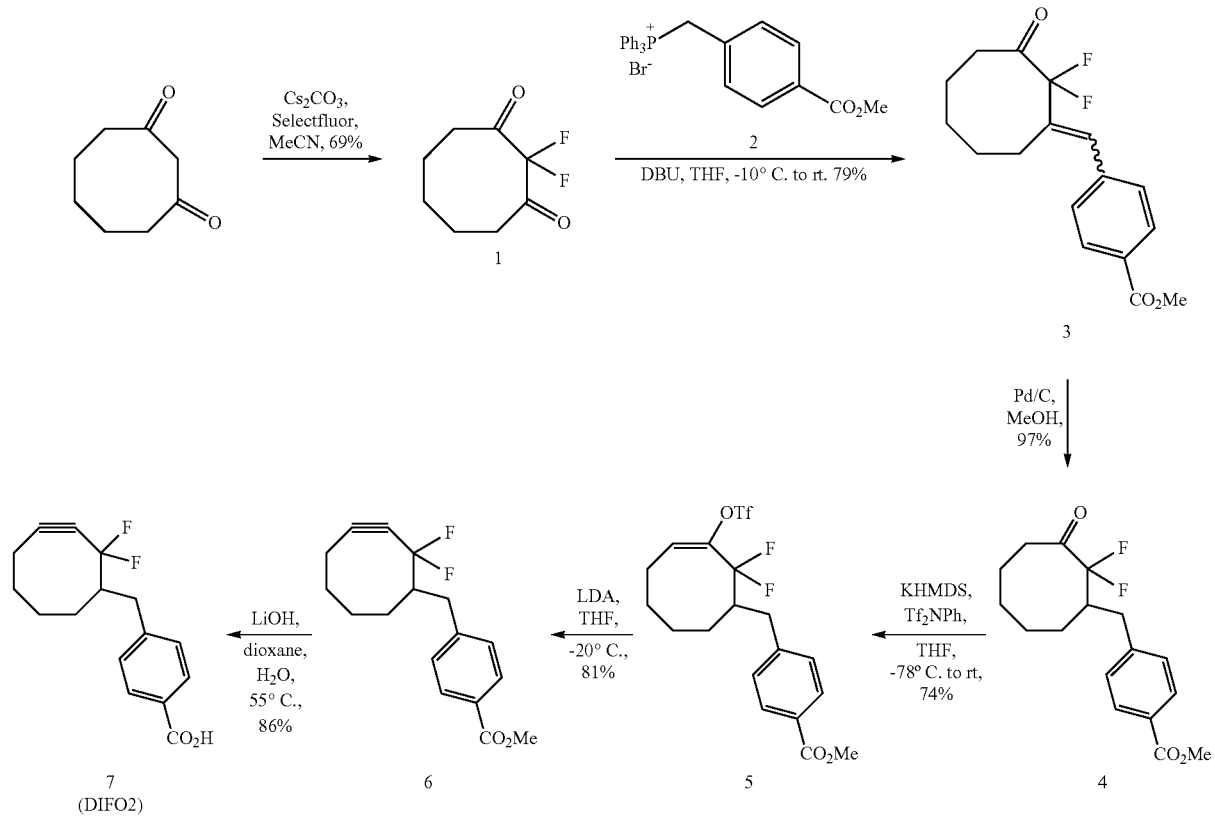
Scheme 9. Synthesis of DIFO3 (12).
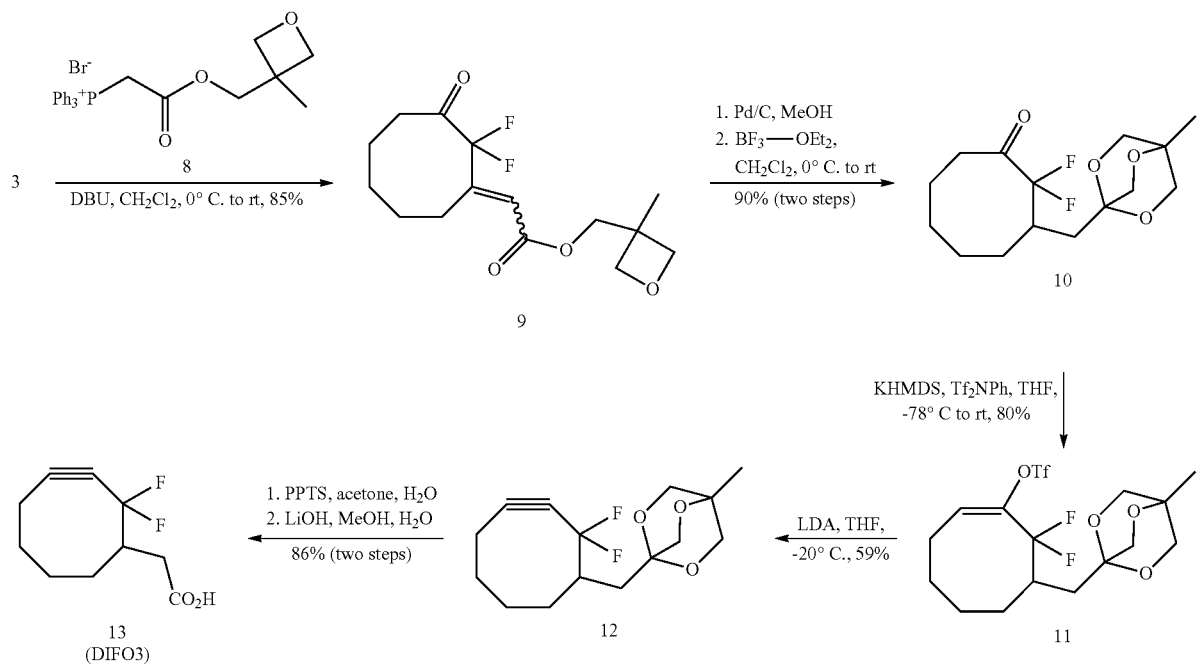

Scheme 10. Synthesis of biotin conjugates of DIFO2 and DIFO3.

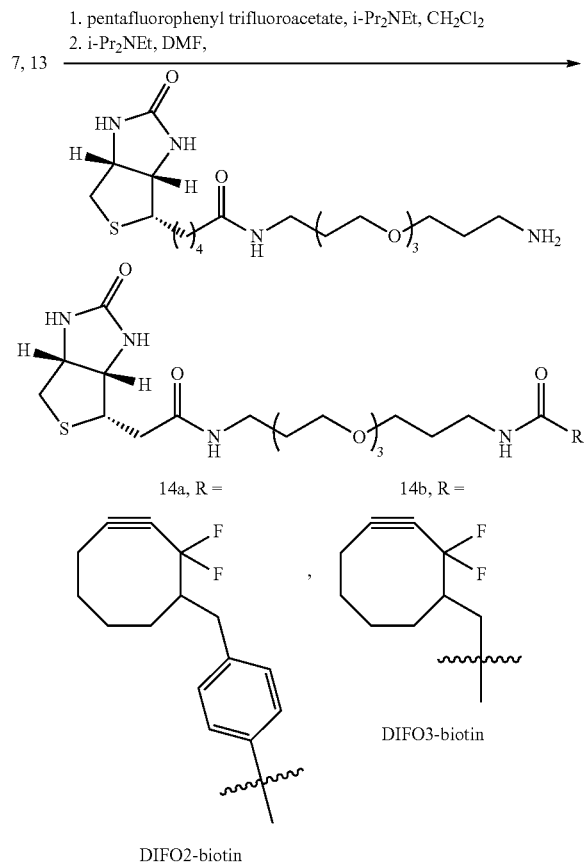

Synthesis of DIFO2 (7) and DIFO3 (13)

1. A solution of 1,3-cyclooctanedione (1.80 g, 12.8 mmol) in MeCN (90 mL) was transferred to a flame-dried round bottom flask under an $N_2$ atmosphere, and the system was cooled to 0° C. with stirring. $Cs_2CO_3$ (8.58 g, 26.3 mmol) was added, followed 15 min later by Selectfluor™ (10.9 g, 30.8 mmol), and the reaction mixture was stirred for an additional 15 min. The system was then allowed to warm to rt and was stirred for 6 h, concentrated under reduced pressure, and diluted with 1 M HCl (150 mL). The resulting mixture was extracted with diethyl ether (120 mL, 4×), and the combined organic layers were washed with brine (200 mL), dried over $MgSO_4$, and filtered through a glass frit. The solution was then concentrated under reduced pressure and purified by flash chromatography (4:1 hexanes:EtOAc) to yield a white solid (1.57 g, 69%). $R_f$=0.40 (4:1 hexanes:EtOAc); mp 42.7-43.7° C.; $^1$H NMR (500 MHz, $CDCl_3$) δ 2.67 (m, 4H), 1.81 (m, 4H), 1.63 (m, 2H) ppm; $^{13}$C NMR (125 MHz, $CDCl_3$) δ 197.9 (t, J=25.1 Hz), 109.5, 38.7, 26.2, 24.7 ppm; $^{19}$F NMR (376 MHz, $CDCl_3$) δ −118.35 (s, 2F) ppm; HRMS (EI$^+$) calcd for $C_8H_{10}O_2F_2$ 176.0649. found 176.0646.

3. To a flame-dried round bottom flask were added difluorodiketone 1 (998 mg, 5.67 mmol), phosphonium iodide 2 (5.57 g, 11.34 mmol), and THF (100 mL). A $N_2$ atmosphere was established, and the system was cooled to 0° C. DBU (1.27 mL, 8.51 mmol) was added, and the reaction mixture was stirred for 20 min at 0° C. and then brought to rt. The reaction was stirred an additional 24 h, quenched with MeOH (10 mL), concentrated under reduced pressure, and purified by flash chromatography (20-75% toluene:hexanes) to yield a white solid (1.38 g, 79%). $R_f$=0.55 (4:1 hexanes:EtOAc); mp 58.8-61.1° C.; $^1$H NMR (400 MHz, $CDCl_3$) δ 8.05 (d, 2H, J=8.4 Hz), 7.38 (d, 2H, J=8.2 Hz), 7.23 (s, 1H), 3.92 (s, 3H), 2.70 (t, 2H, J=6.6 Hz), 2.52 (apt t, 2H, 6.2 Hz), 1.86 (m, 2H), 1.53 (m, 4H) ppm; $^{13}$C NMR (125 MHz, $CDCl_3$) δ 202.1 (t, J=28.9 Hz), 166.8, 140.0, 134.6 (t, J=19.6 Hz), 131.2 (t, J=10.3 Hz), 130.0, 129.7, 129.0, 115.2 (t, J=253.4 Hz), 52.4, 37.5, 27.3, 26.0, 25.7, 25.3 ppm; $^{19}$F NMR (376 MHz, $CDCl_3$) δ −111.09 (s, 2F) ppm; HRMS (FAB) calcd for $C_{17}H_{18}O_3F_2$ [M+H]$^+$ 309.1302. found 309.1302.

4. To a round bottom flask were added olefin 3 (1.11 g, 3.60 mmol) and MeOH (40 mL). The system was flushed with $N_2$ and a catalytic amount of Pd/C was added. The system was again flushed with $N_2$ followed by $H_2$, and the reaction was stirred under a $H_2$ atmosphere for 1.5 h. The system was then flushed with $N_2$ and the reaction was diluted with $CH_2Cl_2$ (40 mL), filtered through Celite, and concentrated under reduced pressure. The crude product was purified by flash chromatography (33-75% toluene:hexanes) to yield a white solid (1.09 g, 97%). $R_f$=0.60 (4:1 hexanes:EtOAc); mp 70.1-71.4° C.; $^1$H NMR (400 MHz, $CDCl_3$) δ 7.99 (dm, 2H, J=8.3 Hz), 7.27 (d, 2H, J=8.14 Hz), 3.92 (s, 3H), 3.31 (dd, 1H, J=13.6, 2.9 Hz), 2.82-2.73 (m, 1H), 2.66-2.48 (m, 2H), 2.45-2.28 (m, 1H), 2.17-2.02 (m, 1H), 1.97-1.84 (m, 1H), 1.66-1.42 (m, 4H), 1.41-1.29 (m, 1H), 1.29-1.11 (m, 1H) ppm; $^{13}$C NMR (125 MHz, $CDCl_3$) δ 205.7 (dd, J=30.4, 25.1 Hz), 167.1, 144.72, 130.0, 129.4, 128.6, 119.4 (dd, J=258.0, 250.7 Hz), 52.2, 46.4 (t, J=21.6), 39.1, 33.8 (t, J=4.8 Hz), 27.2, 24.3 (d, J=6.9 Hz), 24.1 (d, J=3.4 Hz), 22.9 ppm; $^{19}$F NMR (376 MHz, $CDCl_3$) δ −102.72 (d, 1F, J=245.5 Hz), −122.67 (d, 1F, J=251.7 Hz) ppm; HRMS (FAB) calcd for $C_{17}H_{20}O_3F_2$ [M+H]$^+$ 311.1459. found 311.1467.

5. To a flame-dried round bottom flask under a $N_2$ atmosphere was added THF (80 mL), followed by KHMDS (8.28 mL, 4.14 mmol). The reaction mixture was cooled to −78° C. with stirring, and ketone 4 (1.07 g, 3.45 mmol) in THF (35 mL) was added dropwise over 15 min. The reaction was stirred for an additional 40 min, then $Tf_2NPh$ (1.36 g, 3.80 mmol) in THF (35 mL) was added via syringe, and the system was then brought to rt with stirring over 1.5 h. The mixture was then quenched with MeOH (3 mL) concentrated under reduced pressure, diluted with ether, filtered through a silica gel plug, and again concentrated. The crude mixture was then flash chromatographed twice (0-5% EtOAc in 4:1 hexanes:toluene with 1% $Et_3N$, then 0-1% EtOAc in 2:1 hexanes:toluene) to yield a pale yellow oil (1.13, 74%). $R_f$=0.60 (4:1 hexanes:EtOAc); $^1$H NMR (400 MHz, $CD_3CN$) δ 7.93 (d, 2H, J=8.2 Hz), 7.36 (d, 2H, J=8.2 Hz), 6.25 (t, 1H, J=9.4 Hz), 3.85 (s, 3H), 3.24 (dd, 1H, J=13.5, 3.8 Hz), 2.88-2.70 (m, 1H), 2.61 (dd, 1H, J=13.5, 10.2 Hz), 2.56-2.42 (m, 1H), 2.41-2.30 (m, 1H), 1.68-1.52 (m, 3H), 1.51-1.44 (m, 2H), 1.43-1.34 (m, 1H) ppm; $^{13}$C NMR (125 MHz, $CD_3CN$) δ 167.6, 145.8, 143.6 (t, J=29.4 Hz), 130.5, 130.4, 129.5, 129.1 (t, J=4.0 Hz), 120.5 (dd, J=246.2, 243.1 Hz), 119.5 (q, J=319.1 Hz), 52.7, 46.8 (apt t, J=22.0 Hz), 35.2 (apt d, J=5.4 Hz), 27.0, 26.2, 23.0, 21.8 ppm; $^{19}$F NMR (376 MHz, $CD_3CN$) δ −74.45 (s, 3F), −93.93 (d, 1F, J=272.2 Hz), −105.18 (d, 1F, J=266.9 Hz) ppm; HRMS (FAB) calcd for $C_{18}H_{19}O_5F_5S$ [M+H]$^+$ 443.0952. found 443.0960.

6. To a flame-dried round bottom flask under a $N_2$ atmosphere was added vinyl triflate 5 (986 mg, 2.23 mmol) in THF (50 mL). The mixture was cooled to −20° C. with stirring. In a separate flame-dried round bottom flask, a 0.198 M solution of LDA was made by adding n-butyllithium (2.68 mL, 6.69 mmol) to a solution of diisopropylamine (1.13 mL, 8.03 mmol) in THF (30.0 mL) stirring under a $N_2$ atmosphere at −78° C. A portion of the LDA solution (13.5 mL, 2.67 mmol) was added dropwise to the first mixture over 1 h. The reaction mixture was then brought to rt over 30 min, quenched with MeOH (5 mL), concentrated under reduced pressure, and purified by flash chromatography (0-3% EtOAc in 2:1 hexanes:toluene) to yield a white solid (529 mg, 81%). $R_f$=0.50 (1:2 hexane:toluene); mp 78.5-82.7° C.; $^1$H NMR (400 MHz, $CDCl_3$) δ 7.99 (d, 2H, J=8.1 Hz), 7.27 (d, 2H, J=7.9 Hz), 3.92 (s, 3H), 3.16 (apt d, 1H, J=11.2 Hz), 2.60-2.43 (m, 2H), 2.41-2.24 (m, 2H), 2.10-1.88 (m, 2H), 1.87-1.68 (m, 2H), 1.62-1.44 (m, 1H), 1.21-1.08 (m, 1H) ppm; $^{13}$C NMR (125 MHz, $CDCl_3$) δ 167.2, 145.5, 130.0, 129.4, 128.4, 119.5 (t, J=238.6 Hz), 109.9 (t, J=11.1 Hz), 85.1 (dd, J=47.2, 41.6 Hz), 58.2 (t, J=24.3 Hz), 52.2, 34.5 (d, J=4.7 Hz), 32.6, 30.8 (d, J=4.4 Hz), 28.0, 20.4 ppm; $^{19}$F NMR (376 MHz, $CDCl_3$) δ −94.32 (d, 1F, J=260.2 Hz), −101.36 (dm, 1F, J=259.8 Hz) ppm; HRMS (FAB) calcd for $C_{17}H_{18}O_2F_2$ [M+H]$^+$ 293.1353. found 293.1357.

7. To a round bottom flask fitted with a reflux condenser were added difluorocyclooctyne methyl ester 6 (442 mg, 1.51 mmol), LiOH (723 mg, 30.2 mmol), water (1.75 mL), and dioxane (7 mL). The reaction was heated to 55° C. and stirred for 7 h. The mixture was then cooled to rt, diluted with 1 M HCl (10 mL), and extracted with $CH_2Cl_2$ (20 mL, 4×). The combined organic layers were then washed (1:1 1 M HCl: brine, 40 mL), dried over $Na_2SO_4$, filtered through a glass frit, and concentrated under reduced pressure. The crude product was then purified by flash chromatography (9:1 hexanes: EtOAc with 1% AcOH) to yield a white solid (360 mg, 86%). $R_f$=0.45 (4:1 hexanes:EtOAc with 1% AcOH); mp 182.0 (dec); $^1$H NMR (400 MHz, $CD_3CN$) δ 10.10-8.80 (br s, 1H), 7.94 (d, 2H, J=8.2 Hz), 7.35 (d, 2H, J=8.1), 3.10 (d, 1H, J=10.9 Hz), 2.70-2.50 (m, 2H), 2.43-2.24 (m, 2H), 2.04-1.84 (m, 2H) 1.83-1.67 (m, 2H), 1.55-1.41 (m, 1H), 1.22-1.11 (m, 1H) ppm; $^{13}$C NMR (125 MHz, $d_6$-acetone) δ 167.6, 146.2, 130.8, 130.2, 129.6, 120.2 (dd, J=239.1, 235.4 Hz), 111.6 (apt t, J=11.3 Hz), 85.5 (dd, J=46.7, 41.9 Hz), 58.6 (t, J=24.2 Hz), 34.9 (d, J=4.9 Hz), 33.3 (d, J=2.1 Hz), 31.6 (d, J=4.7 Hz), 28.4, 20.5 ppm; $^{19}$F NMR (376 MHz, $CD_3CN$) δ −93.81 (d, 1F, J=258.7 Hz), −101.32 (ddt, 1F, J=258.8, 20.3, 7.0 Hz) ppm; HRMS (FAB) calcd for $C_{16}H_{16}O_2F_2$ [M+H]$^+$ 279.1197 found 279.1190.

8. To a flame-dried round bottom flask were added DCC (3.66 g, 17.7 mmol), DMAP (98.6 mg, 0.807 mmol), 3-methyl-3-oxetanemethanol (1.59 mL, 16.1 mmol), and $CH_2Cl_2$ (20 mL). A $N_2$ atmosphere was established, and the mixture was cooled to 0° C. with stirring. Iodoacetic acid (3.00 g, 16.1 mmol) was then added in $CH_2Cl_2$ (30 mL) via syringe. The reaction mixture was stirred for 1 h, and then was brought to rt over 1.5 h, quenched with acetic acid (1 mL), and stirred an additional 30 min. The mixture was then diluted with $CH_2Cl_2$ and filtered through Celite to remove DCU. The filtrate (300 mL total) was then washed with water (200 mL), saturated $NaHCO_3$ (200 mL, 2×) to remove residual acids, and brine (200 mL). The organic layer was then dried over $MgSO_4$, filtered through a glass frit, and concentrated under reduced pressure. At this point residual DCU precipitated from the solution, so it was diluted with $CH_2Cl_2$ and again filtered through Celite. The filtrate was again concentrated to yield a yellow oil. This material was then transferred to a new round bottom flask and dissolved in THF (100 mL). Triphenyl phosphine (4.65 g, 17.7 mmol) was then added, and the reaction was stirred under $N_2$ at rt for 40 h. The reaction mixture was then diluted with diethyl ether (100 mL) and filtered through a glass frit to isolate the precipitated product. Residual solvent was removed under reduced pressure to yield a white solid (7.93 g, 92%). Mp 152.8-154.6° C.; $^1$H NMR (400 MHz, $CDCl_3$) δ 7.93-7.84 (m, 6H), 7.84-7.78 (m, 3H), 7.73-7.65 (m, 6H), 5.51 (d, 2H, J=13.5 Hz) 4.26 (s, 4H), 4.15 (s, 2H), 1.22 (s, 3H) ppm; $^{13}$C NMR (125 MHz, $CDCl_3$) δ 164.3 (d, J=3.5 Hz), 135.4 (d, J=3.1 Hz), 133.9 (d, J=10.8 Hz), 130.4 (d, J=13.2 Hz), 117.4 (d, J=89.2 Hz), 79.1, 71.1, 38.8, 33.6 (d, J=56.6 Hz), 21.0 ppm; $^{31}$P NMR (162 MHz, $CDCl_3$) δ 20.41 (s, 1P) ppm; HRMS (ES$^+$) calcd for $C_{25}H_{26}O_3P$, 405.1620. found 405.1631.

9. To a flame-dried round bottom flask were added phosphonium iodide 8 (831 mg, 1.56 mmol) and $CH_2Cl_2$ (10 mL), and a $N_2$ atmosphere was established. DBU (0.212 mL, 1.42 mmol) was added, and the reaction mixture was stirred for 20 min. In a separate flame-dried round bottom flask, difluorodiketone 1 (250 mg, 1.42 mmol) was dissolved in $CH_2Cl_2$ (20 mL), and this solution was then transferred to the first solution. The reaction mixture was allowed to stir for 24 h, concentrated under reduced pressure, and purified by flash chromatography (10:1 hexanes:EtOAc), yielding a white solid (364 mg, 85%). $R_f$=0.50 (2:1 hexanes:EtOAc); mp 44.2-46.0° C.; $^1$H NMR (500 MHz, $CDCl_3$) δ 6.49 (s, 1H), 4.51 (d, 2H, J=6.0 Hz), 4.40 (d, 2H, J=6.0 Hz), 4.25 (s, 2H), 2.81 (t, 2H, J=6.6 Hz), 2.66 (t, 2H, J=6.7 Hz), 1.82 (m, 2H), 1.72 (m, 2H), 1.52 (m, 2H), 1.35 (s, 3H) ppm; $^{13}$C NMR (125 MHz, $CDCl_3$) δ 200.2 (t, J=28.1 Hz), 165.1, 150.4 (t, J=20.0 Hz), 121.1 (t, J=9.6 Hz), 114.2 (t, J=254.6 Hz), 79.7, 69.3, 39.2, 37.5, 26.72, 26.66, 26.0, 25.5, 21.3 ppm; $^{19}$F NMR (376 MHz, $CD_3CN$) δ −113.03 (s, 2F) ppm; HRMS (FAB) calcd for $C_{15}H_{20}O_4F_2$ [M+H]$^+$ 303.1408. found 303.1404.

10. To a round bottom flask were added α,β-unsaturated ester 9 (804 mg, 2.66 mmol) and MeOH (30 mL). The system was flushed with $N_2$ and a catalytic amount of Pd/C was added. The system was then again flushed with $N_2$, followed by $H_2$, and the reaction mixture was stirred under a $H_2$ atmosphere for 18 h. The system was then again flushed with $N_2$, and the reaction mixture was diluted with $CH_2Cl_2$ (30 mL) and filtered through Celite to remove the catalyst. The filtrate was then concentrated under reduced pressure. The crude material was then dissolved in $CH_2Cl_2$ (17 mL) and transferred via syringe to a new flame-dried round bottom flask, which was under a $N_2$ atmosphere and contained 4 Å molecular sieves. The mixture was then cooled to 0° C. with stirring. In a separate flame-dried conical flask was prepared a 0.20 M solution of $BF_3.OEt_2$ (100 μL) in $CH_2Cl_2$ (3.9 mL), and a portion of this solution (1.0 mL, 0.20 mmol) was added to the reaction mixture via syringe. The reaction mixture was then brought to rt and was stirred for an additional 20 h before being quenched with $Et_3N$ (0.5 mL). The reaction mixture was then concentrated under reduced pressure and was purified by flash chromatography (20:1 hexanes:EtOAc with 1% $Et_3N$ over deactivated silica gel) to yield a white solid (731 mg, 90% over two steps). $R_f$=0.70 (2:1 hexanes:EtOAc); mp 80.3-83.3° C.; $^1$H NMR (500 MHz, $CDCl_3$) δ 3.89 (s, 6H), 2.65 (m, 1H), 2.62-2.46 (m, 2H), 2.21 (d, 1H, J=14.6 Hz), 2.10-1.94 (m, 2H), 1.90 (br s, 1H), 1.60 (m, 2H), 1.56-1.42 (m, 2H), 1.36 (m, 2H), 0.80 (s, 3H) ppm; $^{13}$C NMR (125 MHz, $CDCl_3$) δ 205.8 (dd, J=29.7, 25.7 Hz), 119.3 (dd, J=257.6, 250.2 Hz), 109.0, 72.8, 39.2 (t, J=21.2 Hz), 38.9, 34.6 (t, J=4.7 Hz), 30.5, 27.0, 26.3 (d, J=7.2 Hz), 24.8 (d, J=2.7 Hz), 23.3, 14.7 ppm; $^{19}$F NMR (376 MHz, $CD_3CN$) δ −103.10 (d, 1F, J=246.4 Hz), −124.20 (dm, 1F, J=248.97 Hz) ppm.

11. To a flame-dried round bottom flask under a $N_2$ atmosphere was added THF (30 mL) followed by KHMDS (2.66 mL, 1.33 mmol). The reaction mixture was cooled to −78° C. with stirring, and ketone 10 (354 mg, 1.16 mmol) in THF (15 mL) was added dropwise via syringe over 15 min. The reaction was stirred for an additional 3 h, then Tf$_2$NPh (457 mg, 1.28 mmol) in THF (15 mL) was added via syringe, and the system was slowly brought to rt with stirring over 19 h. The mixture was then quenched with deactivated silica gel, concentrated under reduced pressure, and purified by flash chromatography (5-6.5% EtOAc:hexanes with 1% Et$_3$N over deactivated silica gel) to yield a white solid (407 mg, 80%). R$_f$=0.72 (2:1 hexanes:EtOAc); mp 81.2-83.3° C.; $^1$H NMR (400 MHz, CDCl$_3$) δ 6.05 (t, 1H, J=9.6 Hz), 3.89 (s, 6H), 2.74-2.06 (m, 1H), 2.51-2.31 (m, 2H), 2.20 (dd, 1H, J=14.5, 1.7 Hz), 2.00-1.87 (m, 1H), 1.72-1.49 (m, 6H), 0.80 (s, 3H) ppm; $^{13}$C NMR (125 MHz, CDCl$_3$) δ 143.2 (t, J=30.2 Hz), 126.9, 119.2 (apt t, J=246.5 Hz), 118.6 (q, J=320.0 Hz), 108.9, 72.8, 40.9 (apt t, J=22.3 Hz), 35.1, 30.5, 27.2, 26.6, 22.6, 21.8, 14.6 ppm; $^{19}$F NMR (376 MHz, CDCl$_3$) δ −74.52 (s, 3F), −93.80 (d, 1F, J=269.8 Hz), −104.75 (dm, 1F, J=278.0 Hz) ppm; HRMS (FAB) calcd for C$_{16}$H$_{21}$O$_6$F$_5$S [M+H]$^+$ 437.1057 found 437.1050.

12. In a round bottom flask, vinyl triflate 11 (407 mg, 0.932 mmol) was dissolved in toluene and subsequently concentrated under reduced pressure 4 times to remove trace moisture. The material was then dissolved in THF (20 mL), a N$_2$ atmosphere was established, and the solution was cooled to −20° C. with stirring. In a separate flame-dried round bottom flask, a 0.20 M solution of LDA was made by adding n-butyllithium (1.12 mL, 2.80 mmol) to a solution of diisopropylamine (475 µL, 3.36 mmol) in THF (12.4 mL) stirring under a N$_2$ atmosphere at −78° C. A portion of the LDA solution (5.6 mL, 1.12 mmol) was added dropwise via syringe to the first mixture over 1 h. The reaction mixture was then brought to rt over 30 min, quenched with deactivated silica gel, concentrated under reduced pressure, and purified by flash chromatography (5-6.5% EtOAc:hexanes over deactivated silica gel) to yield a white solid (158.7 mg, 59%). R$_f$=0.73 (2:1 hexanes:EtOAc); mp 80.1-86.0° C.; $^1$H NMR (500 MHz, CDCl$_3$) δ 3.90 (s, 6H), 2.54 (apt dq, 1H, J=23.5, 9.1 Hz), 2.40-2.25 (m, 2H), 2.25-2.11 (m, 2H), 2.10-2.02 (m, 2H), 1.81-1.71 (m, 1H), 1.65 (dd, 1H, J=14.6, 10.3 Hz), 1.50 (apt quint, 1H, J=7.5 Hz), 1.33 (m, 1H), 0.81 (s, 3H) ppm; $^{13}$C NMR (125 MHz, CDCl$_3$) δ 120.0 (t, J=238.3 Hz), 109.8 (t, J=11.2 Hz), 85.4 (dd, 47.1, 41.8 Hz), 72.8, 51.9 (t, J=23.8 Hz), 35.2 (dd, J=4.5, 1.6 Hz), 32.8 (d, J=4.8 Hz), 32.7 (d, J=2.1 Hz), 30.5, 29.9, 28.2, 20.5, 14.8 ppm; $^{19}$F NMR (376 MHz, CD$_3$CN) δ −94.82 (d, 1F, J=258.7 Hz), −101.81 (ddt, 1F, J=259.3, 24.1, 7.2 Hz) ppm.

13. To a scintillation vial were added difluorocyclooctyne orthoester 12 (90.4 mg, 0.316 mmol), MeOH (4.5 mL), water (450 µL), and PPTS (159 mg, 0.632 mmol). The reaction mixture was stirred at rt for 24 h, then quenched with saturated NaHCO$_3$ (2 mL) and concentrated under reduced pressure. The material was then diluted with brine (8 mL) and extracted with EtOAc (15 mL, 1×; 5 mL, 2×). The combined organic layer was then washed with brine (10 mL, 1×) and a HCl/brine solution (1:1 1 M HCl:brine, 10 mL, 2×), dried over MgSO$_4$, and filtered through a glass frit. The filtrate was then concentrated under reduced pressure to yield a white solid. A portion of this material (57.8 mg) was transferred to a round bottom flask, where it was dissolved in dioxane (1 mL) and water (200 µL). To this was added LiOH (91 mg, 3.8 mmol) and the reaction mixture was stirred at rt for 3 h, then quenched with 1 M HCl (5 mL). The mixture was further diluted with brine (3 mL) and extracted with EtOAc (10 mL, 4×). The combined organic layers were then washed with and HCl/brine solution (1:1 1 M HCl:brine, 10 mL), dried over MgSO$_4$, and filtered through a glass frit. The filtrate was then concentrated and purified by flash chromatography (20:1 hexanes:EtOAc with 2% AcOH) to give a white solid (33.2 mg, 86% over two steps). R$_f$=0.66 (1:1 hexanes:EtOAc with 1% AcOH); mp 87.4-88.9° C.; $^1$H NMR (400 MHz, CDCl$_3$) δ 11.90-10.60 (br s, 1H), 2.84-2.69 (m, 2H), 2.46-2.28 (m, 3H), 2.21-2.05 (m, 2H), 1.90-1.74 (m, 2H), 1.67 (m, 1H), 1.41 (m, 1H) ppm; $^{13}$C NMR (125 MHz, CDCl$_3$) δ 177.8, 119.1 (t, J=238.6 Hz), 110.7 (t, J=11.2 Hz), 84.7 (dd, J=47.0, 41.6 Hz), 52.6 (t, J=24.4 Hz), 33.7 (apt d, J=4.4 Hz), 32.9 (d, J=4.6 Hz), 32.7 (d, J=2.0 Hz), 27.9, 20.5 ppm; $^{19}$F NMR (376 MHz, CDCl$_3$) δ −94.64 (d, 1F, J=260.0 Hz), −100.82 (ddt, 1F, J=260.2, 21.1, 6.8 Hz) ppm; HRMS (ES$^-$) calcd for C$_{10}$H$_{11}$O$_2$F$_2$ [M]$^-$ 201.0722. found 201.0729.

Kinetic Evaluation of [3+2] Cycloaddition of DIFO2 and DIFO3 with Benzyl Azide.

Stock solutions of DIFO2 (7, 20 mM) or DIFO3 (12, 20 mM) and benzyl azide (200 mM) were made in CD$_3$CN. An NMR tube was charged with 450 µL of the solution of 1, and, immediately before lowering into the NMR magnet, 50 µL of the benzyl azide solution, and the reaction was monitored over time using $^1$H NMR spectroscopy. The kinetic data were derived by monitoring the change in integration of resonances corresponding to the benzylic protons in benzyl azide (δ ~4.4 ppm) compared to the corresponding resonances of the triazole products (δ ~5.5 to 5.7 µm).

The second-order rate constant for the reaction was determined by plotting 1/[benzyl azide] versus time, followed by subsequent analysis by linear regression. The second-order rate constant (k, M$^{-1}$ s$^{-1}$) corresponds to the determined slope.

Cell Surface Labeling of Azido Glycans on Jurkat Cells with Biotinylated Conjugates—a Comparison Between DIFO-Biotin, DIFO2-Biotin, and DIFO3-Biotin.

Jurkat (human T-cell lymphoma) and Chinese hamster ovary (CHO) cells were maintained in a 5% CO$_2$, water-saturated atmosphere and grown in RPMI-1640 (Jurkat) or F12 (CHO) media supplemented with 10% FCS, penicillin (100 units/mL), and streptomycin (0.1 mg/mL). Cell densities were maintained between 1×10$^5$ and 1.6×10$^6$ cells/mL.

Jurkat cells were incubated for 1-3 d in untreated media or media containing 25 µM Ac$_4$ManNAz. The cells were then distributed into a 96-well V-bottom tissue culture plate, pelleted (3500 rpm, 3 min), and washed twice with 200 µL of labeling buffer (PBS, pH 7.4 containing 1% FCS). Cells were then incubated with DIFO-biotin, DIFO2-biotin, or DIFO3-biotin in labeling buffer for 1 h at rt at various concentrations (1-10 µM) with dilutions made from a 2.5 mM stock in 7:3 PBS:DMF. After incubation, cells were pelleted, washed twice with labeling buffer, and resuspended in the same buffer containing fluorescein isothiocyanate (FITC)-avidin (1:200 dilution of the Sigma stock). After a 15-min incubation on ice (in the dark), the cells were washed once with 200 µL, incubated with FITC-avidin for an additional 15 min on ice, washed three times with 200 µL of cold labeling buffer, and then diluted to a volume of 400 µL for flow cytometry analysis.

Figure 12:
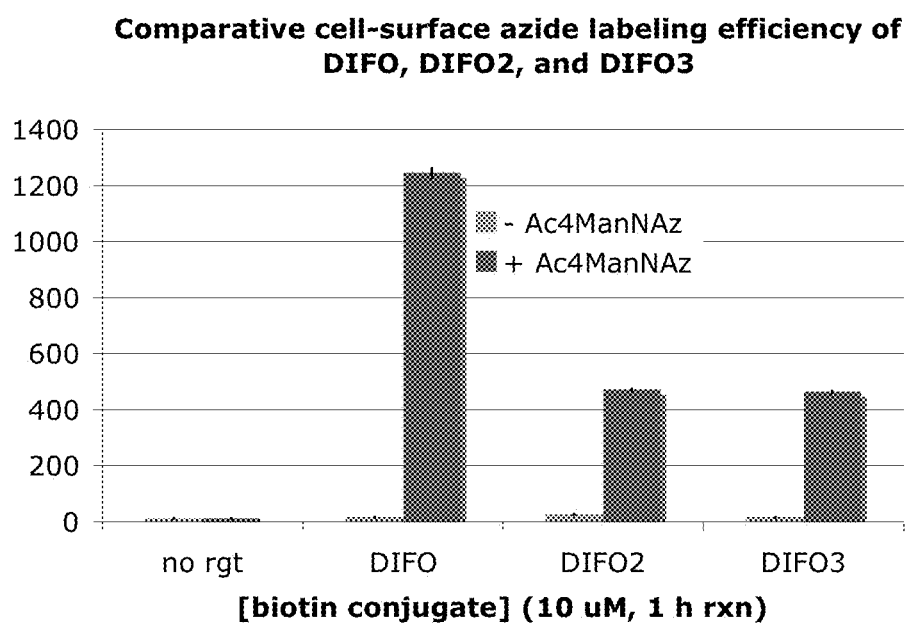
FIG. 12 presents comparative cell surface labeling of azido glycans by biotinylated derivatives of DIFO, DIFO2, and DIFO3.
Figure 13:
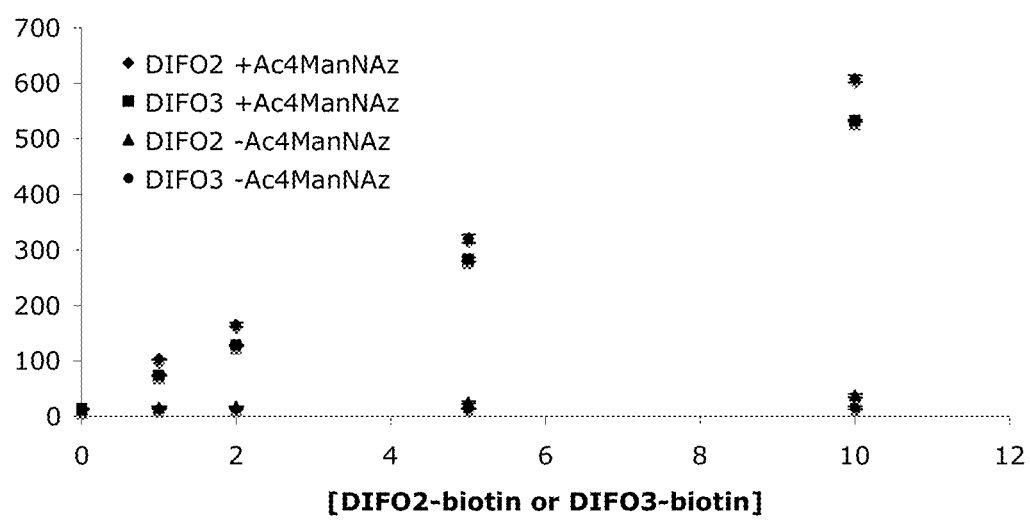
FIG. 13 depicts concentration dependence of the reaction of DIFO2-biotin and DIFO3-biotine with cell surface azido glycans.

The data are presented in FIGS. 12 and 13. FIG. 12 presents comparative cell surface labeling of azido glycans by biotinylated derivatives of DIFO, DIFO2, and DIFO3. FIG. 13 depicts concentration dependenc of the reaction of DIFO2-biotin and DIFO3-biotine with cell surface azido glycans. The x-axis is the concentration in µM; the y-axis is MFI, mean fluorescence intensity. Jurkat cells were incubated with 0 or 25 µM Ac$_4$ManNAz for 3 days. (FIG. 12) The cells were then reacted with 10 µM DIFO-biotin, DIFO2-biotin, or DIFO3-biotin for 1 h (FIG. 12), or reacted with various concentrations of DIFO2-biotin or DIFO3-biotin for 1 h (FIG. 13). In both cases, the cells were then stained with FITC-avidin, and analyzed by flow cytometry. Shown is the mean fluorescence intensity (MFI, arbitrary units). Error bars represent the standard deviation of triplicate samples.

The data presented in FIGS. 12 and 13 show that DIFO2-biotin and DIFO3-biotin can selectively label azide-containing membrane-associated glycans on live Jurkat cells; further, the data demonstrate that the sensitivity of azide detection using DIFO2 and DIFO3 is roughly 40% of that using DIFO.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

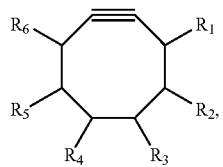

wherein each of $R_1$, $R_2$, $R_5$ and $R_6$ is independently H or a halogen atom; and $R_3$ is linked to $R_4$ through a C, O, N or S atom to form a substituted cycloalkyl or heterocycloalkyl ring which optionally is linked to a molecule of interest or a moiety that comprises a reactive group that facilitates covalent attachment of a molecule of interest.

2. The compound of claim 1, wherein $R_3$ is linked to $R_4$ through a carbon atom thus forming a substituted cycloalkyl ring.

3. The compound of claim 2, wherein the substituted cycloalkyl ring is a substituted cyclopropyl ring.

4. The compound of claim 2, wherein the substituted cycloalkyl ring is linked to a reactive group that facilitates covalent attachment of a molecule of interest, wherein the reactive group is selected from the group consisting of a carboxyl, an amine, an ester, a thioester, a sulfonyl halide, an alcohol, a thiol, a succinimidyl ester, an isothiocyanate, an iodoacetamide, a maleimide and a hydrazine.

5. The compound of claim 2, wherein the substituted cycloalkyl ring is linked to a molecule of interest selected from the group consisting of a detectable label, a toxin, a linker, a peptide, a drug, a member of a specific binding pair and an epitope tag.

6. The compound of claim 1 wherein $R^1$, $R^2$, $R^5$ and $R^6$ are each H; and $R_3$ is linked to $R_4$ through a carbon atom thus forming a substituted cycloalkyl ring.

7. The compound of claim 6, wherein the substituted cycloalkyl ring is a substituted cyclopropyl ring.

8. The compound of claim 6, wherein the substituted cycloalkyl ring is linked to a moiety that comprises a reactive group selected from the group consisting of a carboxyl, an amine, an ester, a thioester, a sulfonyl halide, an alcohol, a thiol, a succinimidyl ester, an isothiocyanate, an iodoacetamide, a maleimide and a hydrazine.

9. The compound of claim 6, wherein the substituted cycloalkyl ring is linked to a moiety that comprises a molecule of interest selected from the group consisting of a detectable label, a toxin, a linker, a peptide, a drug, a member of a specific binding pair and an epitope tag.

10. A method for chemoselective modification of a target molecule comprising an azide, the method comprising reacting an azide of a target molecule with the compound of claim 1, wherein said reacting produces a conjugate between the azide of the target molecule and the compound.

11. The method of claim 10, wherein the target molecule is a sugar.

12. The method of claim 11, wherein the sugar is a substrate of sialic acid biosynthesis.

13. The method of claim 11, wherein the sugar is mannosamine or acetylated mannosamine.

14. The method of claim 10, wherein the target molecule is an amino acid.

15. The method of claim 10, wherein the target molecule comprising the azide is expressed on a cell surface.

16. A method for synthetically modifying a cellular component, the method comprising:
    introducing an azide moiety into a cellular component, thereby generating an azide-modified cellular component; and
    contacting the cell comprising the azide-modified cellular component with a reactive partner comprising the compound of claim 1, said contacting being under physiological conditions;
    wherein said contacting with said reactive partner results in reaction between the azide group of azide-modified cellular component and the compound of claim 1, thereby synthetically and covalently modifying the cellular component.

* * * * *